(12) United States Patent
Klevan et al.

(10) Patent No.: US 11,636,190 B2
(45) Date of Patent: *Apr. 25, 2023

(54) SYSTEMS AND METHODS FOR IDENTIFYING AN INDIVIDUAL

(71) Applicant: LIFE TECHNOLOGIES CORPORATION, Carlsbad, CA (US)

(72) Inventors: Leonard Klevan, Cave Creek, AZ (US); Hugh Pasika, San Francisco, CA (US); Ravi Gupta, Foster City, CA (US); Allan Minn, Daly City, CA (US); Phillip McClurg, Aptos, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/915,667

(22) Filed: Jun. 29, 2020

(65) Prior Publication Data
US 2020/0401681 A1 Dec. 24, 2020

Related U.S. Application Data

(60) Division of application No. 15/869,717, filed on Jan. 12, 2018, now Pat. No. 10,733,277, which is a
(Continued)

(51) Int. Cl.
*G06F 21/32* (2013.01)
*H04L 9/32* (2006.01)
(Continued)

(52) U.S. Cl.
CPC .............. *G06F 21/32* (2013.01); *G06F 21/34* (2013.01); *G06F 21/602* (2013.01);
(Continued)

(58) Field of Classification Search
CPC ...... G06F 21/32; G06F 21/34; G06F 21/6245; G06F 16/25; G06F 21/602; G07C 9/257;
(Continued)

(56) References Cited

U.S. PATENT DOCUMENTS 4,993,068 A 2/1991 Piosenka et al.
6,812,339 B1 11/2004 Venter et al.
(Continued)

FOREIGN PATENT DOCUMENTS

EP 1237327 A2 9/2002
EP 1385117 A2 1/2004
(Continued)

OTHER PUBLICATIONS

"On Enabling Secure Applications Through Off-Line Biometric Identification"—1998 IEEE Symposium on Security and Privacy, vol. 19, May 6, 1998 https://ieeexplore.ieee.org/document/674831 (Year: 1998).*
(Continued)

*Primary Examiner* — Randy A Scott
(74) *Attorney, Agent, or Firm* — Workman Nydegger; Logan Christenson; John Guynn

(57) ABSTRACT

The present application relates to systems and methods using biometric data of an individual for identifying the individual and/or verifying the identity of an individual. These systems and methods are useful for, amongst many applications, more secure identification of high-risk individuals attempting to gain access to an entity, transport, information, location, security organization, law enforcement organization, transaction, services, authorized status, and/or funds.

16 Claims, 18 Drawing Sheets

Related U.S. Application Data division of application No. 15/350,196, filed on Nov. 14, 2016, now abandoned, which is a division of application No. 14/794,268, filed on Jul. 8, 2015, now Pat. No. 9,520,999, which is a continuation of application No. 13/593,318, filed on Aug. 23, 2012, now Pat. No. 9,094,211.

(60) Provisional application No. 61/674,213, filed on Jul. 20, 2012, provisional application No. 61/528,106, filed on Aug. 26, 2011.

(51) Int. Cl.
| | |
|---|---|
| *G06F 21/34* | (2013.01) |
| *G06F 21/62* | (2013.01) |
| *G07C 9/25* | (2020.01) |
| *G06F 21/60* | (2013.01) |
| *G06Q 50/26* | (2012.01) |
| G06F 16/25 | (2019.01) |
| G16B 30/00 | (2019.01) |
| G16B 50/00 | (2019.01) |
| G06V 40/50 | (2022.01) |
| G06F 7/02 | (2006.01) |

(52) U.S. Cl.
CPC ....... *G06F 21/6245* (2013.01); *G06Q 50/265* (2013.01); *G07C 9/257* (2020.01); *H04L 9/3231* (2013.01); *H04L 9/3234* (2013.01); *H04L 9/3242* (2013.01); *H04L 9/3268* (2013.01); *G06F 7/02* (2013.01); *G06F 16/25* (2019.01); *G06V 40/50* (2022.01); *G16B 30/00* (2019.02); *G16B 50/00* (2019.02)

(58) Field of Classification Search
CPC ... H04L 9/3242; H04L 9/3268; H04L 9/3234; G06Q 50/265
See application file for complete search history.

(56) References Cited

U.S. PATENT DOCUMENTS

| | | | |
|---|---|---|---|
| 6,957,337 | B1 | 10/2005 | Chainer et al. |
| 7,336,806 | B2 | 2/2008 | Schonberg et al. |
| 7,492,925 | B2 | 2/2009 | Silvester |
| 7,606,396 | B2 | 10/2009 | Miller et al. |
| 7,761,715 | B1 | 7/2010 | Califano et al. |
| 8,005,277 | B2* | 8/2011 | Tulyakov ........... G06V 40/1353 |
| | | | 382/125 |
| 9,094,211 | B2 | 7/2015 | Klevan et al. |
| 9,520,999 | B2 | 12/2016 | Klevan et al. |
| 2002/0129251 | A1* | 9/2002 | Itakura ................. H04L 9/3247 |
| | | | 713/176 |
| 2002/0170966 | A1 | 11/2002 | Hannigan et al. |
| 2003/0086591 | A1 | 5/2003 | Simon |
| 2003/0115475 | A1 | 6/2003 | Russo et al. |
| 2004/0064453 | A1 | 4/2004 | Ruiz et al. |
| 2004/0158723 | A1 | 8/2004 | Root |
| 2006/0005042 | A1 | 1/2006 | Black |
| 2006/0016876 | A1 | 1/2006 | Bonalle et al. |
| 2006/0104485 | A1 | 5/2006 | Miller et al. |
| 2006/0210119 | A1 | 9/2006 | Willis et al. |
| 2006/0222211 | A1 | 10/2006 | Olivo et al. |
| 2006/0286569 | A1 | 12/2006 | Bar-Or et al. |
| 2007/0016777 | A1 | 1/2007 | Henderson et al. |
| 2007/0041622 | A1 | 2/2007 | Salva |
| 2007/0195999 | A1 | 8/2007 | Willis |
| 2007/0253608 | A1* | 11/2007 | Tulyakov ........... G06K 9/00073 |
| | | | 382/125 |
| 2008/0027756 | A1 | 1/2008 | Gabriel et al. |
| 2008/0059807 | A1 | 3/2008 | Miller, Jr. et al. |
| 2008/0209227 | A1 | 8/2008 | Venkatesan et al. |
| 2008/0222426 | A1 | 9/2008 | Schrijen et al. |
| 2009/0058598 | A1 | 3/2009 | Sanchez et al. |
| 2009/0160658 | A1 | 6/2009 | Armstrong et al. |
| 2009/0174526 | A1 | 7/2009 | Howard et al. |
| 2009/0277790 | A1 | 11/2009 | Asogawa et al. |
| 2009/0319591 | A1 | 12/2009 | Allen et al. |
| 2010/0058063 | A1* | 3/2010 | Tuyls .................... H04L 9/3247 |
| | | | 713/172 |
| 2010/0208950 | A1 | 8/2010 | Silvester |
| 2011/0067108 | A1 | 3/2011 | Hoglund |
| 2011/0093426 | A1 | 4/2011 | Hoglund |
| 2011/0179289 | A1 | 7/2011 | Guenther |
| 2011/0202466 | A1 | 8/2011 | Carter |
| 2014/0250517 | A1 | 9/2014 | Kim et al. |
| 2017/0123415 | A1 | 5/2017 | Thörn |

FOREIGN PATENT DOCUMENTS

| | | |
|---|---|---|
| EP | 2397961 A2 | 12/2011 |
| EP | 2418603 A1 | 2/2012 |
| WO | WO-9847110 A1 | 10/1998 |
| WO | WO-03026190 A1 | 3/2003 |
| WO | WO-03040931 A1 | 5/2003 |
| WO | WO-2004012383 A1 | 2/2004 |
| WO | WO-2005001748 A2 | 1/2005 |
| WO | WO-2005119581 A1 | 12/2005 |
| WO | WO-2007084153 A2 | 7/2007 |
| WO | WO-2007113888 A1 | 10/2007 |
| WO | WO-2008005361 A2 | 1/2008 |
| WO | WO-2008019800 A1 | 2/2008 |
| WO | WO-2008031167 A1 | 3/2008 |
| WO | WO-2008054868 A2 | 5/2008 |
| WO | WO-2008139387 A1 | 11/2008 |
| WO | WO-2009055303 A1 | 4/2009 |
| WO | WO-2013032869 A1 | 3/2013 |
| WO | WO-2014015346 A1 | 1/2014 |

OTHER PUBLICATIONS

"Symmetric Hash Functions for Secure Fingerprint Biometric Systems"—Tulyakov et al., Elsevier, Science Direct, Aug. 19, 2007 http://cubs.cedar.buffalo.edu/images/pdf/pub/symmetric-hash-functions-for-secure-fingerprint-biometric-systems.pdf (Year: 2007).*
Davida, G. et al. "On Enabling Secure Applications through Off-Line Biometric Identification" Proceedings of the 1998 IEEE Symposium on Security and Privacy, Oakland, CA, vol. 19, 1998, pp. 148-157.
Isenor, D. K. et al., "Fingerprint Identification Using Graph Matching", Pattern Recognition, vol. 19, No. 2, 1986, pp. 113-122.
Kornblum, Jesse , "Identifying almost identical files using context triggered piecewise hashing", Digital Investigation, 3S, 2006, pp. S91-S97.
PCT/US2012/052130, "International Search Report and Written Opinion of the International Searching Authority", dated Nov. 28, 2012, 12 pages.
PCT/US2013/051536, , "International Search Report and Written Opinion", dated Oct. 24, 2013, 1-16.
Tulyakov, et al., "Symmetric hash functions for secure fingerprint biometric systems", Pattern Recognition Letters vol. 28, 2007, 2427-2436.

* cited by examiner

SYSTEMS AND METHODS FOR IDENTIFYING AN INDIVIDUAL

CROSS REFERENCE TO RELATED APPLICATIONS

This application is a divisional of U.S. application Ser. No. 15/869,717 filed Jan. 12, 2018, which is a divisional of U.S. application Ser. No. 15/350,196 filed Nov. 14, 2016 (now abandoned), which is a divisional of U.S. application Ser. No. 14/794,268 filed Jul. 8, 2015 (now U.S. Pat. No. 9,520,999), which is a continuation of U.S. application Ser. No. 13/593,318 filed Aug. 23, 2012 (now U.S. Pat. No. 9,094,211), which claims benefit of priority under 35 U.S.C. § 119(e) to U.S. Provisional Application No. 61/528,106 filed Aug. 26, 2011 and U.S. Provisional Application No. 61/674,213 filed Jul. 20, 2012. The entire contents of the aforementioned applications are incorporated by reference herein.

FIELD

The present application relates to systems and methods using biometric data of an individual for identifying the individual and/or verifying the identity of an individual. These systems and methods are useful for, amongst many applications, more secure identification of high-risk individuals at points of access to an entity, transport, information, location, security organization, law enforcement organization, transaction, services, authorized status, funds, and the like.

BACKGROUND

With the increased capability to retrieve evidence and obtain biometric data belonging to a group of individuals having attempted or succeeded in carrying out acts of violence or terrorism, there are growing databases managed by many governmental agencies. These databases may contain complete identification of such persons. However, frequently, databases may contain only partial identification of an individual deemed to be at high risk of perpetrating additional acts of violence or terrorism. There is a need for more effective identification of individuals in order to determine whether an individual presents risk if permitted to access an entity, transport, information, location, security organization, law enforcement organization, transaction, services, authorized status, funds, and the like, and optionally, is the person as recorded upon identification presented. The need for more effective identification additionally includes a need to protect the security of the identification information presented by an individual, as well as the privacy of that information.

Embodiments of the present invention may solve one or more of the above-mentioned problems. Other features and/or advantages, which may solve additional problems, may become apparent from the description which follows.

SUMMARY

In one aspect of the invention, a system for determining an identity of an individual, is provided including: a processor configured to: a) retrieve individualized identification information of the individual including an individualized biometric data of at least a first class and a first individualized identification hash comprising the individualized biometric data of the first class and the individualized biometric data of the second class; b) connect to at least one interrogation database comprising a plurality of interrogation biometric data of the second class; c) interrogate the at least one interrogation database wherein each of the plurality of interrogation biometric data of the second class is hashed together with the individualized biometric data of the first class to form a plurality of interrogation database identification hashes; d) compare each of the plurality of interrogation database identification hashes to the first individualized identification hash; and e) report whether a match of any of the plurality of database identification hashes to the first individualized identification is identified. The system may further include an identification card comprising the individualized identification information of the individual. The system may further include at least one interrogation database comprising a plurality of interrogation biometric data. The system may additionally include an enrollment database. In some embodiments, the individualized biometric data of the first class may be a fingerprint data or a retinal scan data. In other embodiments, the individualized biometric data of the first class may be an iris scan data, facial recognition scan data, or a body geometry scan data. In some embodiments, the individualized biometric data of the first class may be an iris scan data. In some embodiments, the individualized biometric data of the second class may be a DNA data selected from the group consisting of a STR profile, a SNP profile, an INDEL profile, and an Alu element. In other embodiments, the individualized biometric data of the second class may be a DNA data comprising a STR profile. In some embodiments, the individualized biometric data of the at least a first class may further include a third or more class of biometric data selected from the group consisting of a fingerprint scan data, iris scan data, retinal scan data, facial recognition scan data, and body geometry scan data and a DNA data, wherein the DNA data is selected from the group consisting of a STR profile, a SNP profile, an INDEL profile, and an Alu element. In various embodiments, when a class of individualized biometric data is a DNA data, then the DNA biometric data may be stored in a hashed form, where the hash may be a one-way hash. In some embodiments, the individualized biometric data of the first class may be stored separately from the first individualized identification hash. In various embodiments, the first individualized identification hash may be a barcode, alphanumerical or a graphical representation.

The processor of the system may be further configured to compare the individualized biometric data of the first class and/or the third or more class of biometric data with at least one interrogation biometric data of the at least one interrogation database. In other embodiments, the processor may be configured to: retrieve a plurality of partial individualized identification hashes, each comprising the individualized biometric data of the first class and a partial individualized biometric data of the second class. In some embodiments, the partial individualized biometric data of the second class may be a single locus or a subset of the loci of individualized biometric data of the second class. In some other embodiments, the processor may be further configured to compare the plurality of interrogation database identification hashes with the plurality of partial individualized identification hashes; and to report whether a match is identified. In yet other embodiments, the processor may be further configured to form a plurality of partial interrogation database identification hashes comprising the individualized biometric data of the first class and each of a plurality of partial interrogation database biometric data of the second class. In some embodiments, the partial interrogation biometric data of the second class may be a single locus or a subset of the loci of each of the plurality of the interrogation database biometric data. In some embodiments, the processor of the system may be further configured to compare each of the plurality of partial individualized identification hashes with each of the plurality of partial interrogation database identification hashes; and to report whether a match is identified. In various embodiments, the processor may be further configured to: a) read the first class of individualized biometric data at a point of contact; and b) confirm the first class of individualized biometric data at the point of contact. In yet other embodiments, the processor is further configured to: a) read the third or more class of individualized biometric data at a point of contact; and b) confirm the third class of individualized biometric data at the point of contact. In various embodiments, the processor may be further configured to connect to more than one interrogation database and to interrogate each of the more than one interrogation databases. In other embodiments, the processor may be further configured to: a) retrieve an enrollment verification certification; and interrogate an enrollment database to verify the authenticity of the identification card. In some embodiments, the identification card of the system includes an enrollment verification certification.

The system may further include a biometrics acquisition component configured to acquire individualized biometric data of the at least a first class and the second class from the individual; where the processor of the system may be further configured to: i) convert the biometric data of the first class into a digitized individualized biometric data; ii) store a first instance of the digitized individualized biometric data of the first class on the identification card; iii) convert the individualized biometric data of the second class into a digitized individualized biometric data; iv) hash a second instance of the digitized individualized biometric data of the first class with the digitized individualized biometric data of the second class to form a first individualized identification hash; and v) store the first individualized identification hash on an identification card. In other embodiments, the processor of the system may be further configured to: a) connect to an enrollment database; b) assign an enrollment verification certification; and c) store the enrollment verification certification.

The system may also provide a computer readable medium including computer readable instructions configured to instruct the processor to: a) retrieve individualized identification information of the individual comprising an individualized biometric data of at least a first class and a first individualized identification hash comprising the individualized biometric data of the first class and the individualized biometric data of the second class; b) connect to at least one interrogation database comprising a plurality of interrogation biometric data of the second class; c) interrogate the at least one interrogation database whereby each of the plurality of interrogation biometric data of the second class is hashed together with individualized biometric data of the first class to form a plurality of interrogation database identification hashes; d) compare each of the plurality of interrogation database identification hashes to the first individualized identification hash; and e) report whether a match of any of the plurality of database identification hashes to the first individualized identification hash is identified.

In another aspect, the invention provides an identification card including individualized identification information of an individual including an individualized biometric data of at least a first class and a first individualized identification hash including the individualized biometric data of the first class and the individualized biometric data of the second class. In some embodiments, when a class of individualized biometric data is a DNA data, then the DNA biometric data may be present on the identification card in a hashed form. In various embodiments, the individualized biometric data of the first class may be a fingerprint data or a retinal scan data. In other embodiments, the individualized biometric data of the first class may be an iris scan data. In various embodiments, the individualized biometric data of the second class may be a DNA data, selected from the group consisting of a STR profile, a SNP profile, an INDEL profile, and an Alu element. In some embodiments, the individualized biometric data of the second class is a DNA data comprising a STR profile. In some embodiments, the first individualized identification hash may be formed using a one-way hash. The identification card may further include individualized biometric data of a third or more class of biometric data selected from the group consisting of a fingerprint scan data, iris scan data, retinal scan data, facial recognition scan data, and body geometry scan data and a DNA data, including a STR profile, a SNP profile, an INDEL profile, or an Alu element. The identification card may further include a plurality of partial individualized identification hashes, wherein each partial individualized identification hash includes the individualized biometric data of the first class and a partial individualized biometric data of the second class. In some embodiments, the partial individualized biometric data of the second class is a single locus or a subset of the loci of a DNA profile. The identification card may further include an enrollment verification certification.

In another aspect of the invention, a method of identifying an individual is provided, including the steps of: a) retrieving individualized identification information including a first individualized identification hash of the individual where the first individualized identification hash comprises individualized biometric data of a first class and individualized biometric data of a second class; retrieving a individualized biometric data of the first class; accessing at least one interrogation database comprising a plurality of interrogation biometric data of the second class; hashing each of the plurality of interrogation biometric data of the second class together with the individualized biometric data of the first class to form a plurality of interrogation database identification hashes; comparing each of the plurality of interrogation database identification hashes to the first individualized identification hash; and reporting whether a match of any of the plurality of database identification hashes to the individualized identification hash is identified. The individualized identification information may be stored on an identification card. The individualized identification information may further include a third or more class of individualized biometric data selected from the group consisting of a fingerprint scan data, iris scan data, retinal scan data, facial recognition scan data, and body geometry scan data and a DNA data, wherein the DNA data is selected from the group consisting of a STR profile, a SNP profile, an INDEL profile, and an Alu element. In some embodiments, the individualized biometric data of the first class may be a fingerprint scan data or a retinal scan data. In other embodiments, the individualized biometric data of the first class may be an iris scan data. In some embodiments, the individualized biometric data of the second class is a DNA data selected from the group consisting of a STR profile, a SNP profile, an INDEL profile, and an Alu element. In some embodiments, the individualized biometric data of the second class is a DNA data comprising a STR profile. In some embodiments, when a class of individualized biometric data is a DNA data, then the individualized biometric DNA data is stored in a hashed form. In some embodiments, the hashed form of individualized biometric DNA data is a one-way hash. The method may include the steps of retrieving individualized biometric data of the first class or of the third or more class; accessing at least one interrogation database comprising a plurality of interrogation biometric data of the first class or of the third or more class; comparing each of the plurality of interrogation database biometric data to the individualized biometric data; and reporting a match of the database biometric data to the individualized biometric data. In some of the embodiments of the method, the individualized identification information may include a plurality of partial individualized identification hashes, each including the individualized biometric data of the first class and a partial individualized biometric data of the second class. In some embodiments, the partial individualized biometric data of the second class may be a single locus or a subset of the loci of the whole set of loci used in determining the DNA profile of the individual. In some embodiments, the method may also include steps of retrieving the plurality of partial individualized identification hashes; comparing the plurality of interrogation database identification hashes with the plurality of partial individualized identification hashes; and reporting whether a match is identified. In other embodiments, the method may also include the steps of forming a plurality of partial interrogation database identification hashes including the individualized biometric data of the first class and each of a plurality of partial interrogation database biometric data of the second class. The partial interrogation database biometric data may be a single locus or a subset of the loci of each of the interrogation database biometric data. The method may further include the steps of comparing each of the plurality of the partial individualized identification hashes to each of the plurality of the partial interrogation database biometric hashes; and reporting whether a match is identified. In some embodiments, the method also may include the steps of: reading the first class of individualized biometric data at a point of contact; and confirming the first class of individualized biometric data at the point of contact. In yet other embodiments, the method may include the steps of reading the third or more class of individualized biometric data at the point of contact; and confirming the third or more class of individualized biometric data at the point of contact. In some other embodiments, the method further includes the steps of: retrieving an enrollment verification certification; accessing an enrollment database; and determining whether the enrollment verification certification is valid.

In another aspect, the invention provides a computer readable medium including computer readable instructions, which when executed by a computer, operates on individualized identification information of an individual including an individualized biometric data of at least a first class and a first individualized identification hash including the individualized biometric data of the first class and an individualized biometric data of a second class, and instructs the computer to: a) connect with at least one interrogation database comprising a plurality of interrogation biometric data of the second class; b) interrogate the at least one interrogation database wherein each of the plurality of interrogation biometric data of the second class is hashed together with the individualized biometric data of the first class to form a plurality of interrogation database identification hashes; c) compare each of the plurality of interrogation database identification hashes to the individualized identification hash; and d) report whether a match of any of the plurality of database identification hashes to the first individualized identification hash is identified. In various embodiments, the biometric data of the first class may be a fingerprint data or a retinal scan data. In other embodiments, the individualized biometric data of the first class may be an iris scan. In various embodiments, the individualized biometric data of the second class may be a DNA data selected from the group consisting of a STR profile, a SNP profile, an INDEL profile, and an Alu element. In some embodiments, the individualized biometric data of the second class may be a DNA data comprising a STR profile. In other embodiments, the individualized identification information may further include a third or more class of individualized biometric data selected from the group consisting of a fingerprint scan data, iris scan data, retinal scan data, facial recognition scan data, and body geometry scan data and a DNA data, wherein the DNA data is selected from the group consisting of a STR profile, a SNP profile, an INDEL profile, and an Alu element. In various embodiments, when a class of individualized biometric data is a DNA data, then the DNA biometric data may be stored in a hashed form. In some embodiments, the hashed form may be a one-way hashed form. In various embodiments, the individualized identification information may be stored on an identification card. The computer readable medium may be further configured to instruct the computer to: a) read the first class of individualized biometric data at a point of contact; and b) confirm the first class of individualized biometric data at the point of contact. In other embodiments, the computer readable medium may further instruct the computer to: a) read the third class of individualized biometric data at the point of contact; and b) confirm the third class of individualized biometric data at the point of contact. In various embodiments, the individualized identification information further includes a plurality of partial individualized identification hashes, each comprising the individualized biometric data of the first class and each of a plurality of partial individualized biometric data of the second class. In some embodiments, the partial individualized biometric data of the second class may be a single locus or a subset of the loci of a DNA profile. The computer readable medium may be further configured to instruct the computer to: a) retrieve the plurality of partial individualized identification hashes; b) compare the plurality of interrogation database identification hashes with the plurality of partial individualized identification hashes; and c) report whether a match is identified.

In various embodiments, the computer readable medium may be further configured to instruct the computer to form a plurality of partial interrogation database identification hashes comprising the individualized biometric data of the first class and each of a plurality of partial interrogation database biometric data of the second class. In some embodiments, the partial interrogation database biometric data may be a single locus or a subset of the loci of each of the interrogation database biometric data. In some embodiments, the computer readable medium may further instruct the computer to: a) compare each of the plurality of the partial individualized identification hashes to each of the plurality of the partial interrogation database biometric hashes; and b) report whether a match is identified. In various embodiments, the computer readable medium may further instruct the computer to: a) retrieve an enrollment verification certification; and b) interrogate an enrollment database to determine whether the enrollment verification certification is valid.

In yet another aspect, the invention provides a computer readable medium including computer readable instructions, which when executed by a computer, operates on at least one biometrics acquisition component, and instructs the computer to: a) acquire individualized biometric data of at least a first and a second class from an individual; b) convert the individualized biometric data of the first class into a digital electronic format; c) store a first instance of the digitized individualized biometric data of the first class; d) convert the individualized biometric data of the second class into a digital electronic format; e) hash a second instance of the digitized individualized biometric data of the first class with the digitized individualized biometric data of the second class to form a first individualized identification hash; and f) store the first individualized identification hash. In some embodiments, the first individualized identification hash may be a one-way hash. In various embodiments, the computer readable medium may further instruct the computer to: a) acquire a third or more class of individualized biometric data; b) convert the third or more class of individualized biometric data to a digital electronic formats; and c) store the digitized third or more class of individualized biometric data.

In other embodiments, the computer readable medium may further instruct the computer to: a) convert the digitized individualized biometric data of the second class into a plurality of partial individualized biometric data of the second class; b) hash a second instance of the digitized individualized biometric data of the first class with each of the plurality of the digitized individualized biometric data of the second class to form a plurality of partial individualized identification hashes; and c) store the plurality of partial individualized identification hashes. The computer readable medium may be configured to further instruct the computer to: a) assign an enrollment verification certification; and b) store the enrollment verification certification. In various embodiments, the individualized identification information of the individual is stored on an identification card. In various embodiments, the computer readable medium may further include the computer readable medium including computer readable instructions, which when executed by a computer, operates on individualized identification information of an individual including an individualized biometric data of at least a first class and a first individualized identification hash including the individualized biometric data of the first class and an individualized biometric data of a second class, and instructs the computer to: a) connect with at least one interrogation database comprising a plurality of interrogation biometric data of the second class; b) interrogate the at least one interrogation database wherein each of the plurality of interrogation biometric data of the second class is hashed together with the individualized biometric data of the first class to form a plurality of interrogation database identification hashes; c) compare each of the plurality of interrogation database identification hashes to the individualized identification hash; and d) report whether a match of any of the plurality of database identification hashes to the first individualized identification hash is identified.

In a further aspect, the invention provides a method of enrolling an individual in a system for identification, comprising the steps of: a) acquiring individualized identification of the individual comprising individualized biometric data of at least a first and a second class from the individual; b) converting the individualized biometric data of the first class into a digital electronic format; c) storing a first instance of the digitized individualized biometric data of the first class; d) converting the individualized biometric data of the second class into a digital electronic format; e) hashing a second instance of the digitized individualized biometric data of the first class with the digitized individualized biometric data of the second class to form a first individualized identification hash; and f) storing the first individualized identification hash. In some embodiments, the first individualized identification hash may be a one way hash. The method may further include the steps of: a) acquiring a third or more class of individualized biometric data; b) converting each of the third or more class of individualized biometric data to a digital electronic format; and c) storing each of the third or more class of digitized individualized biometric data. The method may further include the steps of: a) converting a second instance of the digitized individualized biometric data of the second class into a plurality of digitized individualized biometric data of the second class; b) hashing a second instance of the digitized individualized biometric data of the first class with each of the plurality of digitized individualized biometric data of the second class to form a plurality of partial individualized identification hashes; and c) storing the plurality of partial individualized identification hashes. The method may further include the steps of: a) assigning an enrollment verification certification; and b) storing an enrollment verification certification. The method may include storing the individualized identification information of the individual on an identification card.

In another aspect, the invention provides a method of producing the identification card of an individual, including the steps of: a) acquiring individualized identification of the individual comprising digitized individualized biometric data of at least a first class and a second class from the individual; b) storing a first instance of the digitized biometric data of the first class on the identification card; c) converting the individualized biometric data of the second class into a digital electronic format; d) hashing a second instance of the digitized individualized biometric data of the first class with the digitized biometric data of the second class to form a first individualized identification hash; and e) storing the first individualized identification hash on the identification card. In some embodiments, the individualized identification hash may be a one way hash. The method may further include the steps of: a) acquiring individualized identification comprising a third or more class of digitized individualized biometric data; and b) storing each of the third or more class of digitized individualized biometric data. The method may further include the steps of: a) converting a second instance of the digitized individualized biometric data of the second class into a plurality of digitized individualized biometric data of the second class; b) hashing a second instance of the digitized individualized biometric data of the first class with each of the plurality of digitized individualized biometric data of the second class to form a plurality of partial individualized identification hashes; and c) storing the plurality of partial individualized identification hashes. The method may further include the step of storing an enrollment verification certification on the identification card.

According to another exemplary embodiment of the invention, there is provided a system for determining an identity of a person, including an identification card which includes individualized identification information containing individualized biometric data of at least a first class and individualized biometric data of a second class, wherein the individualized biometric data of the first class and the individualized biometric data of the second class are hashed together to form an individualized identification hash; and a processor configured to: a) connect to at least one interrogation database comprising a plurality of interrogation biometric data of the second class wherein each of the plurality of interrogation biometric data of the second class has an interrogation database identifier; b) interrogate the at least one interrogation database wherein each of the plurality of interrogation biometric data of the second class is hashed together with individualized biometric data of the first class to form a plurality of interrogation database identification hashes; c) compare each of the plurality of interrogation database identification hashes to the individualized identification hash; and d) report a match of the database identification hash to the individualized identification hash. The individualized biometric data of the first class may be a fingerprint data or a retinal scan data. The individualized biometric data of the second class may be a DNA data. When the individualized biometric data of the second class is a DNA data, it may be a STR profile. Alternatively, the DNA data may be a SNP profile. In other embodiments, the DNA data may be an INDEL profile. In some embodiments of the system, the individualized biometric data further includes a third class of individualized biometric data. The system may provide an identification card wherein when a class of individualized biometric data is a DNA data, then the DNA individualized biometric data is present on the identification card in a hashed form. In some embodiments, the DNA individualized biometric data present as a hashed form may be a one way hash. In some embodiments, the individualized identification hash stored on the identification card is a graphical representation. In various embodiments of the system, the individualized identification hash on the identification card may be a barcode. In other embodiments, the individualized identification hash is an alphanumeric representation.

The processor of the system may be further configured to: a) read the first class of individualized biometric data at a point of contact; and b) confirm the first class of individualized biometric data at the point of contact. In yet other embodiments, when a third class of individualized biometric data is provided on the identification card, the processor is further configured to read the third class of individualized biometric data at the point of contact; and confirm the third class of individualized biometric data at the point of contact. In other embodiments, the processor is further configured to retrieve an enrollment verification certification from the identification card; and interrogate an enrollment database to verify the authenticity of the identification card. In some embodiments of the system, the system may further include a) a biometrics acquisition component configured to acquire individualized biometric data of at least a first and a second class from the individual; and b) a processor configured to i) convert the individualized biometric data of the first class into a digital electronic format; ii) store a first instance of the digitized individualized biometric data of the first class on the identification card; iii) convert the individualized biometric data of the second class into a digital electronic format; iv) hash a second instance of the digitized individualized biometric data of the first class with the digitized individualized biometric data of the second class to form an individualized identification hash; and v) store the individualized identification hash on the identification card. In some embodiments, the system also includes at least one interrogation database. In other embodiments, the system includes an enrollment database.

According to another exemplary embodiment of the invention, there is provided an identification card configured to operate in the system for determining an identity of a person. The identification card may include individualized biometric data of at least a first class and individualized biometric data of a second class, where the individualized biometric data of the first class and the individualized biometric data of the second class may be hashed together to form an individualized identification hash. In some embodiments, the individualized identification hash may be formed using a one-way hash. The identification card may include the individualized biometric data of the first class stored separately from the individualized identification hash. The identification card may include individualized biometric data of the first class including a fingerprint data or a retinal scan data. The identification card may include individualized biometric data of the second class including a DNA data. In some embodiments, the individualized biometric data of the second class may be a STR profile. In yet other embodiments, the individualized biometric data of the second class may be a SNP profile. In other embodiments, the individualized biometric data of the second class may be an INDEL profile. An identification card is provided that may also include individualized biometric data including a third class of individualized biometric data. In some embodiments when the identification card includes three classes of individualized biometric data, the individualized biometric data of the third class may include a DNA data. An identification card according to the invention is provided where when a class of individualized biometric data is a DNA data, then the DNA biometric data is present on the identification card in a hashed form. In some embodiments, the hash is a one way hash.

According to another exemplary embodiment of the invention, there is provided a method of identifying an individual including a) retrieving an individualized identification hash stored on an identification card of the individual wherein the individualized identification hash is formed from individualized biometric data of a first class and individualized biometric data of a second class; b) retrieving an individualized biometric data of the first class stored on the identification card; c) accessing at least one interrogation database comprising a plurality of interrogation biometric data of the second class wherein each of the plurality of interrogation biometric data of the second class has an interrogation database identifier; d) hashing each of the plurality of interrogation biometric data of the second class together with the individualized biometric data of the first class to form a plurality of interrogation database identification hashes; comparing each of the plurality of interrogation database identification hashes to the individualized identification hash; and e) reporting whether a match of the database identification hash to the individualized identification hash is identified. In some embodiments, the method may include the steps of a) reading the first class of individualized biometric data at a point of contact; and b) confirming the first class of individualized biometric data at the point of contact. In some embodiments, the individualized biometric data of the first class stored on the identification card may be a fingerprint data or a retinal scan data. In other embodiments, the individualized biometric data of the second class may be a DNA data. In some embodiments the DNA data may be a STR profile. In some embodiments, when a class of individualized biometric data is a DNA data, then the DNA biometric data may be present on the identification card in a hashed form. In other embodiments, when the DNA biometric data is present on the identification card in a hashed form, it is a one way hash. In some embodiments, the individualized biometric data of the first class may be a retinal scan data. The method according to the invention may also provide wherein the individualized biometric data may further include a third class of individualized biometric data. In some embodiments, when the individualized biometric data includes three classes of individualized biometric data, the processor may be further configured to a) read the third class of individualized biometric data at the point of contact; and b) confirm the third class of individualized biometric data at the point of contact. The method according to the invention may also include the steps of a) retrieving an enrollment verification certification from the identification card; b) accessing an enrollment database; and c) determining whether the enrollment verification certification is valid.

According to another exemplary embodiment of the invention, there is provided a method of enrolling an individual in a system for identification, including the steps of a) acquiring individualized biometric data of at least a first and a second class from the individual; b) converting the individualized biometric data of the first class into a digital electronic format; c) storing a first instance of the digitized individualized biometric data of the first class on an identification card; d) converting the individualized biometric data of the second class into a digital electronic format; e) hashing a second instance of the digitized individualized biometric data of the first class with the digitized individualized biometric data of the second class to form an individualized identification hash; and f) storing the individualized identification hash on the identification card.

According to yet another exemplary embodiment of the invention, there is provided a computer readable medium including computer readable instructions, which, when executed by a computer in communication with an identification card including an individualized biometric data of a first class and an individualized identification hash formed from the individualized biometric data of the first class and an individualized biometric data of a second class, is configured to a) connect with at least one interrogation database comprising a plurality of interrogation biometric data of the second class wherein each of the plurality of interrogation biometric data of the second class has an interrogation database identifier; b) interrogate the at least one interrogation database wherein each of the plurality of interrogation biometric data of the second class is hashed together with the individualized biometric data of the first class to form a plurality of interrogation database identification hashes; c) compare each of the plurality of interrogation database identification hashes to the individualized identification hash; and d) report a match of the database identification hash to the individualized identification hash In some embodiments, wherein the computer may be configured to a) read the first class of individualized biometric data at a point of contact; and b) confirm the first class of individualized biometric data at the point of contact. In some embodiments, the individualized biometric data of the first class may be a fingerprint data or a retinal scan data. In other embodiments, the individualized biometric data of the second class may be a DNA data. In some embodiments, the individualized biometric data of the second class may be a STR profile. In some embodiments, the individualized biometric data of the first class may be a retinal scan data. In some embodiments of the computer readable medium of the invention, the individualized biometric data may include a third class of individualized biometric data. In some embodiments, the third class of individualized biometric data may be a DNA data. In some embodiments, the third class of individualized biometric data may be a STR profile. In some embodiments of the computer readable medium when the individualized biometric data includes a third class of individualized biometric data, the computer may be further instructed to a) read the third class of individualized biometric data at the point of contact; and b) confirm the third class of individualized biometric data at the point of contact.

According to yet another exemplary embodiment of the invention, there is provided a computer readable medium including computer readable instructions, which when executed by a computer in communication with a biometrics acquisition component, is configured to a) acquire individualized biometric data of at least a first and a second class from an individual; b) convert the individualized biometric data of the first class into a digital electronic format; c) store a first instance of the digitized individualized biometric data of the first class on an identification card; d) convert the individualized biometric data of the second class into a digital electronic format; e) hash a second instance of the digitized individualized biometric data of the first class with the digitized individualized biometric data of the second class to form an individualized identification hash; and f) store the individualized identification hash on the identification card.

Additional objects and embodiments of the invention may be set forth in or flow from the following description, and may in part be evident from the description, or may be learned by practice of the invention. The objects of the invention will be realized and attained by means of the elements and combinations particularly pointed out in the appended claims.

It is to be understood that both the foregoing general description and the following detailed description are exemplary and explanatory only and are not in any way restrictive of the present invention.

BRIEF DESCRIPTION OF THE DRAWINGS

FIG. 2A-2 is a schematic representation of an embodiment of the identification system of the present invention.

FIG. 2B-1 is a schematic representation of an embodiment of the identification system of the present invention.

FIG. 2B-2 is a schematic representation of an embodiment of the identification system of the present invention.

Figure 1A:
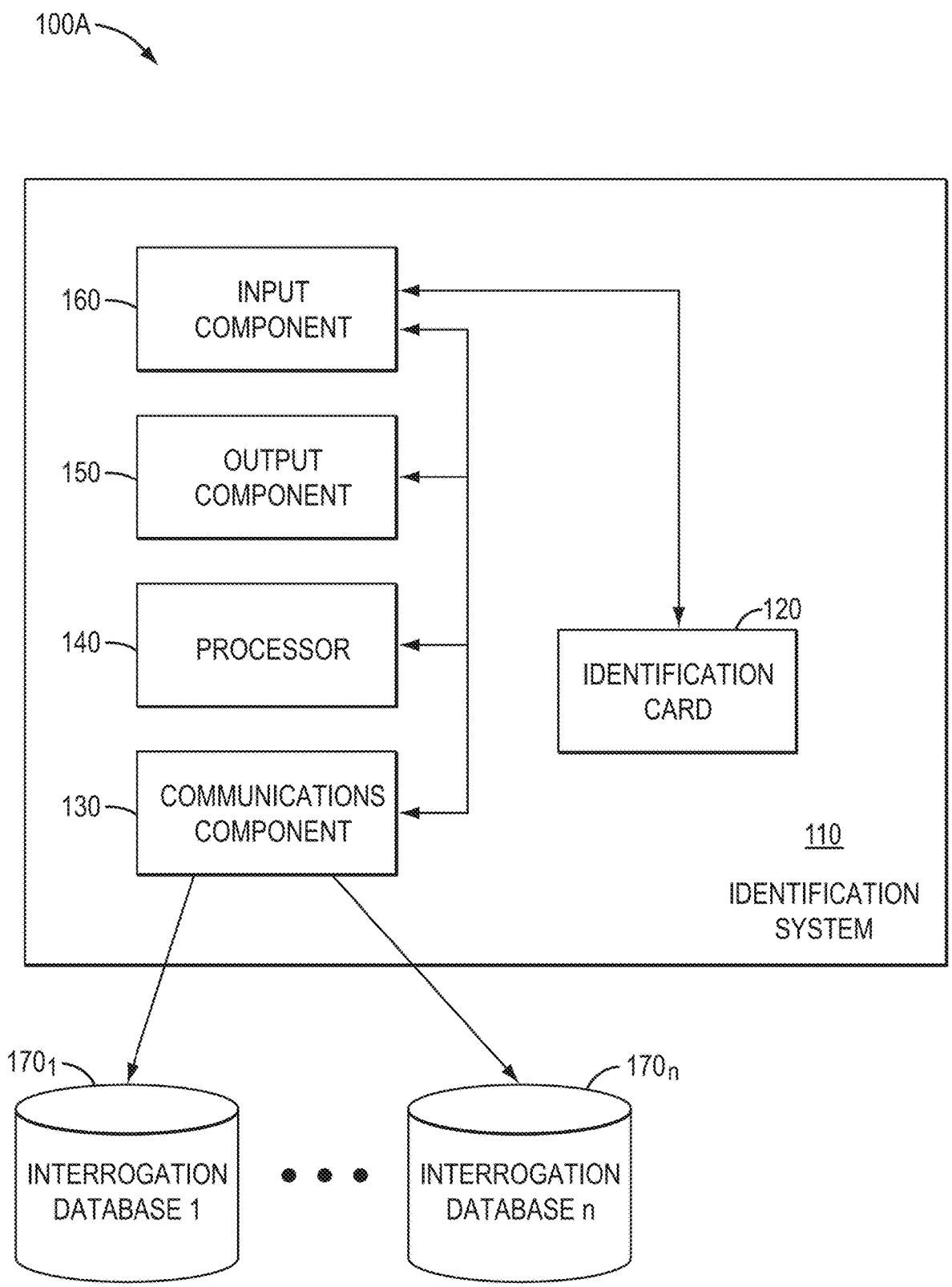
FIG. 1A is a schematic representation of one embodiment of the identification system of the present invention.

It is to be understood that the figures are not drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the last two digits of reference numbers will be used throughout the drawings to refer to the same or like parts.

DESCRIPTION OF VARIOUS EXEMPLARY EMBODIMENTS

The section headings used herein are for organizational purposes only and are not to be construed as limiting the described subject matter in any way. When definitions of terms in incorporated references appear to differ from the definitions provided in the present teachings, the definition provided in the present teachings shall control. It will be appreciated that there is an implied "about" prior to the values discussed in the present description, such that slight and insubstantial deviations are within the scope of the present teachings. In this application, the use of the singular includes the plural unless specifically stated otherwise. Also, the use of "comprise", "comprises", "comprising", "contain", "contains", "containing", "have", "having", "include", "includes", and "including" are not intended to be limiting.

Repeated usage of the phrase "in one embodiment" does not necessarily limit to usage to that same embodiment, although it may.

Unless otherwise defined, scientific and technical terms used in connection with the present teachings described herein shall have the meanings that are commonly understood by those of ordinary skill in the art. Generally, nomenclatures utilized in connection with, and techniques of, molecular biology, and oligo- or polynucleotide chemistry and amplification and detection thereof described herein are those well known and commonly used in the art.

"Access to an entity, transport, information, location, security organization, law enforcement organization, transaction, services, authorized status, funds, and the like" may include an entity such as a sovereign nation; restricted zone; an executive board; committee or governance body; private or public institution with controlled access, to name a few non-limiting examples. "Information" as used in this context refers to information which may have security, privacy or distribution controls placed upon it. "Transport" as referred to in this context, includes but is not limited to air, rail, automobile, or marine transportation modes. "Location" as referred to in this context, includes but is not limited to a geopolitical region, a private facility or grounds, a controlled access portion of a work or education facility. "Security organization" as referred to in this context refers to an intelligence community, an intelligence organization, and other threat sensitive organizations, both governmental and nongovernmental. "Law enforcement organization" as referred to in this context refers to local, state, federal, military or international police or investigative force. Access to law enforcement organization can include gaining authorized status as an employee or consultant. Access to law enforcement organization can also include detainee processing or arraignment testing as individuals suspected of being high risk are processed into a law enforcement or security organization. "Transaction" as referred to in this context, includes but is not limited to financial transactions, including but not limited to banking, purchase of airline tickets, exercise of voting franchise, and purchase of controlled access materials including firearms, alcohol, and medications. "Services" as referred to in this context, includes but is not limited to banking services, healthcare services, governmental benefit services, and the like. "Authorized status" as referred to in this context, includes but is not limited to a high security position within intelligence, security, law enforcement, and other threat sensitive organizations, threat assessment at the time of enrollment in the identification systems of the invention, including but not limited to assessment against known criminal, terrorist, and suspect databases, gun permit, drivers license, voter registration, government benefits registration, explosives certification, hazardous chemical handling certification, pilot license, commercial transportation license including but not limited to bus and trucking commercial licenses, radioactive materials handling certification, transportation worker credentials, working rights authorization including but not limited to permanent resident status, temporary worker status visas, and clearance for work permits in construction, transport and other security-sensitive work areas, national entry visas, including tourist or long term visitor, and the like. "Funds" as referred to in this context, includes cash, cash equivalents, credit and the like.

"Biometric data" as used herein, refers to data related to physiological aspects of an individual and may include skin recognition, including but not limited to fingerprints and palmprints; body geometry features, including but not limited to ear, hand, finger, and the like; facial features; face images; voice; voice prints; optical recognition, including but not limited to iris scans and retinal scans; signatures; blood typing; nucleic acid profiles, including deoxyribonucleotide (DNA) profiles and ribonucleic acid (RNA) profiles; protein assays; infrared identification, including but not limited to face, hand, and handvein; and the like. One or more of these may be used in any combination. In addition to any of the biometric data described in the previous sentence, biometric data may include gait recognition, which may be used alone or in any combination with other biometric data.

DNA data include but are not limited to Short Tandem Repeat (STR); Single Nucleotide polymorphism (SNP); Insert and Deletion (INDEL) sequences; Alu elements and other non-STR repeat sequences. In some embodiments, the DNA data is any polymorphic DNA sequence that can be used for human identification.

STR profile: Common sets of short tandem repeat (STR) markers or "core loci" permits equivalent genetic information to be shared and compared. These core STR loci occur in between genes where a high degree of variability is tolerated and are thus not directly responsible for physical traits or genetic diseases. The "core loci" are often used in human identity testing such as parentage testing and missing persons and mass disaster investigations, as well as for entry of DNA genotype data into national or international databases used to link serial crimes and offenders. Presently, the FBI has generated 13 core STR loci as the basis for the genetic fingerprinting of an individual and maintains a database of such information for later reference. Other international organizations focus on different, but overlapping sets of STR loci, as shown in TABLE 1. STR loci that may be tested include one of more of the following loci: DYS456, DYS389I, DSY390, DYS 389II, DYS458, DYS19, DSY385, DYS393, DYS391, DYS439, DYs635, DYS392, Y_GATA_H4, DYS437, DYS438, DYS448, D13S317, D12S391, D22S1045. DYF387S1, DYF399S1, DYF403S1, DYF404S1, DYS449, DYS518, DYS526, DYS547, DYS570, DYS576, DYS612, DYS626, DYS627, D21S1, Penta E, and Penta D. One of skill can determine that additional loci may be useful to add to a STR profile, and the listing herein is by no means limiting. Many commercially available kits may used to generate a STR profile from a biological sample, including but not limited to AmpFLSTR® kits (including any of Identifiler®, Identifiler®Plus, Identifiler®Direct, Yfiler®, Minifiler™, NGM™, NGM SElect™, Profiler®, Profiler Plus®, Profiler Plus 10, COfiler®, SGM Plus®, SEfiler Plus™ from Applied Biosystems®), Investigator Quantiplex HYres kits from Qiagen, and PowerPlex® kits from Promega.

TABLE 1

| | |
|---|---|
| US Core loci | CSF1PO; FGA; TH01; TPOX; VWA; D3S1358; D5S818; D7S820; D8S1179; D13S317; D16S539; D18S51; D2S11; and Amelogenin. |
| Extended European Standard Set (ESS) | FGA; TH01; VWA; D1S1656; D2S441; D3S1358; D8S1179; D10S1248; D18S51; D21S11, and D22S1045. |
| European Additional Loci | D2S1338; D16S539; D19S433; SE33; and Amelogenin. |
| UK Core Loci | FGA; TH01; VWA; D2S1338; D3S1358; D8S1179; D16S539; D18S51; D19S433; D2S11; and Amelogenin. |
| German Core Loci | FGA; TH01; SE33; VWA; D3S1358; D8S1179; D18S51; D2S11; and Amelogenin. |
| Interpol Standard set of Loci | FGA; TH01; VWA; D3S1358; D8S1179; D18S51; D2S11; and optionally, Amelogenin. |

SNP profile: Single nucleotide variants in a DNA sequence may be in coding, noncoding or intergenic regions of genes, differing between members of a biological species or between paired chromosomes of an individual. Some SNP sequences may be related to phenotypic characteristics of an individual. This data may be of particular use if attempting to interrogate data where there is incomplete personal information for a biometric data set.

INDEL profile: Insertion and deletion sequences include the following types of insertion/deletions: insertions or deletions of single base pairs; expansions by only one base pair (monomeric base pair expansions); multi-base pair expansions of about 2 to about 15 repeats; transposon insertions (insertions of mobile elements); and random DNA sequence insertions or deletions.

Alu element: Alu elements are mobile and repetitive elements in the human genome. Alu elements are generally about 300 bp and are considered as a short interspersed element (SINE) within the broad class of repetitive DNA elements. Derived from the small cytoplasmic 7SL RNA, these inserted elements are interspersed throughout the genome. About 7,000 Alu elements are unique to humans, and some may result in disease. Alu elements are useful in human identification as Alu element insertion events have characteristic signatures and reveal details of ancestry and relatedness.

Biometric Acquisition. There are numerous vendors of biometric acquisition instrumentation that may be used for the enrollment, verification and authentication aspects of the identification system and methods of the invention. Vendors include but are not limited to Biometric Information Management, Biometric4all, Cogent Systems, Inc., CrossMatch Technologies, Inc., Dataworks Plus, First Advantage, Fulcrum Biometrics LLC, Futronic Technology Co. Ltd., Identix Incorporated, Innovative Biometric Systems., Logitech, Morphotrak Biometric Solutions, NEC, Sagem, Telos ID, and the like.

Biometric Digitization. A wide variety of conversion algorithms to provide a digitized representation of each type of biometric data is possible. Many of the biometric acquisition vendors include software development kits (SDKs) with instrumentation and other SDKs may be available from sources other than the instrumentation manufacturer.

A non-limiting example of fingerprint acquisition and digitization may utilize a fingerprint scanner such as are provided by Futronic Technology Co. Ltd and one possible fingerprint extraction SDK is Verifinger SDK 6.4 from Neurotechnology, where the SDK includes Source Code, Documentation, and Demo Applications. In some embodiments, the digitized fingerprint scan data conforms to the ANSI/NIST digitization standard. The digitization may also conform to the FBI/AFIS standards. Iris scanning and digitization includes but is not limited to an I SCAN™ 2, a dual iris capture scanner from Crossmatch Technologies, which includes SDK software to enable image finding and stabilization, pupil segmentation and produces an iris image meeting format specifications of the ANSI INCITS 379-2004 and ISO/IEC 19794-6 standards. Facial recognition scanning may be accomplished by a number of devices including but not limited to QuickCam Orbit AF from Logitech. Either the iris scan data or the facial recognition scan data may be extracted using Verifinger SDK 6.4 from Neurotechnology.

"Hash", "hashed" or "hashing" as used herein, refers to data transformation which converts variable sized data to another representation. "Hash" as used herein, includes usage as both verb and noun forms. For example, a hash can be the representation resulting from the data transformation. The representation may be of fixed data size, same data size, different data size or variable data size. The representation may be of the same data type or another data type, including but not limited to numerical, alphabetical, graphical, or audio. The graphical representation may be pictorial or schematic, including but not limited to a barcode representation. The representation may be encrypted. The encrypted representation may be invertible with or without a key, or the encrypted representation may be encrypted one-way.

Many forms of data transformation are useful in this invention. In some of the embodiments of the invention, the hashing produces the same end value for a given input data every time the hash is produced. The hashing also provides unique values for unique input, thus providing uniform distribution of the hash values within a potential range, and preventing differing input biometric data from mapping to the same hash value. One of skill can determine other data manipulation that may be useful for storage of the hash values as enrollment databases enlarge.

Some useful cryptographic hash functions include BLAKE-256, BLAKE-512, ECOH, FSB, GOST, Grøstl, HAS-160, HAVAL, JH, Keccak, MD2, MD4, MD5, MD6, RadioGatún, RIPEMD-64, RIPEMD-160, RIPEMD-320, SHA-0, SHA-1, SHA-224, SHA-256, SHA-384, SHA-512, Skein, Snefru, Spectral Hash, SWIFFT, Tiger, and Whirlpool.

An additional level of data transformation may be used to verify data integrity and to authenticate the hash values represented on an identification card of the invention. A Hash-based Message Authentication Code (HMAC) may be used to combine the cryptographic hash functions described above with a secret key. One definition of the HMAC algorithm from a source, RFC 2014 code, defines the algorithm as follows:

H(•) is a cryptographic hash function.

K is a secret key, for example, padded to the right with extra zeros to the input block size of the hash function, or the hash of the original key if it is longer than that block size;

m is the message to be authenticated;

∥ denotes concatenation;

⊕ denotes exclusive or (XOR);

opad is the outer padding (0x5c5c5c . . . 5c5c, one-block-long hexadecimal constant);

ipad is the inner padding (0x363636 . . . 3636, one-block-long hexadecimal constant).

Then HMAC(K,m) can be mathematically defined as: HMAC(K,m)=H((K⊕pad)∥H((K⊕ipad)∥m)), in one non-limiting example. The cryptographic strength of the HMAC depends upon the size of the secret key that is used. The most common attack against HMACs is brute force to uncover the secret key. HMACs are substantially less affected by independent values mapping to the same hash values, i.e. collisions, than their underlying hashing algorithms alone. Therefore, HMAC-MD5 does not suffer from the same weaknesses that have been found in MD5, for example.

Hashing methods allowing some degree of dissimilarity while still finding identity between two substantially similar files are widely available and are often referred to as fuzzy hash functions. Context triggered piecewise hashing is one method of matching not quite identical sets of bits of information. An example of such a method combines a rolling hash with a piecewise hash, as devised by Kornblum (Kornblum, Digital Investigation 3S (2006), pp S91-S97). Other fuzzy hashing tools include ssdeep and deeptoad. Additionally, fuzzy hash algorithms are disclosed in U.S. Patent Application Publications 2011/0093426 and 2011/0067108 (Hoglund), for classifying data objects including DNA sequences.

In some embodiments of the invention, hashing methods are used that allow a predetermined degree of dissimilarity when comparing two hashes for identity. Even a small change, for example, in orientation of a fingerprint scan, may provide a digitized form that yields a different hash from a different fingerprint scan taken from the same finger at a different time, location or after a degree of physiological modification. These hashing methods can be useful when differences in the source or target biometric data do not provide an exact match but do possess a degree of similarity high enough for a positive identification. Therefore, the processor may be instructed to not require perfect identity to signal a match. DNA profiles may also demonstrate some dissimilarity upon hashing, but still be capable of being detected by the processor as representing a reasonable match. Allowing some degree of dissimilarity while still determining that a match has been identified, can initiate a further inquiry into the identity of the individual presenting the identification card.

"Identification card" as used herein, includes but is not limited to documents, magnetic disks, magnetically encoded cards, credit cards, bank cards, phone cards, stored value cards, prepaid cards, smart cards (e.g., cards that include one or more semiconductor chips, such as memory devices, microprocessors, and microcontrollers), contact cards, contactless cards, proximity cards (e.g., radio frequency (RFID) cards), passports, driver's licenses, network access cards, employee badges, debit cards, security cards, visas, immigration documentation, national ID cards, citizenship cards, social security cards, security badges, certificates, including but not limited to explosives certification, hazardous chemical transport, radioactive materials handing and/or transport), voter registration and/or identification cards, police ID cards, border crossing cards, security clearance badges and cards, legal instruments, gun permits, badges, gift certificates or cards, membership cards or badges, and tags. In some embodiments, the identification card may alternatively be incorporated into another device such as a cell phone, pager, wrist watch, computer, thumb drive, tablet device (e.g., iPad™ or), personal digital assistant such as a Blackberry™, key fob, or other commonly available electronic device. Such cards can include technology to prevent counterfeiting such as incorporation of holograms, fluorescent inks, quantum dots, or other techniques. In addition to any of the identification cards described in the preceding sentence, an identification card may also include a near field communication (NFC) card.

As shown by the description above, the identification card may have the physical form of a card or may be an electronic representation. The card, when it is an electronic representation, does not have to have a physical form separate from the device carrying the information comprising the identification card as described in the following sections. An electronic representation of the identification may also have some or none of the information physically stored on the physical device presented by the individual. Any, some or all of the information may be stored in an enrollment database or other database remote from the point of contact and accessed upon presentation of the identification card. When the identification card does not store the identification information on the card, any or all of the information may be accessed by a password or other electronic entry permission granting procedure. As used herein, "stored on the identification card" refers to either information physically stored on the card in any suitable medium or to information accessible as described above upon presentation of the identification card. The description also uses the terms such as "secure," "protected," "encrypted," "authenticated," etc. These terms refer to a given level of security, protection, authenticity, etc.

The term "report" as used herein includes information or directives related to the outcome of the comparison between biometric data of the individual as presented at a point of contact, biometric data of an interrogation database, biometric data of the individual as enrolled in the system, and biometric data obtained from the individual at the point of contact. A report by the processor includes issuing a conclusion whether the biometric data of the individual matches biometric data of an entry in an interrogation database, and may include a directive to further investigate the relationship between the individual and the known or unknown person from whom the biometric data in the interrogation database was obtained. In some embodiments, when at least one partial individualized identification hash of the individual matches a partial interrogation database identification hash, the report may include the percentage of alleles matched data, and number of loci compared. This report may also issue a conclusion that a less stringently defined association has been found between the interrogation database entry and the individual presenting the identification card. The computer program may further instruct the processor to issue a conclusion indicating a potential familial connection. A directive may be included in the report to further investigate the relationship between the individual and the partially matching biometric data of the interrogation database. A report by the processor includes issuing a conclusion whether the biometric data of the individual obtained at the point of contact matches the biometric data obtained from the individual at the time of enrollment and stored on an identification card and/or other databases. This report may include the directive to further investigate the credentials of the individual if no match is reported. A report by the processor includes issuing a conclusion whether an enrollment verification certification stored on the identification card presented by the individual is authentic and matches the enrollment verification certification assigned at the time of enrollment of the individual, which may be stored in an enrollment database or other accessible database. This report may include the directive to further investigate the credentials of the individual if no match is reported.

Any of the reports described above may also include issuance of a report, in an electronic or other suitable medium, to an external authority, such as for instance a law enforcement agency, immigration control agency, airport security personnel, and licensing authority, and the like, requiring further investigation of the match or lack of match. In some embodiments, the security agency is a governmental agency. Non-limiting examples of a directive included in a report is denial of the request by the individual for access to an entity, transport, information, location, transaction, services, authorized status, or funds, and/or a requirement to detain the individual at the point of contact until further investigation is made or another authority assumes control of the investigation.

There are numerous situations where an individual is required to provide an identification card in order to be granted access to an entity, transport, information, location, security organization, law enforcement organization, transaction, services, authorized status, funds, and the like. However, in many instances, for example, at a border control point or an airport security point, simple comparison of the name of the individual to a list of high-risk individuals who are deemed to be not suitable for admission to that national entity, does little to prevent acts of violence and/or terrorism. Individuals may present easily forged or fake personal identification and identical names may falsely label an innocent person as a high risk individual. Biometric data has been used to verify an individual's identity, including systems where an individual is previously enrolled by submitting biometric data for incorporation into a central database, for comparison, upon presentation of an identification card issued therefrom at a later date, to validate that individual's identity as that of the enrolled individual. This process, too, falls short of identifying persons, who may be known to other organizations as individuals previously implicated in violence or terrorism. Simple comparison of the biometric data incorporated in the identification card to the database does not prevent the use of stolen or faked biometric data combined with true personal identification such as a photograph as there is no real time crosscheck of the match between the person presenting the card and the information incorporated in the identification card.

None of these systems will identify an individual who may have participated in an act of violence or terrorism previously without additionally encompassing innocent individuals who have some characteristics in common, such as name or physical description.

Additionally, while biometric data are useful personal identifiers, it is also desirable to prevent unauthorized access or theft of such data. Unlike passwords and the like, individualized biometric data cannot be revoked and reissued after a breach of security.

There are a number of databases being managed and developed by agencies who gather evidence from attempted or successful acts of violence and terrorism, which include biometric data including, without limitation, fingerprints, voice recordings, DNA samples from which DNA data may be developed, and the like, which are entered into the database.

It is of interest to be able to interrogate these databases to identify individuals who may request access to an entity, transport, information, location, transaction, services, authorized status, funds, and the like, but who may be at high risk of attempting acts of violence or terrorism. Additionally, it would be useful to definitively verify the identity of an individual who is legitimately requesting access to an entity, transport, information, location, transaction, services, authorized status, funds, and the like.

As described herein, comparison of interrogation database biometric data containing DNA data with individualized identification information of an individual comprising DNA data is made using only hashed data to preserve the security and privacy of the DNA data of the individual. For example, a first and a second class of individualized biometric data are hashed and at least a first individualized identification hash so formed is stored for later retrieval and use in the system of identification described herein. A second instance of the individualized biometric data of the first class is hashed with each of a plurality of interrogation database biometric data to form a plurality of interrogation database identification hashes. At least a first individualized identification hash is compared with each of the plurality of interrogation database identification hashes, and any matches are reported. Since the second class of individualized biometric data, for example, DNA data, is not retrieved or compared unhashed, a higher level of privacy and security of the individualized biometric data of the second class is maintained. An individual has a decreased risk of improper access or use of their biometric information. This additional level of privacy is provided even while providing for identification of high risk individuals who may only be known by biometric data left at a scene of attempted violence or terrorism. For example, a DNA data may have been obtained from a DNA sample taken from a surface or an object analyzed by investigators. Alternatively, a fingerprint may have been obtained from an object under investigation by law enforcement or other agencies. There may be no other identifier available for such data, which may represent a high risk individual who should be intercepted upon attempting to access to an entity, transport, information, location, transaction, services, authorized status, funds, and the like from a point of contact. The system according to the present invention may identify such a high risk individual without having that individual's name, or may identify an individual who has sufficient relatedness to lead to positive identification of a high risk individual. Once such a match is reported, further investigation can be made to determine whether the individual may continue in the process to obtain access to the entity, transport, information, location, transaction, services, authorized status, and/or funds requested.

Additionally, the invention may also provide for a confirmation of at least one of the individualized biometric data at the point of contact. This provides verification that the individual presenting an identification card is indeed the individual from which the biometric data has been obtained.

System of Identification.

A system of identification is described, therefore, for determining an identity of a person, which includes a processor that retrieves and compares individualized biometric data with interrogation database biometric data in at least one interrogation database, wherein the processor reports whether a match has been found. The system may include computer readable media which is in communication with the processor and instructs the processor to perform the processes described herein. The system may also include an identification card containing individualized identification information and a processor. In some embodiments the identification system is configured to connect to at least one interrogation database. In other embodiments, the system is configured to connect to more than one interrogation database. In yet other embodiments, the system further includes at least one interrogation database. The system may also include one or more output components and/or one or more input components. The system may additionally include a verification component. The verification component may include one or more biometric data acquisition and data processing components. In another aspect, the invention provides an enrollment component. The enrollment component may include one or more biometric data acquisition components and one or more data processing components. In some embodiments of the invention, the identification system includes the enrollment component. Exemplary systems of the invention are shown in FIGS. 1A-3B, and the individual components described in the following sections below.

Figure 1B:
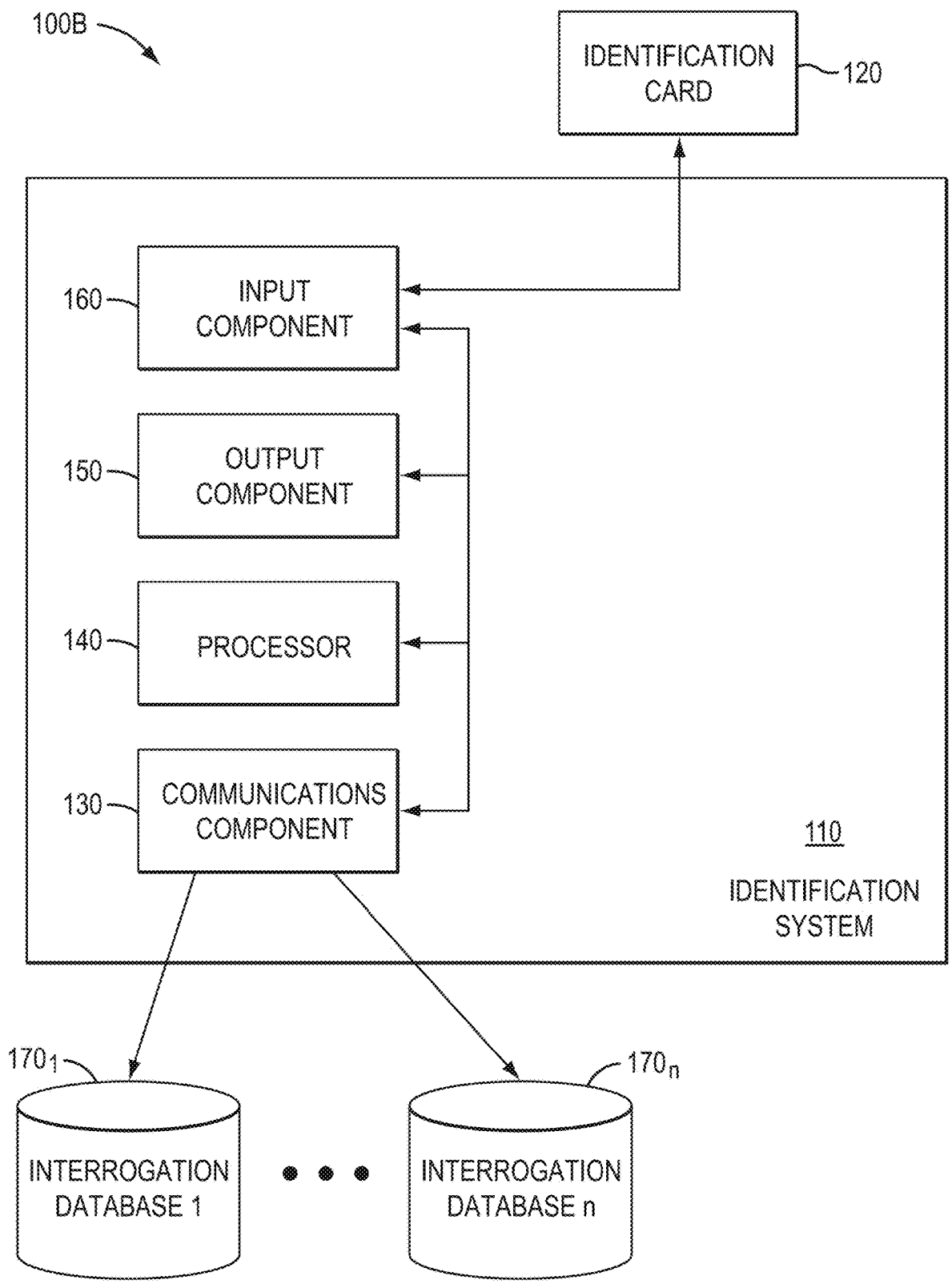
FIG. 1B is a schematic representation of one embodiment of the identification system of the present invention.

FIGS. 1A and 1B show embodiments 100A and 100B respectively, of the identification system 110 of the invention. In the embodiment of FIG. 1A, the identification card 120 is part of the identification system. In the embodiment of FIG. 1B, the identification system 110 does not include the identification card 120. The identification system 110 includes an identification card 120 configured to be read by the input component 160, which relays individualized information comprising individualized biometric data to the processor 140. In a variation of these embodiments, the identification system obtains the individualized information from another database or repository, and the input component 160 relays the individualized information to the processor 140. The processor 140 communicates via the communication component 130 to interrogation databases $170_1$ to $170_n$, to retrieve a plurality of interrogation database biometric data. The processor 140 interrogates the plurality of interrogation database biometric data and compares it to one or more individualized identification hashes and/or a plurality of partial individualized identification hashes. A report is made by the processor 140 regarding whether or not a match is found via the output component 150.

Figures 1, 2A:
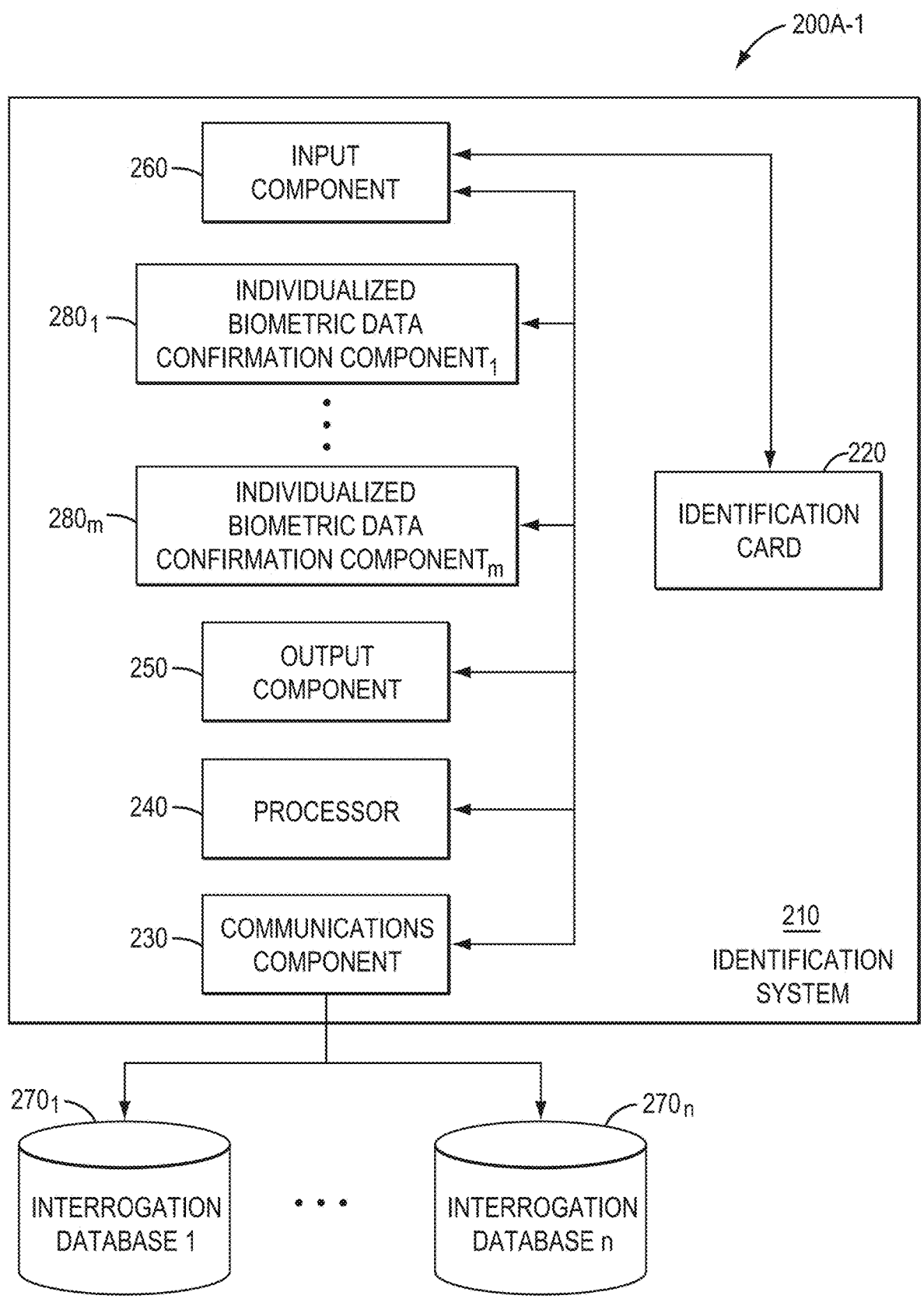
FIG. 2A-1 is a schematic representation of an embodiment of the identification system of the present invention.
Figures 2, 2A:
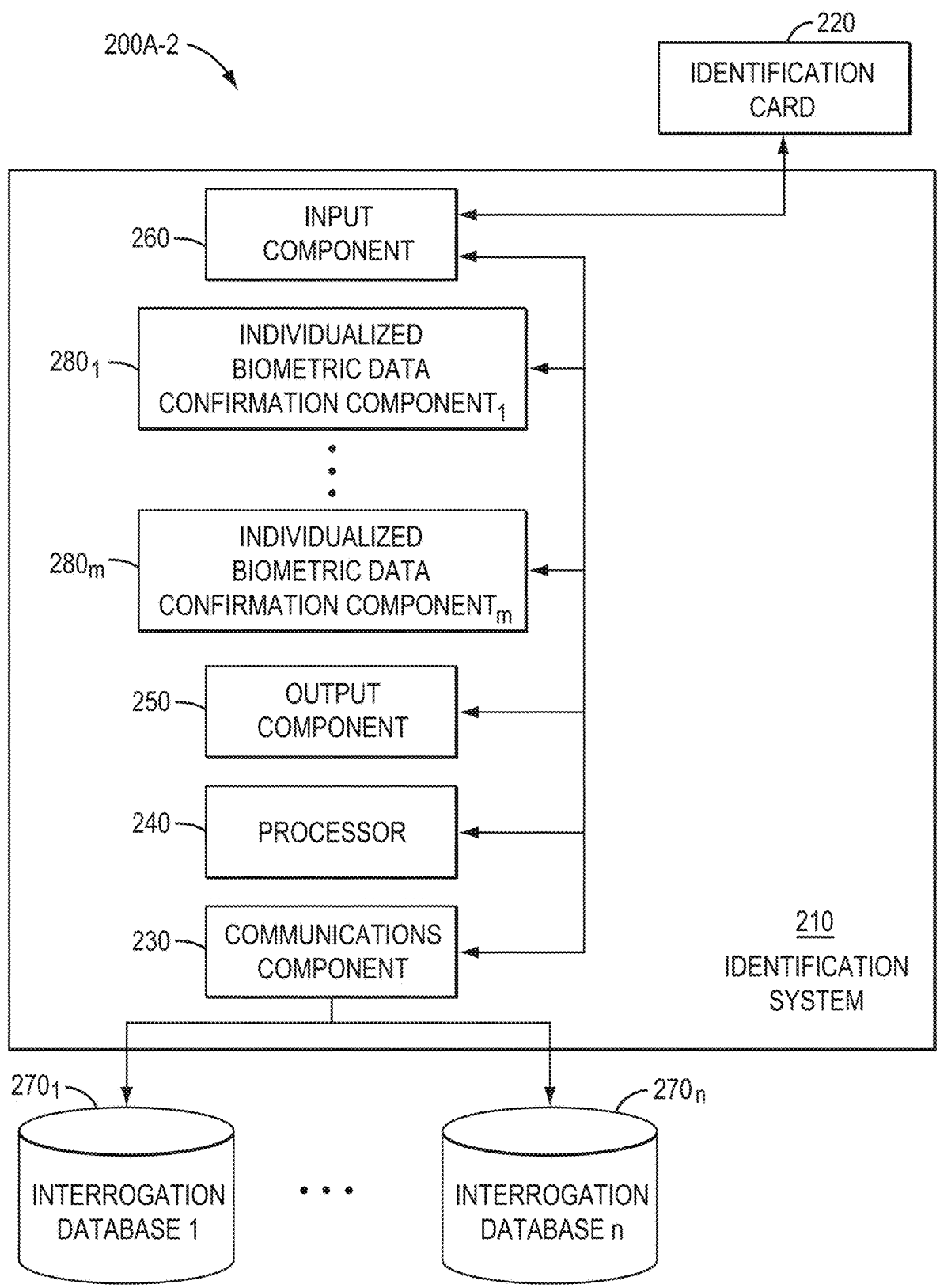

FIGS. 2A-1 and 2A-2 show other embodiments 200A-1 and 200-2, respectively, of the identification system 210 of the invention. In the embodiment of FIG. 2A-1, the identification card 220 is part of the identification system 210. In the embodiment of FIG. 2A-2, the identification system 210 does not include the identification card 220. The identification system 210 includes an identification card 220 configured to be read by the input component 260, which relays individualized information comprising individualized biometric data to the processor 240. In a variation of these embodiments, the identification system obtains the individualized information from another database or repository, and the input component 260 relays the individualized information to the processor 240. The processor 240 communicates via the communication component 230 to interrogation databases $270_1$ to $270_n$, to retrieve a plurality of interrogation database biometric data. The processor 240 interrogates the plurality of interrogation database biometric data and compares it to one or more individualized identification hashes. Additionally, the processor receives individualized biometric data obtained at the point of contact by individualized biometric data confirmation components $280_1$ to $280_m$ and compares the data so obtained to individualized biometric data retrieved from the identification card 220, to verify that the individual who presents the identification card is the individual whose biometric data is stored on the identification card 220. A report is made by the processor 240 via the output component 250 regarding 1) whether or not a match is found with a biometric data entry in interrogation databases $270_1$ to $270_n$ and 2) whether or not a match is found between biometric data obtained at the point of contact from biometric data confirmation components $280_1$ to $280_m$ and the individualized biometric data retrieved from the identification card 220. The processor may further report to another system and/or authority if a match is found in any of the entries of interrogation databases $270_1$ to $270_n$ and/or the biometric data obtained at the point of contact does not match the individualized biometric data retrieved from the identification card 220. The processor may further initiate an action to stop any further processing of the request for access made by the individual upon presentation of the identification card 220, if a match is found in any of the interrogation databases $270_1$ to $270_n$ and/or the biometric data obtained at the point of contact does not match the individualized biometric data retrieved from the identification card 220.

Figures 1, 2B:
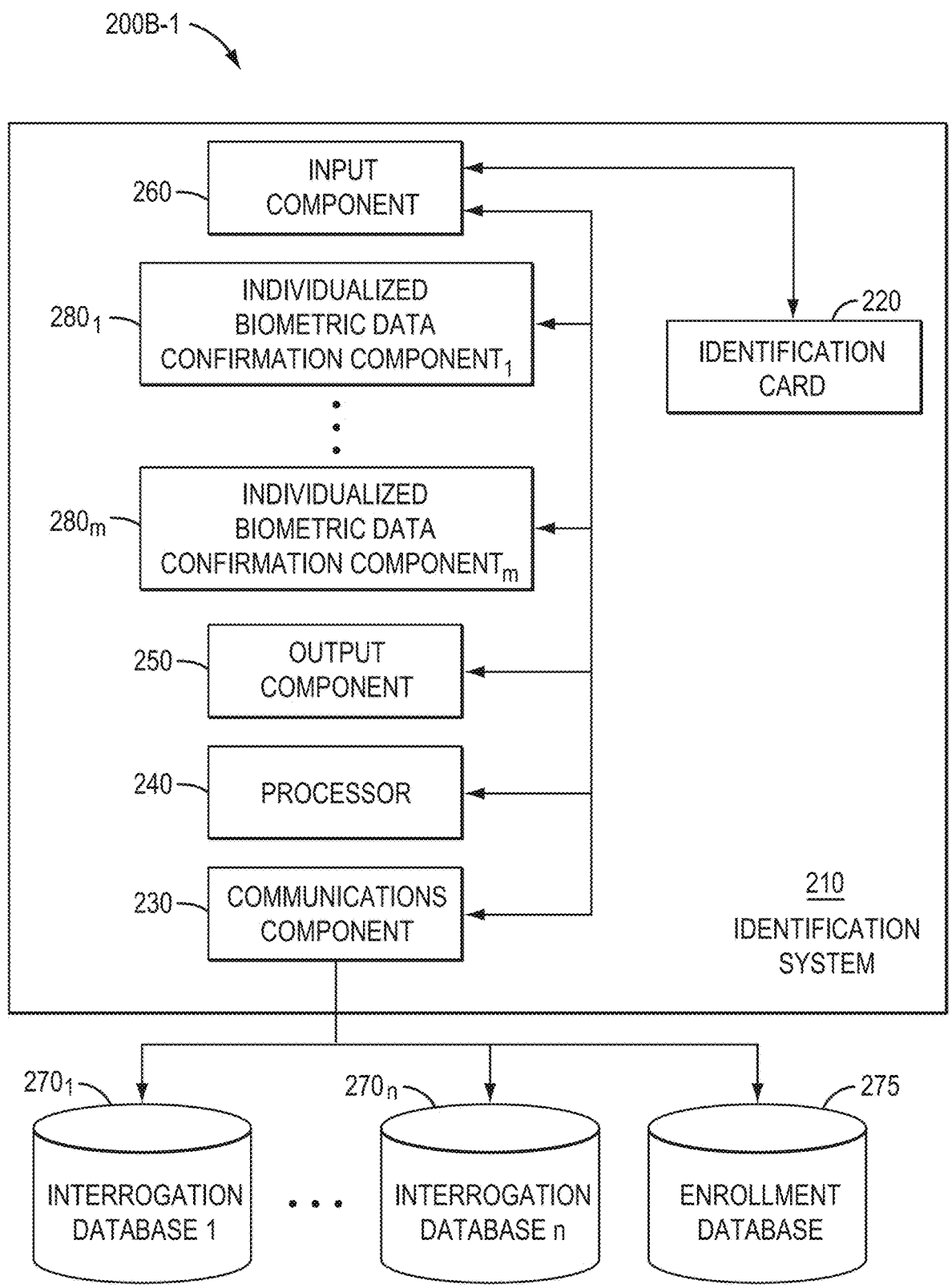
Figures 2, 2B:
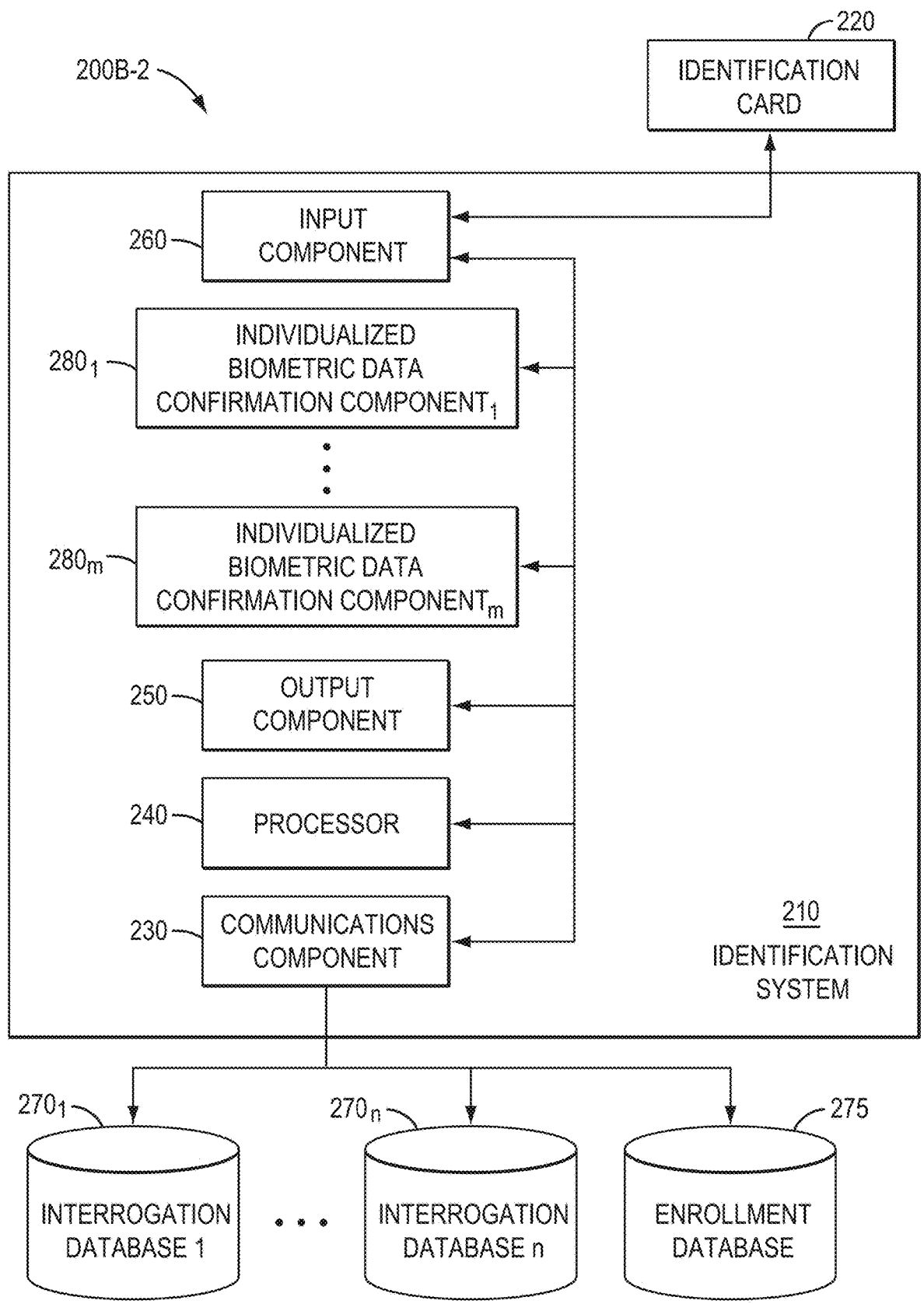

FIGS. 2B-1 and 2B-2 show yet other embodiments 200B-1 and 200B-2, respectively, of the identification system 210 of the invention. In the embodiment of FIG. 2B-1, the identification card 220 is part of the identification system 210. In the embodiment of FIG. 2B-2, the identification system 210 does not include the identification card 220. The identification system 210 includes an identification card 220 configured to be read by the input component 260, which relays individualized information comprising individualized biometric data to the processor 240. In a variation of these embodiments, the identification system obtains the individualized information from another database or repository, and the input component 260 relays the individualized information to the processor 240. The processor 240 communicates via the communication component 230 to interrogation databases $270_1$ to $270_n$, to retrieve a plurality of interrogation database biometric data. The processor 240 interrogates the plurality of interrogation database biometric data and compares it to the individualized identification hash. Additionally, the processor receives individualized biometric data obtained at the point of contact by individualized biometric data confirmation components $280_1$ to $280_m$ and compares the data so obtained to individualized biometric data retrieved from the identification card 220, to verify that the individual who presents the identification card is the individual whose biometric data is stored on the identification card 220. Further, the processor retrieves an enrollment verification certification from the identification card 220, which was assigned at the time of enrollment and issuance of the identification card. The processor interrogates the enrollment database 275 to verify the authenticity of the identification card. This can be performed in several ways, one of which is to search for a matching enrollment verification certification, whereupon the processor further determines whether the other information present on the identification card accompanying the enrollment verification certification matches the record of what was recorded to the card at the time of enrollment. Alternatively, the processor can search for the individual to whom the card was issued and determine whether the enrollment verification certification retrieved from the identification card 220 matches the enrollment verification certification assigned to the card at the time of issuance to the individual. A report is made by the processor 240 via the output component 250 regarding: 1) whether or not the enrollment verification certification is confirmed for the card presented by the individual; 2) whether or not a match is found between biometric data obtained at the point of contact from biometric data confirmation components $280_1$ to $280_m$; and 3) whether or not a match is found to a biometric data entry in interrogation databases $270_1$ to $270_n$. The report issued by the processor may further initiate an action to stop any further processing of the request for access made by the individual upon presentation of the identification card 220, if a match is found in any of the interrogation databases $270_1$ to $270_n$; and/or the biometric data obtained at the point of contact does not match the individualized biometric data retrieved from the identification card 220; and/or the enrollment verification certification is not confirmed for the identification card 220 presented by the individual.

Figure 3A:
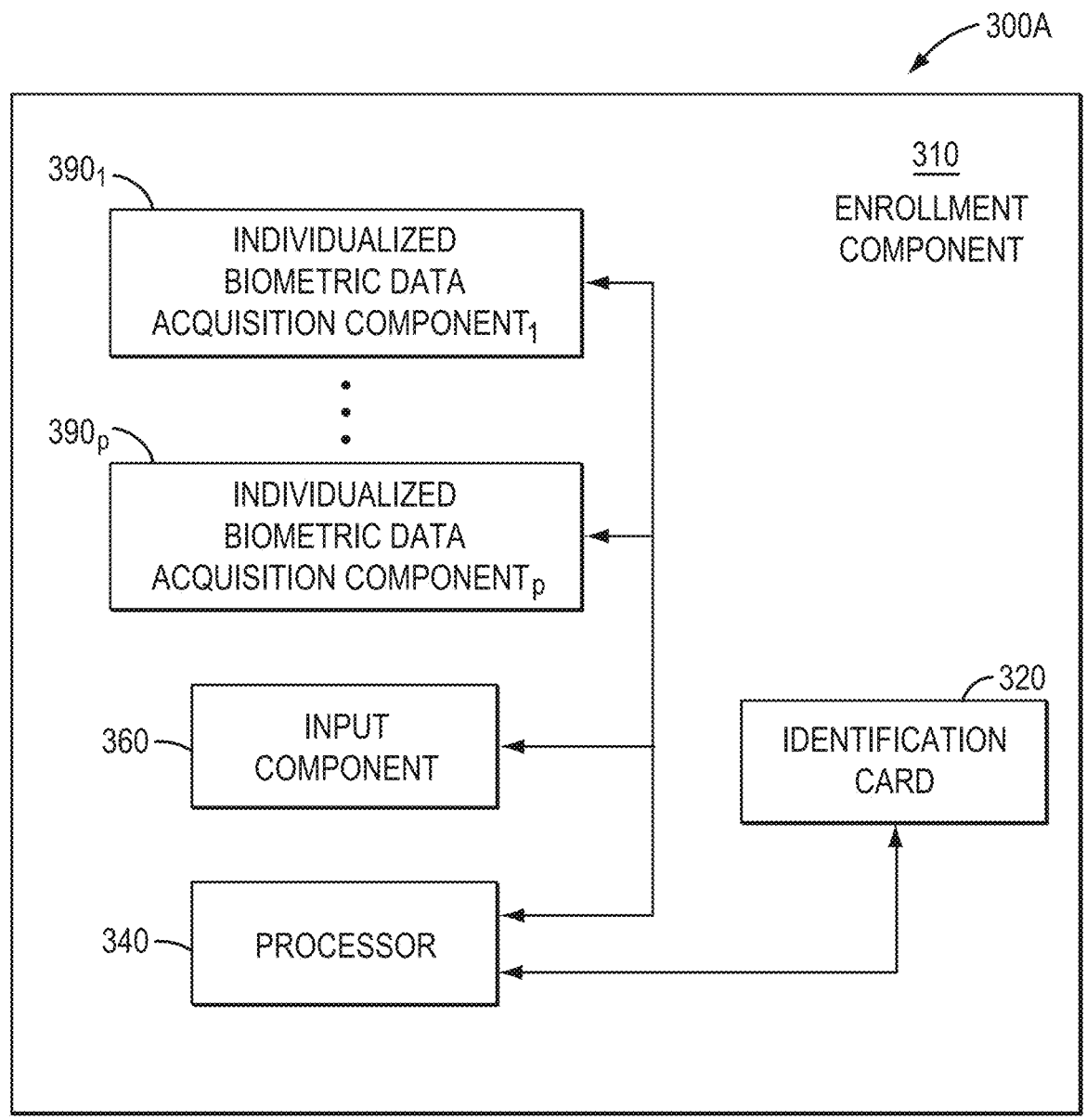
FIG. 3A is a schematic representation of an embodiment of an Enrollment component of the present invention depicting enrollment.
Figure 3B:
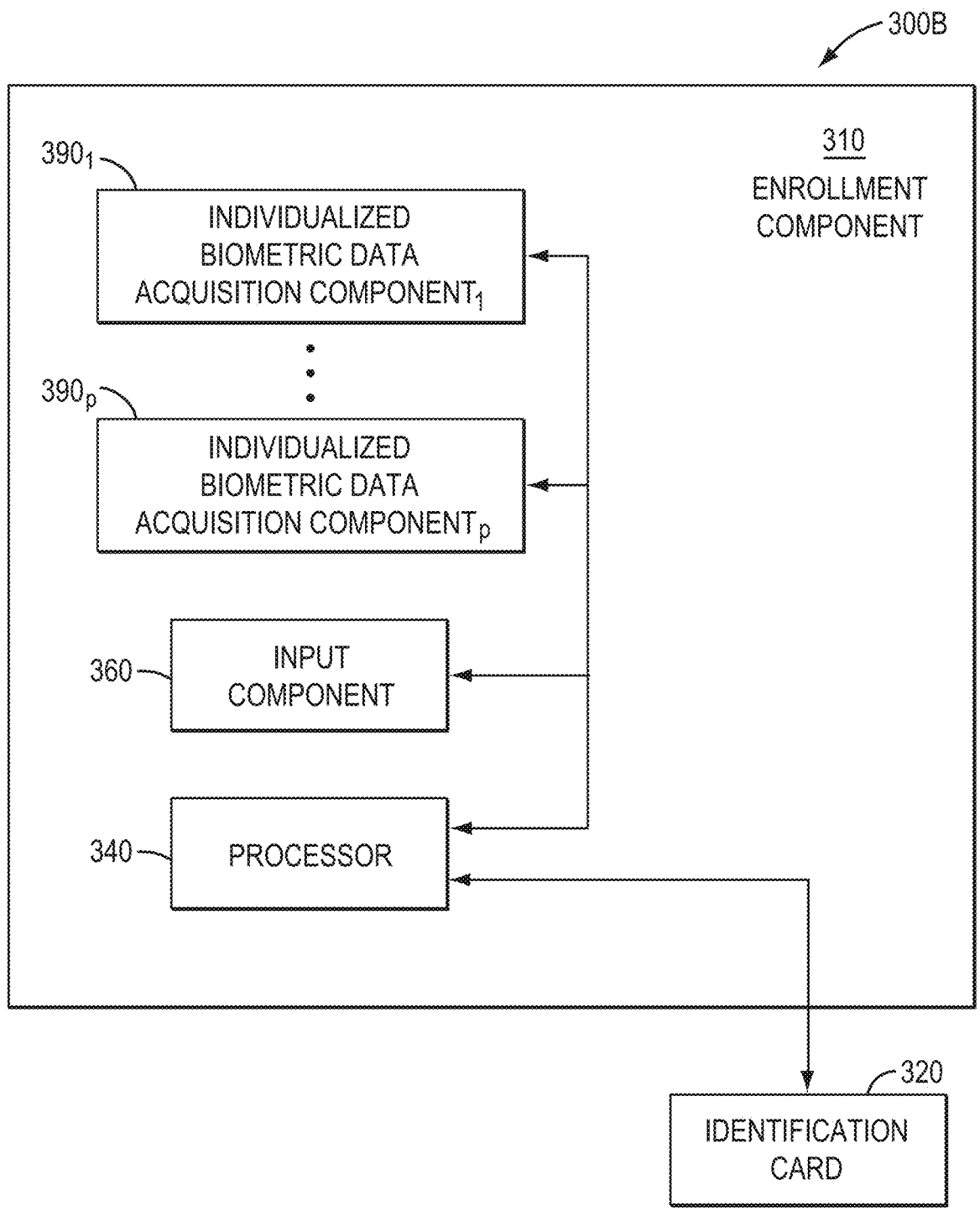
FIG. 3B is a schematic representation of an embodiment of an Enrollment component of the present invention depicting enrollment.

FIGS. 3A and 3B shows various embodiments, 300A and 300B, respectively, of enrollment components of the invention. In the embodiment of FIG. 3A, the identification card 320 is part of the identification system 310. In the embodiment of FIG. 3B, the identification system 310 does not include the identification card 320. An individual desiring to be enrolled would permit biometric data to be obtained by biometric data acquisition components $390_1$ to $390p$. The individualized biometric data so obtained would be further processed by the processor as described below and stored to the identification card 320. The input component may be used to add other individualized information that is stored on the identification card 320. The fully loaded identification card 320 is issued to the individual for use in the identification and verification components of the identification system. In some embodiments, the identification system includes the Enrollment component. In other embodiments, the Enrollment component is a stand alone system.

The identification card containing individualized identification information. In the system of identification described herein, an identification card is issued to an individual after the individual has submitted at least a first and a second class of individualized biometric data. The card may also contain other identifying information such as name, physical description, national origin and address, and the like. The identification card is presented by the individual at a point of contact with an agency granting access to an entity, transport, information, location, security organization, law enforcement organization, transaction, services, authorized status, or funds.

The individualized identification information includes individualized biometric data of at least a first class and a second class, where the individualized biometric data of the first class and the individualized biometric data of the second class has been stored on the card as a first individualized identification hash formed from the individualized biometric data of the first and second class, which may be a one-way hash. Individualized identification information as used herein, encompasses both untransformed and transformed individualized biometric data, including, but not limited to digitized or hashed individualized biometric data. The identification card may include additional individualized identification hashes as is described in the following paragraphs. The identification card further includes at least one additional instance of the individualized biometric data of the first class which is stored on the card as either a graphical individualized biometric data or a digitized individualized biometric data. In some embodiments, the identification card includes two instances of the individualized biometric data of the first class which may be a graphical individualized biometric data and a digitized individualized biometric data. One non-limiting example includes an embodiment where fingerprint scan data is stored on the identification card in a graphical form, i.e., a pictorial or photographic presentation of the fingerprint, or is stored as a digitized fingerprint data string, and in some embodiments, both types of representations are stored on the identification card. Each instance of the individualized biometric data of the at least a first class and/or the one or more individualized identification hashes, including partial individualized identification hashes may be stored on the identification card as one or more barcodes, including but not limited to two-dimensional barcodes.

In some embodiments, the biometric data of the first class may be selected from the group consisting of a fingerprint scan data, a palmprint scan data, a retinal scan data, an iris scan data, and a handvein scan data of the individual. In other embodiments, the biometric data of the first class is selected from the group consisting of a fingerprint scan data, a retinal scan data, an iris scan data, a facial recognition scan data, and a body geometry scan data. In some embodiments, the biometric data of the first class is one or more members of the group of a fingerprint scan data, iris scan data, and a retinal scan data.

The biometric data of the second class may be any suitable biometric data. In some embodiments, the biometric data of the second class may be a DNA data, wherein the DNA data is a STR profile, a SNP profile, an INDEL profile, an Alu element, or a non-STR DNA profile, or the biometric data of the second class may be a fingerprint scan of the individual. In other embodiments the biometric data of the second class is a DNA data, wherein the DNA data is a STR profile, a SNP profile, an INDEL profile, an Alu element, or a non-STR DNA profile of the individual. In some embodiments, the DNA data is any polymorphic DNA sequence that can be used for human identification.

In some embodiments, the biometric data of the first and second class is not of the same class. For example, in one embodiment, the biometric data of the first class is a fingerprint scan data, and the biometric data of the second class is a DNA data. In another embodiment, the biometric data of the first class is a retinal scan data and the biometric data of the second class is a DNA data. In yet other embodiments, the biometric data of the first class is an iris scan data, and the biometric data of the second class is a DNA data. The biometric data of the first class may also be a facial recognition scan data and the biometric data of the second class is a DNA data. Additionally, the biometric data of the first class may be a body geometry scan data and the biometric data of the second class is a DNA data. In a further embodiment, the biometric data of the first class may be a retinal or iris scan data and the biometric data of the second class may be a fingerprint scan data. In another embodiment, the biometric data of the first class is selected from the group of a fingerprint scan data, iris scan data, a retinal scan data, and the biometric data of the second class is a DNA data, wherein the DNA data is a STR profile, a SNP profile, an INDEL profile, an Alu element, or a non-STR DNA profile of the individual. In further embodiments, the biometric data of the first class is selected from the group consisting of a fingerprint scan data, iris scan data, retinal scan data, facial recognition scan data, and body geometry scan data and the biometric data of the second class is a DNA data, wherein the DNA data is a STR profile, a SNP profile, an INDEL profile, an Alu element, or a non-STR DNA profile. In other embodiments, any suitable biometric data may be used as the biometric data of the first class, including fingerprints and palmprints; body geometry features, including but not limited to ear, hand, finger, and the like; facial features; face images; voice; voice prints; optical recognition, including but not limited to iris scans and retinal scans; signatures; blood typing; protein assays; infrared identification, including but not limited to face, hand, and handvein, and gait recognition, and the biometric data of the second class is a DNA data, wherein the DNA data is a STR profile, a SNP profile, an INDEL profile, an Alu element, or a non-STR DNA profile.

When the second class of individualized biometric data includes a DNA data, wherein the DNA data is a STR profile, a SNP profile, an INDEL profile, an Alu element, or a non-STR DNA profile, the DNA data may be hashed non-invertibly with an individualized biometric data that is not a DNA data, forming an individualized identification hash, prior to storage on the card.

In some embodiments, when the individualized biometric data of the second class is a DNA data, for example, an STR profile, the identification card may contain a first individualized identification hash formed from the individualized biometric data of the first class, which may be, without limitation, a fingerprint scan data, and a DNA STR profile. The identification card may also include one or more additional partial individualized identification hashes formed from the fingerprint scan and each STR loci of the STR profile, from the fingerprint scan and at least one subset of all the STR loci of the STR profile, and/or every possible combination of the fingerprint scan data and subsets of the STR loci of the DNA profile of the individual. Optionally, the identification card may include descriptors of these partial individualized identification hashes for comparison against equivalent interrogation database biometric data. In some embodiments, a plurality of partial individualized biometric data sets may be stored on the identification card (such as partial individualized identification hashes).

In one non-limiting example, the digitized fingerprint scan may be hashed with each of the US core STR loci (CSF1PO; FGA; THO1; TPDX; VWA; D3S1358; D5S818; D7S820; D8S1179; D13S317; D16S539; D18S51; D2S11; and Amelogenin), as well as the digitized complete set of US core STR loci, and these additional 14 individualized identification hashes may be used for comparison with the at least one interrogation database. In yet other embodiments, subsets of the complete set of STR loci may be used to form additional individualized identification hashes for comparison with interrogation databases having degraded or incomplete DNA STR profiles. In some embodiments, every possible combination of subsets of the loci of the STR profile is hashed with the digitized fingerprint scan to form a plurality of partial individualized identification hashes. In one non-limiting example, an additional individualized information hash is formed combining the biometric data of the first class with the set of the following loci: CS1PO, D7820, D13S317, D16S539, D18S51, D21S11, FGA, D2S1338, and amelogenin, which may be useful for identification of a degraded DNA sample. In some embodiments, one or more partial individualized identification hashes is formed from a subset of two or more, three or more, four or more, five or more, six or more, seven or more, or eight or more STR loci.

In another non-limiting example, the individualized biometric data of the first class is an iris scan, and the individualized biometric data of the second class is a DNA data which is a STR profile. The same process may be employed as described in the above paragraphs, using the iris scan data, which may be digitized, and the DNA STR profile, which may be digitized, above to provide a first individualized identification hash, and optionally, a plurality of partial individualized identification hashes.

The individualized identification information may further include a third or more class of individualized biometric data or more. The third and additional classes of individualized biometric data may be present on the identification card in a hashed form, and may be invertible. The third and additional classes of individualized biometric data may be present on the identification card in a non-invertible hashed form. When the individualized identification card includes a third or more class of individualized biometric data, the biometric data may be of any type of biometric data. In some embodiments, the biometric data of a third class is a different class of biometric data from that of the first and second class of biometric data. In some embodiments, when the first class of biometric data is a fingerprint data, then the third class of biometric data is a retinal scan data. Additionally when the first class of biometric data is a fingerprint scan data and the third class of biometric data is a retinal scan data, then the second class of biometric data may be a DNA data, wherein the DNA data is a STR profile, a SNP profile, an INDEL profile, an Alu element, or a non-STR DNA profile. In other embodiments, when the first class of biometric data is a retinal scan data, then the third class of biometric data is a fingerprint data. Additionally when the first class of biometric data is a fingerprint scan data and the third class of biometric data is a retinal scan data, then the second class of biometric data may be a DNA data wherein the DNA data is a STR profile, a SNP profile, an INDEL profile, an Alu element, or a non-STR DNA profile. The invention also provides embodiments where the first class of biometric data is an iris scan, the third class of biometric data is a fingerprint scan data, and the second class of biometric data may be a DNA data, wherein the DNA data is a STR profile, a SNP profile, an INDEL profile, an Alu element, or a non-STR DNA profile. In yet other embodiments, the first class of biometric data is a fingerprint scan data, the third class of biometric scan data is a facial recognition scan data or a body geometry scan data, and the second class of biometric data is a DNA data, wherein the DNA data is a STR profile, a SNP profile, an INDEL profile, an Alu element, or a non-STR DNA profile.

In yet other embodiments, biometric data of the first class is an iris scan data, retina scan data, a facial recognition scan data, or a body geometry scan data, biometric data of the second class is a fingerprint scan data, and the third class of biometric data is a DNA data, wherein the DNA data is a STR profile, a SNP profile, an INDEL profile, an Alu element, or a non-STR DNA profile. When the DNA data is present only as biometric data of the third class, it is present hashed together with biometric data of either the first or the second class in a non-invertible form, and may be used to in the comparison with an interrogation database in order to determine whether the individual's DNA data is present in the database.

In some embodiments, the biometric data of a third class is of the same class of biometric data as the second class of biometric data, but is a different type of the same class of biometric data. For example, in one embodiment, biometric data of a second class is a DNA STR profile, and biometric data of a third class is an INDEL profile. In another embodiment, the biometric data of a second class is a DNA STR profile and the biometric data of a third class is a SNP profile. In another embodiment, the biometric data of a second class is a DNA STR profile and the biometric data of a third class is an Alu element. In some embodiments, when the biometric data of the second class and the biometric data of the third class present on the individualized identification card are both types of DNA data, each of the biometric data is hashed with the biometric data of the first class prior to storage as individualized identification hashes on the identification card. In some embodiments, when the biometric data of the second class and the third class are both types of DNA data, the hash is one-way and is not invertible. When a third class of biometric data of the third class is a DNA data stored as a combined one way hash on the identification card, the third class of biometric data may be used in comparison with the at least one interrogation database.

In some embodiments of the method, more than three classes of individualized biometric data are present on the identification card. There may be more than three classes of individualized biometric data that are all of different classes, including without limitation, iris, retina, fingerprint, DNA data which includes one or more of a STR profile, a SNP profile, an INDEL profile, an Alu element, or a non-STR DNA profile, facial recognition scan data, or body geometry data. In some embodiments, the more than three classes of individualized biometric data includes more than one type of DNA data selected from a STR profile, a SNP profile, an INDEL profile, an Alu element, and a non-STR DNA profile. When any of the more than three classes of individualized biometric data includes a DNA data, wherein the DNA data is STR profile, a SNP profile, an INDEL profile, an Alu element, or a non-STR DNA profile, the DNA data is hashed non-invertibly with an individualized biometric data that is not a DNA data, prior to storage on the identification card. When more than three classes of biometric data are present on the identification card, each of the classes of biometric may be used in comparison with the at least one interrogation database.

Each of the instances of the at least a first class of individualized biometric data, the at least a first individualized identification hash and/or one or more partial individualized identification hashes may be stored on the identification card as a barcode, alphanumerical or a graphical representation. The barcode may be a two dimensional barcode, including but not limited to a matrix barcode.

The identification card may include descriptors of the types of biometric data or subtypes of biometric data stored on the card; to be read by the processor in order to determine what interrogation databases may have suitable entries for interrogation. Additionally, there may be instructions or descriptors to cue the processor to reorganize or reorder entries in the interrogation databases to maximize the possibility of finding a match.

Other types of individualized identification information may be present on the identification card, including but not limited to parametric data such as name; age; physical description, including but not limited to hair color, height, weight, eye color, skin color description, and other individualized descriptors such as tattoos and the like; social security number; mother's maiden name; health information; health insurance information; marital status; dependent children status; financial or credit card information; address; nationality; citizenship status; visa status; voter registry status; driver license number; and the like.

The at Least One Interrogation Database Containing a Plurality of Interrogation Biometric Data.

The at least one interrogation database includes information associated with identification of individuals. For example, the at least one interrogation database can be governmental (Federal, state, regional and/or local) data store(s) related to, for example, the Social Security Administration, Drivers' license agencies (e.g., Bureau/Department of Motor Vehicles), state identification card issuing agencies, the Selective Service system, the military, voter registration, birth certificates issuing authorities, the Immigration and Naturalization Service, Homeland Security, the Justice Department, the Bureau of Alcohol, Tobacco and Firearms, the Federal Bureau of Investigation and/or the Central Intelligence Agency. The at least one database may be maintained by extraterritorial governmental and nongovernmental organizations (e.g., European Union, the United Kingdom, including but not limited to antiterrorism databases maintained by organizations such as MI5, Germany, and Interpol). The at least one interrogation database can also include private, non-governmental, databases that can include, for example, a periodically updated copy of governmental data and/or a new set of data about an individual. Other nongovernmental groups maintaining databases may include kinship databases or genealogy-related databases. Additionally, the at least one interrogation database can include DNA data (e.g., collected by governmental and/or private entities) and/or other biometric data. Information can be stored in the at least one interrogation database in a variety of format(s) including, but not limited to, hierarchical database(s) and/or relational database(s). Information can be stored in the at least one interrogation database in a variety of data structure(s) including, but not limited to, lists, arrays, databases and/or data cubes. For example, information stored in the at least one interrogation database can be text (e.g., alphanumeric), graphical, audio, video and/or digitally stored DNA data. In some databases, the information does not have individualized identification associated with the record, i.e. for the biometric data there is no personal name available as an identifier. In some embodiments, the interrogation biometric data is associated with an interrogation database identifier. In some embodiments, the at least one interrogation database includes DNA profile data that is not complete or is degraded. This incomplete or degraded DNA profile data may be a partial or degraded STR profile data, SNP profile, INDEL profile, Alu element data, non-STR profile, or a combination of one of more of these profile types. For example, the at least one interrogation database may include a DNA STR profile for which the data for some of the core loci is not available due to degradation of the initially obtained sample.

In some embodiments, the interrogation biometric data may be a fingerprint scan data, iris scan data, retinal scan data, facial recognition scan data, body geometry scan data, or gait analysis data.

There may be only one type of biometric data in each database or there may be more than one type of biometric data. The biometric data in each database may also have a personal name associated with the data. The biometric data in each database may only be identified by an interrogation database identifier, and may have no personal name associated with the data.

In some embodiments of the invention, the interrogation biometric data of the second class is a DNA data. The DNA data may be a STR profile, a SNP profile, an INDEL profile, an Alu element data, a non-STR profile, or a combination of one of more of these profile types. In another embodiment, the interrogation biometric data of the second class is a fingerprint scan data. In yet another embodiment, the interrogation biometric data of the second class is partial or degraded DNA data, including a partial or degraded STR profile, SNP profile, INDEL profile, Alu element data, non-STR profile, or a combination of one of more of these profile types.

The processor. As used herein, "the processor" may be a single processor or may be more than one processor as may be required to perform the methods of the inventions.

A. The Processor is Configured to Read and Retrieve the Identification Information Contained on the Identification Card Presented by the Individual.

The processor is configured to read and retrieve individualized identification information, including individualized biometric data, of any class, combination, or format as described for the identification card and identification system. The individualized identification information comprising individualized biometric data of at least a first class and at least a first individualized identification hash is retrieved by the processor from the identification card. In some embodiments, the individualized biometric data is read by an input component which includes but is not limited to a card reader, a magnetic card reader, keyboard, a touch screen device, computer, a pointing device, such as a mouse, a microphone, an IR remote control, a joystick, a game pad, a personal digital assistant (PDA), a smart card reader, or the like. The processor is configured to determine what classes of biometric data have been stored on the identification card and how the biometric data is presented on the card, including any preprocessing.

B. the Processor is Configured to Communicate with the at Least One Interrogation Database.

Upon reading the individualized identification information from the identification card, the processor is configured to determine what classes of biometric data are present in the at least the first individualized identification hash. The processor is configured to determine which interrogation database contains at least some records containing biometric data of the same class as the individualized biometric data of the second class present in the individualized identification hash. The processor is further configured to instruct the communications component to connect to the at least one interrogation database.

Further, when the identification card does not have the individualized biometric data present in the local device presented at the point of contact, the processor may be configured to retrieve the individualized biometric data from a remote database upon entry of a password or other electronic entry permission granting procedure. In some embodiments, the remote database may be the enrollment database.

The processor connects to the at least one interrogation and/or remote database via a communications component. The communications component may be one or more communications components. Communication by the communications component may be achieved via many types of connections, including but not limited to network connection, an extranet, an intranet, the Internet, wireless communication, direct serial communication, and/or direct parallel communication. Information exchanged between the processor and the at least one database can utilized a variety of formats, and in a variety of secure and/or encrypted manners, a non-limiting example being a high-speed secure Internet connection.

C. The Processor is Configured to Interrogate the Interrogation Database.

The processor is configured to retrieve biometric data of the second class from the at least one interrogation database. The processor is configured to reorder data, particularly DNA or RNA data so that the data in an interrogation database is ordered in the same manner as the data on the identification card. A non-limiting example includes reordering a list of STR profile data so that the loci of the STR data are listed in the same order as that of STR profile data listed on the identification card. The data may be reorganized to present an interrogation database biometric data similarly to that of the biometric data used in the individualized information hash to provide interrogation database identification hashes having an equivalent precursor structure, and allow the greatest probability of finding a match. A non-limiting example of reorganizing data of an interrogation database is re-processing graphic representations of fingerprint scans via the same algorithm as used to enroll a fingerprint scan for the individual.

The processor is configured to hash each of the plurality of interrogation biometric data of the second class together with the individualized biometric data of the first class to form a plurality of interrogation database identification hashes.

The processor may be configured to use the individualized biometric data of the first class as stored in the identification card. In some embodiments, the digitized individualized biometric data of the first class is retrieved by the processor from the identification card and hashed together with each of the plurality of the interrogation biometric data of the second class to form a plurality of interrogation database identification hashes for use in the comparison to the individualized identification hash. In another embodiment, the processor may retrieve the individualized biometric data of the first class as a hashed form and the processor may be configured to invert the individualized biometric data of the first class prior to being hashed together with each of the plurality of interrogation biometric data of the second class to form a plurality of interrogation database identification hashes for use in the comparison to the individualized identification hash. In yet other embodiments, the individualized biometric data of the first class may be retrieved as a hashed form and the hashed form is hashed together with each of the plurality of interrogation biometric data of the second class to form a plurality of interrogation database identification hashes for use in the comparison to the individualized identification hash. In other embodiments, the individualized biometric data of the first class is retrieved as a graphical individualized biometric data and converted to a digitized individualized biometric data as part of the process of forming the plurality of interrogation database identification hashes in combination with each of the plurality of the interrogation biometric data of the second class.

The processor is configured to compare each interrogation database identification hash to the at least a first individualized identification hash stored on the identification card of the individual. By comparing only identification hashes combining an individualized biometric data of the first class retrieved from the identification card with an interrogation biometric data of the second class to the individualized identification hash presented by the individual, the individualized biometric data of the second class, i.e., a DNA data of the individual may be protected from unauthorized access or use. In various embodiments, the individualized biometric data of the second class that is used to form the first individualized identification hash is a DNA data that is a STR profile data, a SNP profile, or an INDEL profile.

In some embodiments, the processor interrogates databases having additional classes of biometric data. While the at least a first individualized identification hash may be used to identify matches formed with the interrogation database identification hashes which contain biometric data of the second class, the individualized biometric data of the first class, or the individualized biometric data of the third or more class may be used to interrogate other databases without being hashed together with individualized biometric data of the second class. A non-limiting example includes an identification card containing fingerprint scan data as biometric data of the first class and DNA data as biometric data of the second class, where the individualized identification hash is formed using both fingerprint scan data and DNA data. While databases containing DNA data can be interrogated by forming interrogation database identification hashes from the individualized biometric data of the first class and each of the entries in the interrogation database containing DNA data to find a match, the instances of the first class of individualized biometric data, i.e., fingerprint scan data, or that of the third or more class of individualized biometric data, i.e. iris scan data, retina scan data, facial feature scan data, or body geometry scan data may also be used to interrogate databases containing respective types of biometric data, without forming additional hashes. In this embodiment, a database containing a fingerprint having limited or no identification information such as name or other parametric data may be reported as forming a match with biometric data enrolled on the identification card, thus providing an identification permitting further action as required by the specific request for access.

The processor may also be configured to compare each interrogation database identification hash to at least one additional individualized identification hash formed from a third or more class of biometric data, when such one-way combined hash is formed from a DNA data. When a third class or more class of biometric data of the third class is a DNA data stored as a combined one-way individualized hash with non-DNA biometric data on the identification card, then the processor may be configured to interrogate at least one interrogation having DNA data by retrieving the instance of individualized non-DNA biometric data that had been used to generate the combined one-way hash, and forming a plurality of interrogation database identification hashes with each of the plurality of interrogation biometric data of the interrogation database. The processor may be configured to compare each interrogation database identification hash to the individualized identification hash or hashes stored on the identification card of the individual, and determine whether a match is identified.

In some embodiments, the processor is configured to recognize that the identification card includes one or more partial individualized identification hashes, formed from the individualized biometric data of the first class and partial individualized biometric data of the second class. In one example, the partial individualized biometric data of the second class is a partial DNA profile. The processor may be configured to communicate to at least one interrogation database including DNA biometric data that may be an incomplete or partial DNA profile. The processor may be configured to form interrogation database identification hashes from the individualized biometric data of the first class and each interrogation database DNA data to form an interrogation database identification hash. In some embodiments, the processor is configured to determine what subtype of partial DNA profile data is present, determine whether an individualized identification hash on the identification card was formed from a matching subtype, and if one is present, then is configured to form interrogation database identification hashes with the biometric of the first class extracted from the identification card. The processor may also be configured to retrieve a plurality of partial individualized identification hashes, compare each of the plurality of partial individualized identification hashes to each interrogation database hash formed as described above, and report if any matches are identified. The processor may not be configured to identify any characteristic of the partial individualized identification hashes in order to make the comparison with each of the interrogation database identification hashes. In yet other embodiments, the processor is configured to retrieve a plurality of partial individualized identification hashes, form a plurality of interrogation database identification hashes from each entry of the interrogation database, compare the plurality of partial individualized identification hashes to the plurality of interrogation database identification hashes, report matches for each entry of the interrogation database, and repeat for all entries of the interrogation database. The processor may be configured to report the percentage of alleles matched data, and number of loci compared. The processor may be further configured to calculate whether any identified match has a predetermined probability of representing a match for the individual or is too fragmentary to be significant. The processor may be further configured to attempt matching other biometric data or parametric data present on the identification card with equivalent data in the interrogation database entry to determine significance of the match. In some embodiments, the processor may be configured to compare a plurality of partial individualized identification hashes to a plurality of interrogation database identification hashes, or compare a plurality of partial individualized identification hashes to partial interrogation database identification hashes with or without comparing a first individualized identification hash to a plurality of interrogation database identification hashes.

Additionally, only the processor views any unencrypted DNA data, either at the point of enrollment, the point of contact or in the process of interrogating the interrogation database and the point of comparing.

The processor is configured to report if a match is found between an interrogation database identification hash and the individualized identification hash. If a match is found, the report may include a requirement for further investigation of the individual. The processor may also report that no match is found, thereby permitting the individual to gain access to the entity, transport, information, location, security organization, law enforcement organization, transaction, services, authorized status, or funds requested.

The system includes an output component that is configured to communicate the report in any suitable manner. Output devices include but are not limited to a touch screen device, a computer monitor, a television screen, a printer, a personal digital assistant, a wireless or wired telephone display or message, a speaker(s), a computerized messaging unit, and the like.

D. the Processor is Configured to Confirm the Identity of the Individual Presenting the Identification Card.

The processor may be configured to read at least a first class of individualized biometric data at a point of contact; and confirm the at least first class of individualized biometric data at the point of contact to verify the identity of the individual presenting the identification card, thus providing a verification component to the systems and methods of the invention. In some embodiments, a third or more class of individualized biometric data is obtained by individualized biometric data confirmation components at the point of contact to compare with the biometric data stored on the identification card. In some embodiments, third or more class of individualized biometric obtained at the point of contact includes, but is not limited to fingerprint scan data, retinal scan data, iris scan data, and the like.

The individual may be required to submit to a scan of one or more biometric data types at the point of contact. The processor is configured to communicate with the biometric data acquisition and data processing components to obtain and process the locally acquired biometric data. The locally acquired biometric data may be used in its undigitized form or may be converted into a digital format.

The processor is configured to compare the locally acquired biometric data to the individualized biometric data stored on the identification card. The individualized biometric data from the identification card may be inverted from a hashed form or the locally acquired biometric data may be subjected to the same digitization or hashing processes used to convert the individualized biometric data for storage on the identification card at the time of enrollment. This component of the identification system determines that the individual presenting the identification card is the individual whose biometric data are recorded on the identification card. If a match is not found, a report may be made. If a match is not found, the processor may be configured to deny the individual access to the entity, transport, information, location, security organization, law enforcement organization, transaction, services, authorized status, or funds to which the individual has made a request or require further investigation.

E. The Processor is Configured to Confirm the Authenticity of the Identification Card.

The processor may be configured to retrieve an enrollment verification certification from the identification card, and interrogate the enrollment database. The processor may be configured to search for a matching enrollment verification certification, whereupon the processor further determines whether the other information present on the identification card accompanying the enrollment verification certification matches the record of what was recorded to the card at the time of enrollment. Alternatively, the processor may be configured to search for the individual to whom the card was issued and determine whether the enrollment verification certification retrieved from the identification card matches the enrollment verification certification assigned to the card at the time of issuance to the individual. If a match is found, the processor is configured to permit the process of identifying the individual to proceed. If no match is found, the processor is configured to report that no match has been found and the access request process is halted for further investigation. The report may include notifying another system and/or authority.

F. the Processor May be Configured to Enroll the Individual and Produce the Identification Card of the System.

The processor may be configured to acquire at least a first class and a second class of individualized biometric data. The processor is configured to convert biometric data of the first class to a digital electronic format, and to store one instance of the biometric data of the first class on the identification card, in the digitized electronic format. In some embodiments, the processor is configured to hash the biometric data of the first class in an invertible form prior to storage on the card. In other embodiments, the processor is configured to hash the biometric data of the first class in a non-invertible form prior to storage on the card. In some embodiments, the processor is configured to perform other post processing of the electronically digitized biometric data of the first class. In other embodiments no post processing of the electronically digitized biometric data of the first class is performed. In yet other embodiments, the processor is configured to store the biometric data of the first class with no further processing after the initial acquisition, i.e. as a raw image of a biometric data, including but not limited to a fingerprint scan data, a retinal scan data and an iris scan data, thus provide individualized biometric data as a graphical individualized biometric data.

When the second class of biometric data is nucleic acid, i.e. either DNA or RNA, a sample of the individual's DNA is collected and analyzed. The processor is configured to convert the DNA or RNA data to a digital electronic format. The processor is configured to hash the digitized electronic DNA results with a second instance of the electronically digitized first class of biometric data of the individual to form a first individualized identification hash. In some embodiments the hashing process is invertible. In other embodiments, the hashing process is noninvertible. The processor is may be configured to store the first individualized identification hash on the identification card.

In some embodiments, the processor is configured to hash subsets of the digitized electronic DNA results with the second instance of the electronically digitized first class of biometric data of the individual. For example, when the DNA data is a STR profile, the processor may be configured to hash each STR loci of the STR profile, at least one subset of all the STR loci of the STR panel, and/or every possible combination subsets of the STR loci with the digitized first class of biometric data to form a plurality of partial individualized identification hashes. The processor may be configured to store the plurality of partial individualized identification hashes on the identification card.

The processor may be configured to acquire a third or more classes of biometric data, and convert the data to a digital electronic format. The third or more classes of biometric data may be hashed before storage on the identification card. In some embodiments the hash of the third or more classes of biometric data is invertible. In other embodiments the hash of the third or more classes of biometric data is non-invertible. In some embodiments other post processing of the electronically digitized biometric data of the third or more class is performed. In other embodiments no post processing of the electronically digitized biometric data of the third or more class is performed.

When a biometric data including a nucleic acids profile, either DNA or RNA, is used, for example, as a biometric data of the third or more class, the processor may be configured to hash the DNA or RNA biometric data of the third or more class with the electronically digitized biometric data of the first class, prior to storage on the identification card. In some embodiments, the hashing of the DNA or RNA containing third class of biometric data and the first class of biometric data is non-invertible. In other embodiments, the hashing of the DNA or RNA biometric data of the third class and the first class of biometric data is invertible.

The processor may be further configured to store each of the instances of the at least a first class of individualized biometric data, the at least a first individualized identification hash and/or one or more partial individualized identification hashes as a barcode, alphanumerical or a graphical representation. The barcode may be a two dimensional barcode, including but not limited to a matrix barcode. In some embodiments, the processor is configured to store each of these instances of individualized biometric data on an identification card.

The processor may be configured to assign each newly issued card with an enrollment verification certification. The certification may be used to authenticate the identification card as a card issued by the enrollment authority. The biometric data, in its hashed form, may be stored in an enrollment database. This may provide another mode of verification at the point of contact when the identification card is presented to request access to an entity, transport, information, location, security organization, law enforcement organization, transaction, services, authorized status, or funds.

Enrollment Component.

The enrollment component may include one or more biometric data acquisition and data processing components. Biometric data acquisition components include instruments configured to scan biometrics including, but not limited to, fingerprints and palmprints; body geometry features, including but not limited to ear, hand, finger, and the like; facial features; face images; voice; voice prints; optical recognition, including but not limited to iris scans and retinal scans; infrared identification, including but not limited to face, hand, and handvein; and the like, and may be present at the point of contact. Biometric data acquisition components may further include instruments configured to obtain a sample of nucleic acid, i.e. either DNA or RNA. Biometric data acquisition components may also include instruments configured to analyze the DNA or RNA, and provide a DNA profile or a RNA profile. Biometric acquisition components may also include instrumentation configured to analyze a biological sample of the individual, including but not limited to blood, serum, urine, tissue, saliva, tears, or any other bodily fluid or solid tissue type. The instrumentation may include protein analyzers, gene expression analyzers, blood type analyzers, and the like. An input component may be included to submit the biometric data obtained by the one or more biometric acquisition components into the enrollment component of the system. Data processing components may be incorporated in the enrollment component to digitize and further process the raw biometric data. In some embodiments the processing includes hashing the biometric data.

Verification Component.

The verification component may include one or more individualized biometric data confirmation components which may each include biometric data acquisition and data processing components. Biometric data acquisition components include instruments configured to scan biometrics including, but not limited to, fingerprints and palmprints; body geometry features, including but not limited to ear, hand, finger, and the like; facial features; face images; voice; voice prints; optical recognition, including but not limited to iris scans and retinal scans; infrared identification, including but not limited to face, hand, and handvein; and the like, and may be present at the point of contact. An input component may be included to submit the biometric data obtained by the one or more biometric acquisition components into the verification component of the system. Data processing components may be incorporated in the individualized biometric data confirmation component to digitize and further process the raw biometric data. In some embodiments the processing includes hashing the biometric data. In some embodiments the processing includes hashing two classes of biometric data together. Other data processing components included in the verification component include data processing components configured to compare the individualized biometric data obtained at the point of contact from the individual with the individualized biometric data stored on the identification card of the individual. Additional data processing components include processors configured to compare an enrollment verification certification stored on the identification card with an enrollment verification certification stored on an enrollment database. The verification component also may include a processor configured to issue a report whether or not the individualized biometric data obtained at the point of contact matches the individualized biometric data stored on the identification card of the individual. The verification component also may include a processor configured to issue a report whether or not the enrollment verification certification retrieved from the identification card at the point of contact matches the enrollment verification certification enrolled for the individual stored on the enrollment database.

Computer Readable Medium.

The computer readable medium is a computer program that instructs a computer, which term is interchangeable with "processor", which is in or connected to the identification card reader. The computer readable medium is configured to instruct the processor read and retrieve individualized identification information of any class, combination, or format as described for the identification card and identification system. The computer program may instruct the processor to invert one or more invertible instances of individualized biometric data of any class. The computer program may instruct the processor to determine what classes of biometric data are stored on an identification card. The computer program may instruct the processor to retrieve at least a first class of individualized biometric data and a first individualized identification hash from the identification card. In embodiments where the identification card does not carry the individualized biometric data locally, the computer program may instruct the processor to retrieve the individualized biometric data from another database, which may be an enrollment database. The computer program may instruct the processor to connect, using the communications component(s), to the at least one interrogation database and to retrieve appropriate class(es) of biometric data. The computer program may instruct the processor to retrieve the plurality of interrogation biometric data of the second class and, if necessary, reorder and/or reorganize each of the plurality of interrogation biometric data of the second class to be presented in the same order of presentation and manner as that of the individualized biometric data of the second class. The computer program may instruct the processor to hash the first class of individualized biometric data in combination with each of the plurality of the interrogation biometric data to form a plurality of interrogation identification hashes. When a third class or more class of individualized biometric data of the third class is a DNA data stored as an additional combined one-way individualized identification hash with non-DNA biometric data on the identification card, then the computer may instruct the processor to interrogate at least one interrogation database having DNA data by retrieving the instance of individualized non-DNA biometric data that had been used to generate the combined one-way hash, and to form a plurality of interrogation database identification hashes using each of the plurality of interrogation biometric data of the interrogation database. The computer program may further instruct the processor to compare each of the interrogation database identification hashes with the first individualized identification hash and/or additional individualized identification hashes. The computer program may instruct the processor to compare other individualized biometric data of the first or of the third or more classes with interrogation database data of the same type. The computer program may instruct the processor to report a match, if found. The report can be a local report or a report to an external authority.

Interrogation of Partial DNA Data.

The computer readable medium may instruct the processor to perform a comparison with partial data, and optionally, to provide a weighting function to determine significance of a match found using partial data, such as partial DNA profiles. The computer program may instruct the processor to identify whether at least one interrogation database contains interrogation biometric data which may be incomplete, degraded, or has portions of the biometric data obscured by contaminants. The computer program may instruct the processor to determine what portions of interrogation biometric data are available for comparison with individualized biometric data. The computer program may then instruct the processor to retrieve respective partial individualized biometric data sets that may be stored on the identification card. In one non-limiting example, the identification card contains a first individualized identification hash formed from a fingerprint scan data and a DNA STR profile. The identification card may also include one or more additional partial individualized identification hashes formed from the fingerprint scan and each STR loci of the STR panel, from the fingerprint scan and at least one subset of all the STR loci of the STR panel, and/or every possible combination of the fingerprint scan data and subsets of the STR loci. The computer program may instruct the processor to retrieve descriptors of these partial individualized identification hashes from the identification card for comparison against equivalent interrogation database biometric data. The computer program may instruct the processor to compare each of the plurality of partial individualized identification hashes formed from the fingerprint scan data and the subsets of DNA STR loci of the individual to a partial interrogation database identification hash formed from the fingerprint scan data of the individual and a potentially incomplete or partial DNA STR data entry of the at least one interrogation database. The computer program may also instruct the processor to perform a comparison between the individualized identification hash and the interrogation database identification hash formed from the DNA data of the database entry to permit interrogation whether the DNA data of the interrogation database entry is complete or incomplete.

The computer program may instruct the processor to report each match found between any of the plurality of individualized identification hashes (complete or partial) and the interrogation database identification hash. The computer program may instruct the processor to identify whether all the STR loci of the STR profile of the individual, or identify which of the subset or subsets of the STR loci of the individual provided a match, as the identity of the STR loci may be identifiable without revealing the individual's alleles, thus still providing privacy. In some embodiments, the computer program may instruct that a match may be reported by the processor when the partial individualized identification hash used in the comparison is formed from a subset of two or more STR loci. In other embodiments, a match may be reported when the partial individualized identification hash used in the comparison is formed from a subset of three or more, four or more, five or more, six or more, seven or more, or eight or more STR loci. In other embodiments, a match may be reported when more than one partial individualized identification hash matches the partial interrogation database identification hash. One of skill may determine which subsets or combination of subsets of STR loci provides a significant match of identity to an interrogation database entry, and/or the computer program may instruct the processor to perform the determination and resultingly report a significant match.

In another embodiment, the computer readable medium may instruct the processor to form a plurality of partial interrogation identification hashes using the digitized fingerprint scan data of the individual as stored on the identification card and each loci of the DNA data of the interrogation database entry, where the DNA data may not have all of the loci of a complete DNA profile. The computer program may instruct the processor to retrieve a plurality of partial individualized identification hashes stored on the identification card, where the partial individualized identification hashes had been formed from the digitized fingerprint scan data and each of the loci of the DNA profile data of the individual. The computer program may then instruct the processor to compare each of the plurality of partial individualized identification hashes with each of the plurality of partial interrogation database identification hashes. The computer program may instruct the processor to identify matches and may instruct the processor to include notation of which specific loci matched.

In another embodiment, the computer readable medium may instruct the processor to form one or more specific partial interrogation identification hashes using the digitized fingerprint scan data of the individual as retrieved from the identification card and selected loci of the DNA data of the interrogation database entry. For example, the computer program may instruct the processor to determine if a particular subset of loci of DNA data is available in specific interrogation database entry. One non-limiting example is the use of the subset of loci as follows: CS1PO, D7820, D13S317, D16S539, D18S51, D21S11, FGA, D2S1338, and amelogenin. The computer program may instruct the processor to compare specifically selected partial interrogation database identification hashes to a partial individualized identification hash which had been formed from a respective selected subset of DNA loci and the digitized fingerprint scan data. The computer program may instruct the processor to report a match, if identified.

In any embodiment when the database entry may not have a complete DNA profile, the computer program may instruct the processor to return percentage of alleles matched data, and number of loci compared. One of skill may customize the requirements for threshold matching criteria in order to instruct the processor whether the results constitute identification of a significant match.

Alternatively, the computer readable medium may instruct the processor to assign probabilities that the comparisons between the partial individualized identification hashes and the partial interrogation hashes represent a significant likelihood of a match. The computer program may instruct the processor to report a match when these conditions are met.

In other embodiments, the computer readable medium may instruct the processor to issue a result indicating that a less stringently defined association has been found between the interrogation database entry and the individual presenting the identification card. The computer program may further instruct the processor to issue results indicating a potential familial connection, i.e., son, brother, or father, but not an identification permitting confirmation that the individual presenting the card is the same individual whose DNA data is that of the interrogation database entry.

The computer readable medium may instruct a computer that is in or connected to biometric acquisition and processing components used in the enrollment module and/or verification module. The computer readable medium may provide instructions to control the instrumentation to obtain the raw biometric data/images and to process according to the methods described above to form appropriate digitized electronically formatted biometric data of the at least a first class for storage on the identification card. The computer readable medium may also provide instructions to store the raw biometric data/images as graphical biometric data on the identification card. The computer readable medium may provide instructions to control the biometric acquisition and processing components to obtain and process the first and second classes of individualized biometric data to form the first individualized information hash, and store it to the identification card. The computer program may instruct the processor to retrieve respective partial individualized biometric data sets that may be stored on the identification card. The computer readable medium may instruct the processor to retrieve one or more additional partial individualized identification hashes that may be stored on the identification card. In some embodiments, the computer readable medium may instruct the processor to retrieve a plurality of partial individualized identification hashes that may be stored on the identification card. The computer program may instruct the processor to retrieve descriptors of partial individualized identification hashes from the identification card for use in the comparison against equivalent interrogation database biometric data. The computer readable medium may provide instructions to control the biometric acquisition and processing components to obtain and process a third and more classes of individualized biometric data and store it to the identification card. When any of the third and more classes of individualized biometric data includes DNA or DNA, the program may instruct the processor to form an individualized identification hash for each instance of individualized DNA biometric data. The program may further instruct the computer to store any or all of the individualized biometric data and/or individualized identification hashes and/or partial individualized identification hashes to the identification card or a central database, where the central database may include the enrollment database. The program may instruct the instrumentation to also obtain additional classes of biometric data and likewise process for storage on the identification card. In some embodiments, the instructions control the instrumentation to use undigitized data for comparison.

The computer readable medium may provide instructions to store each of the instances of the at least a first class of individualized biometric data, the at least a first individualized identification hash and/or one or more partial individualized identification hashes as a barcode, alphanumerical or a graphical representation. The barcode may be a two dimensional barcode, including but not limited to a matrix barcode. In some embodiments, the computer readable medium may provide instructions to store each of these instances of individualized biometric data on an identification card.

In the verification components of the system, the computer readable medium may instruct the processor to retrieve one or more classes of individualized biometric data from the identification card presented by an individual at a point of contact. The computer program instructs the processor to determine what class(es) of individualized biometric data are retrieved. The computer program instructs the processor to connect to individualized biometric data confirmation components, to acquire biometric data from the individual at the point of contact. The computer readable medium may instruct a computer that is in or connected to biometric acquisition and processing components used in the verification module. The program may provide instructions to control the instrumentation to obtain the raw biometric data/images and to process according to the methods described above to form data useful for comparison with the biometric data of the first class to verify the identity of the individual. The program may instruct the instrumentation to also obtain additional classes of biometric data.

The computer readable medium may instruct the processor to extract each feature and process each feature to present the processed locally acquired biometric data in the same format as the individualized biometric data of class retrieved from the identification card. In some embodiments, the instructions control the instrumentation to use undigitized data for comparison. The computer program may instruct the processor to compare each locally acquired biometric data to the individualized biometric data of the same type, as retrieved from the identification card.

The computer readable medium may instruct the processor to report if the one or more locally acquired biometric data is found to match the one or more individualized biometric data stored on the identification card, and verify the identity of the individual as the individual whose biometric data is stored on the identification card. The computer program then may instruct the processor to initiate a method of identification of the invention, as shown any of the non-limiting examples described herein.

If a match is not found in the one or more classes of biometric data, the computer program may instruct the processor to stop processing the request, and to issue a report that one or more biometric data does not match. Further investigation may be required before any further step of the identification system is taken. The report may include notifying another system and/or authority. The computer program may additionally instruct the processor to initiate an alarm to prevent the individual from leaving the point of contact without further investigation by an authority.

The computer readable medium may provide instructions to a processor which is in or connected to the identification card reader and an enrollment database. The identification card may contain an enrollment verification certification (EVC), wherein the computer readable medium may instruct the processor to retrieve the enrollment verification certification and to interrogate an enrollment database to verify the authenticity of issuance of the identification card. This can be performed in several ways, one of which is to instruct the processor to search for a matching enrollment verification certification, whereupon the processor is further instructed to determine whether other information present on the identification card accompanying the enrollment verification certification matches the record of what was recorded to the card at the time of enrollment. Alternatively, the computer readable medium may instruct the processor to search for the individual to whom the card was issued and to determine whether the enrollment verification certification retrieved from the identification card matches the enrollment verification certification assigned to the card at the time of issuance to the individual. If a match is found, the computer readable medium may instruct the processor to continue the method of identifying the individual. If no match is found, the computer readable medium may instruct the processor to report that no match has been found and the access request process is halted for further investigation. The report may include notifying another system and/or authority. The computer readable medium may instruct the processor to initiate an alarm to prevent the individual from leaving the point of contact without further investigation by an authority.

The computer readable medium may additionally provide instructions to a processor which is in or connected to an identification card read/write component and an enrollment database. The computer readable medium may instruct the processor to assign and deposit a unique enrollment verification certification (EVC) into the enrollment database and stores a copy of the unique enrollment verification certification (EVC) in the identification card, at the time of enrollment.

Any suitable computer-readable medium may be utilized, and may be any tangible storage medium or media having instructions stored thereon or therein which can be used to control, or cause, a computer to perform any of the procedures of the embodiments of the invention. The storage medium may include without limitation a floppy disk, a mini disk, an optical disc, a Blu-ray Disc, a DVD, a CD or CD-ROM, a micro-drive, a magneto-optical disk, a read-only memory (ROM), a random access memory (RAM), an erasable programmable read-only memory (EPROM), an EEPROM, a DRAM, a VRAM, a flash memory, a flash card, a thumb drive (USB), a magnetic card, an optical card, nanosystems, a molecular memory integrated circuit, a RAID, remote data storage/archive/warehousing, and/or any other type of device suitable for storing instructions and/or data. The method for supplying the program(s) includes accessing a home page on the internet using browsing software of a client computer, when the home page allows each user to download the computer programs of the present invention, or compressed files having automatic installing functions, to a hard disk or other recording medium of the user. When information is transferred or provided over a network or another communications connection (either hardwired, wireless, or combination thereof) to a computer, the computer properly views the connection as a computer-readable medium. Combinations of the above should also be included within the scope of the computer-readable medium.

One or more computer-executable program code portions for carrying out operations of the present invention may include object-oriented, scripted, and/or unscripted programming languages, such as, for example, Java, Perl, Smalltalk, C, C++, SAS, SQL, Python, Objective C, and/or the like. The computer program code may alternatively or additionally be written in one or more multi-paradigm programming languages, such as, for example, F #.

A person of ordinary skill in the art, given the benefit of the foregoing description describing the steps to be performed, could implement such a program.

In one embodiment, the invention provides a system for identifying a person, including: an identification card comprising individualized identification information including at least one of a fingerprint data and a retinal scan data, and a DNA data, where one of the fingerprint data and the retinal scan data is hashed together with the DNA data to form an individualized identification hash; and a processor configured to: connect to at least one interrogation database comprising a plurality of interrogation DNA data; interrogate the at least one database wherein each of the plurality of interrogation DNA data is hashed together with the at least one of the fingerprint data and the retinal scan data of the individual to form a plurality of interrogation database identification hashes; compare each of the plurality of interrogation database identification hashes to the personal identification hash; report a match of the database identification hash to the individualized identification hash, if found; and optionally, where the processor is configured to read at least one of the fingerprint data and the retinal scan data at a point of contact, wherein the at least one of the fingerprint data and the retinal scan data is confirmed at the point of contact; and report if a match is not found. Additionally, the identification card may contain an enrollment verification certification, wherein the processor retrieves the enrollment verification certification and interrogates an enrollment database to verify the authenticity of the identification card. The system may further include computer readable instructions, which when executed by the processor, operates on individualized identification information of an individual comprising an individualized biometric data of at least a first class and an individualized identification hash comprising the individualized biometric data of the first class and an individualized biometric data of a second class, and instructs the processor to connect with at least one interrogation database comprising a plurality of interrogation biometric data of the second class; interrogate the at least one interrogation database wherein each of the plurality of interrogation biometric data of the second class is hashed together with the individualized biometric data of the first class to form a plurality of interrogation database identification hashes; compare each of the plurality of interrogation database identification hashes to the individualized identification hash; and report whether a match of the interrogation database identification hash to the individualized identification hash is found.

Methods of Use for the System of the Invention.

The identification systems, which may or may not include verification components and/or enrollment components, may be used in many methods of identification of an individual. Individualized identification information, including individualized biometric data, of any class, combination, or format as described for the identification card and identification system may be used in the methods of the invention.

Figure 4A:
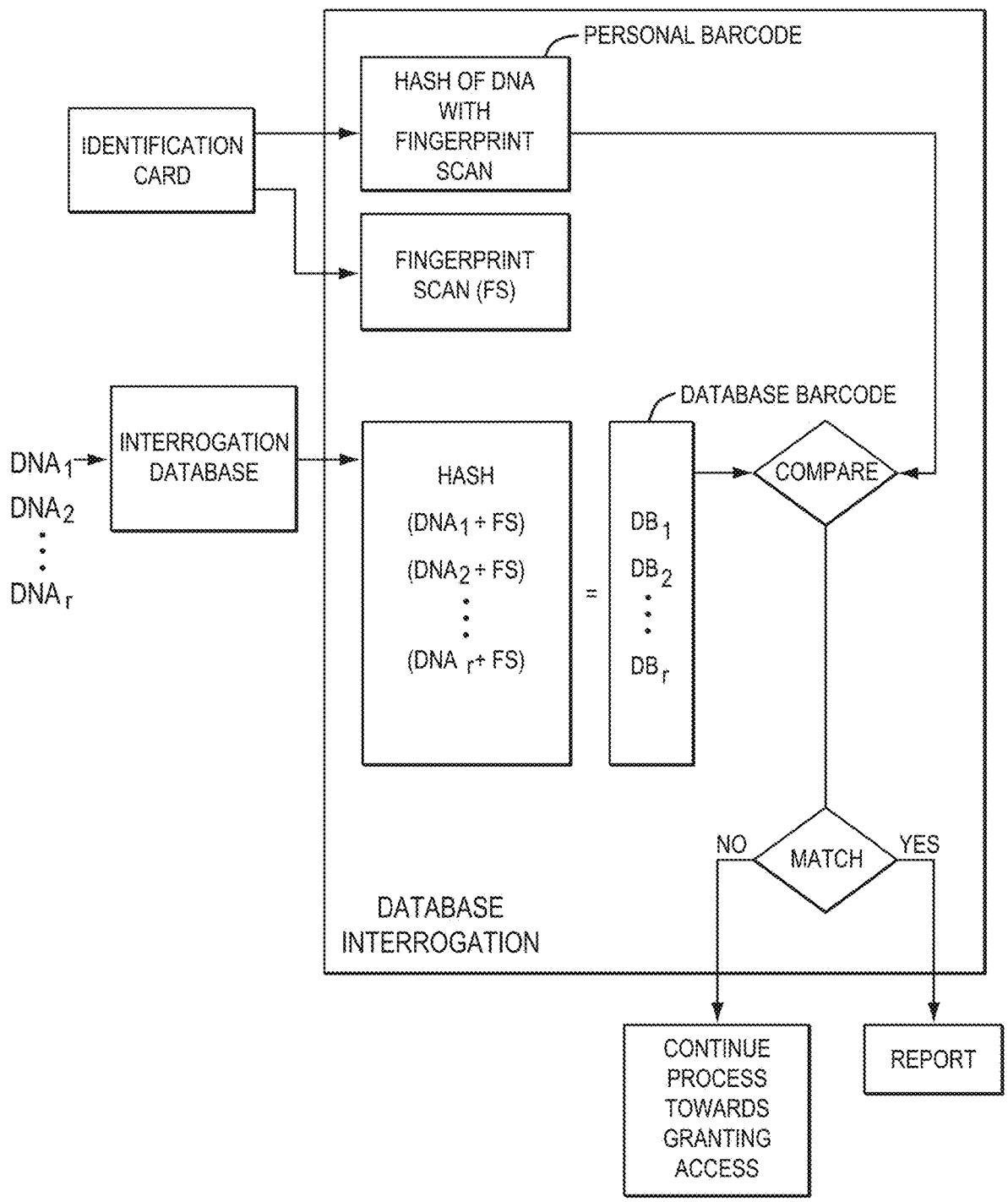
FIG. 4A is a schematic representation of an embodiment of the database interrogation of the present invention.

One embodiment of a method 400A of identification of an individual is shown in FIG. 4A. An individual presents an identification card 420 when requesting access to an entity, transport, information, location, security organization, law enforcement organization, transaction, services, authorized status, or funds. The identification card includes individualized identification information which includes individualized biometric data which is retrieved and read for use in the methods of identification. In some embodiments, the identification card does not have the individualized biometric data present in the local device presented at the point of contact. The individualized biometric data may be retrieved from a remote database upon entry of a password or other electronic entry permission granting procedure for any of the following steps of the methods of identification, verification and/or enrollment. In some embodiments, the remote database may be the enrollment database.

A first individualized identification hash (IIH, 402), formed from an individualized biometric data of a first class and an individualized biometric data of a second class, and an individualized biometric data of the first class (IDBI, 403) may be retrieved from the identification card 420. The processor may retrieve the individualized identification hash 402 and the individualized biometric data of the first class 403 from the identification card and may determine what classes of biometric data are included. Any suitable class of biometric data may be used, as described for the identification card of the system. When any class of individualized biometric data is a DNA data, then the DNA individualized biometric data is stored in a hashed form. In some embodiments, the hash is a one-way hash. The processor may optionally include the step of converting the individualized biometric data of the first class to a digitized individualized biometric data, if it had been stored as a graphical individualized biometric data, alphanumeric representation or a barcode, on the identification card. The processor may access at least one interrogation database ($470_1$ to $470_n$) which contains a plurality of interrogation biometric data of the second class wherein each of the plurality of interrogation biometric data of the second class may have an interrogation database identifier ($NDB_1$ to $NDB_r$ and $NDB_{r+1}$ to $NDB_{r+s}$, ($404_1$ to $404_r$ and $404_{r+1}$ to $404_{r+s}$)). The processor may retrieve the plurality of interrogation biometric data of the second class and, if necessary, reorder each of the plurality of interrogation biometric data of the second class to be presented in the same order and manner as that of the individualized biometric data of the second class. The processor may hash each of the plurality of interrogation biometric data of the second class ($404_1$ to $404_r$ and $404_{r+1}$ to $404_{r+s}$) together with the individualized biometric data of the first class 403 to form a plurality of interrogation database identification hashes ($IDIH_1$ to $IDIH_r$ and $IDIH_{r+1}$ to $IDIH_{r+s}$ (element nos. $405_1$ to $405_r$ and $405_{r+1}$ to $405_{r+s}$)). Each of the plurality of interrogation database identification hashes ($405_1$ to $405_r$ and $405_{r+1}$ to $405_{r+s}$) may be compared (406) to the individualized identification hash (IDH, 402). A report may be issued whether a match of one or more of the interrogation database identification hashes to the individualized identification hash (409) is found. If no match is found, the individual may continue the process towards access to the entity, transport, information, location, security organization, law enforcement organization, transaction, services, authorized status, or funds (408). When a match is identified, then a report 409 is issued concluding that a match was identified and may require further investigation of the individual before any further steps may be taken in the request for access.

Figure 4B:
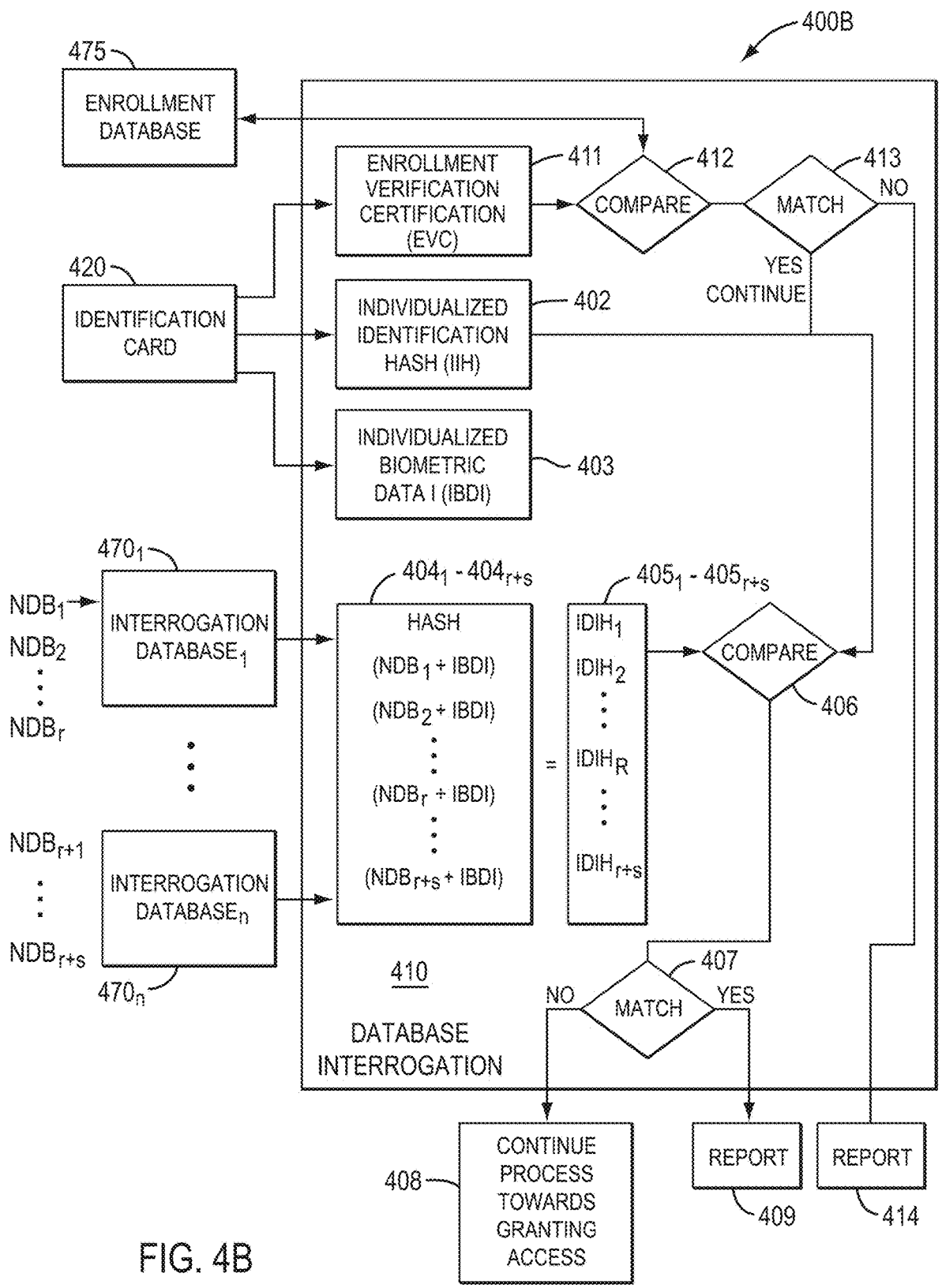
FIG. 4B is a schematic representation of an embodiment of the database interrogation of the present invention.

Other embodiments of methods, 400B, of identification of an individual are shown in FIG. 4B. An individual presents an identification card 420 when requesting access to an entity, transport, information, location, security organization, law enforcement organization, transaction, services, authorized status, or funds. The processor may retrieve an enrollment verification certification 411 from the identification card, and interrogate the enrollment database 475. This can be performed in several ways, one of which is to search for a matching enrollment verification certification, whereupon the processor may further determine whether the other information present on the identification card 420 accompanying the enrollment verification certification 411 matches (412) the record of what was stored in the card 420 at the time of enrollment. Alternatively, the processor can search for the individual to whom the card 420 was issued and may determine whether the enrollment verification certification 411 retrieved from the identification card 420 matches (412) the enrollment verification certification assigned to the card at the time of issuance to the individual. If a match is found, the method of identifying the individual continues. If no match is found, the processor may report (414) that no match has been found and the access request process is halted for further investigation. The report (414) may include notifying another system and/or authority. The processor may additionally initiate an alarm to prevent the individual from leaving the point of contact without further investigation by an authority.

A first individualized identification hash (IIH, 402), formed from an individualized biometric data of a first class and an individualized biometric data of a second class, and an individualized biometric data of the first class (IDBI, 403) may be retrieved from the identification card 420 by the processor. Any suitable class of biometric data may be used, as described for the identification card of the system. When any class of individualized biometric data is a DNA data, then the DNA individualized biometric data is stored in a hashed form. In some embodiments, the hash is a one-way hash. The processor may access at least one interrogation database ($470_1$ to $470_n$) which contains a plurality of interrogation biometric data of the second wherein each of the plurality of interrogation biometric data of the second class has an interrogation database identifier class ($NDB_1$ to $NDB_r$ and $NDB_{r+1}$ to $NDB_{r+s}$, element nos. ($404_1$ to $404_r$ and $404_{r+1}$ to $404_{r+s}$)). The processor may hash each of the plurality of interrogation biometric data of the second class together with individualized biometric data of the first class to form a plurality of interrogation database identification hashes ($IDIH_1$ to $IDIH_r$ and $IDIH_{r+1}$ to $IDIH_{r+s}$, element nos. ($405_1$ to $405_r$ and $405_{r+1}$ to $405_{r+s}$)). Each of the plurality of interrogation database identification hashes ($405_1$ to $405_r$ and $405_{r+1}$ to $405_{r+s}$) may be compared (406) to the individualized identification hash (IIH, 402). Any match of one or more of the interrogation database identification hashes to the individualized identification hash may be reported (409). The access request process may be halted for further investigation of the individual. The report (414) may include notifying another system and/or authority. The processor may additionally initiate an alarm to prevent the individual from leaving the point of contact without further investigation by an authority.

If no match (407) is found, the individual may continue the process towards access to the entity, transport, information, location, security organization, law enforcement organization, transaction, services, authorized status, or funds (408).

In another embodiment of a method of identification, the processor may retrieve the individualized biometric data of the first class, which is compared directly to interrogation database entries of the same class. This may be performed either independently or along with the comparison of interrogation database identification hashes formed from biometric data of the second class, as described above. In yet other embodiments, the individualized biometric data of the third or more class is retrieved from the identification card and matched with interrogation database biometric data of the equivalent class. Any suitable class of biometric data may be used, as described for the identification card of the system. If the individualized biometric data of the third or more class is a DNA data and is present as a second or more individualized identification hash, it is compared with interrogation database identification hashes formed as described above for the individualized biometric data of the second class, and using steps of comparison as described as suitable for the individualized biometric data of the second class. If matches of the individualized biometric data of the first class or of the third or more class are identified, a report may be issued and the access request process may be halted for further investigation of the individual.

Figure 4C:
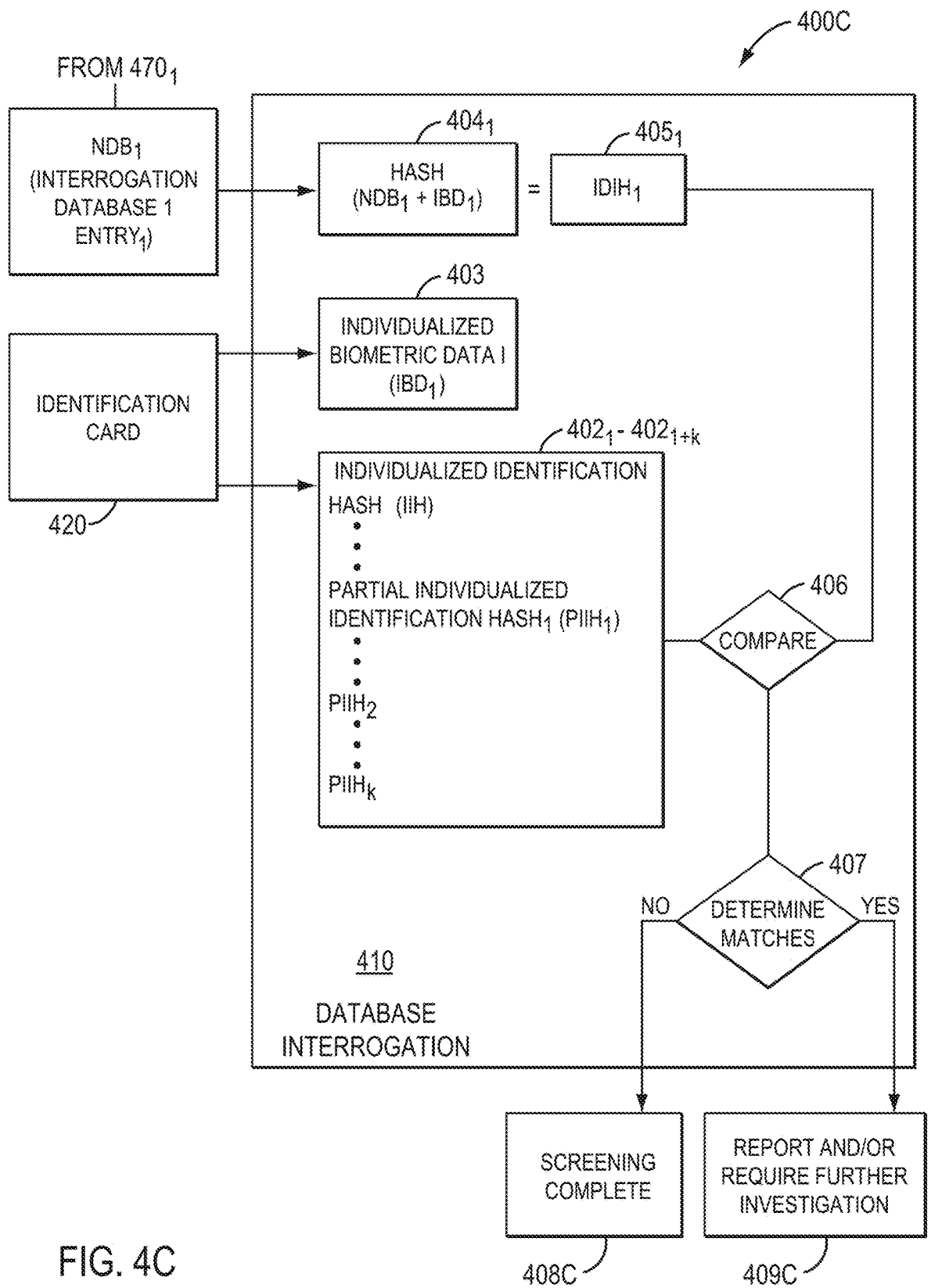
FIG. 4C is a schematic representation of an embodiment of the database interrogation of the present invention.
Figure 4D:
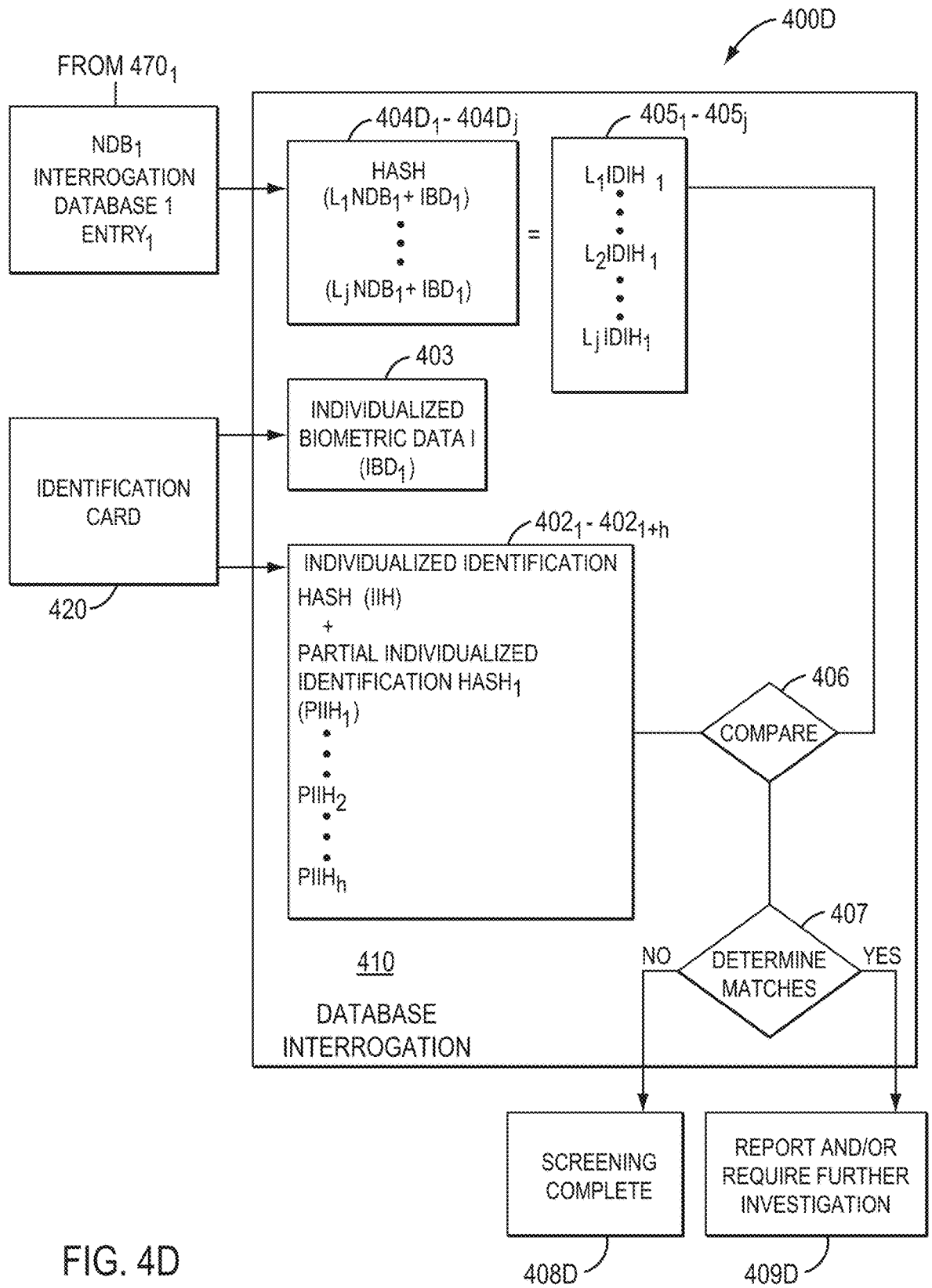
FIG. 4D is a schematic representation of an embodiment of the database interrogation of the present invention.

Other embodiments of methods, 400C and 400D, of identification of an individual are shown in FIG. 4C and FIG. 4D. The method of identification of an individual may be performed using partial DNA profiles. This may occur when the at least one interrogation database has incomplete or degraded DNA profile entries. In some embodiments, it may be determined whether at least one interrogation database contains interrogation biometric data which may be incomplete, degraded, or has portions of the biometric data obscured by contaminants. It may additionally determine what portions of interrogation biometric data are available for comparison with individualized biometric data. As shown in FIG. 4C, one embodiment 400C of the method includes an identification card 420 presented by the individual may have a plurality of partial individualized identification hashes formed from individualized biometric data of the first class with partial DNA profiles ($PIIH_1$ to $PIIH_k$), along with the first individualized identification hash formed from the individualized biometric data of the first class and the individualized biometric data of the second class which is a DNA profile (IIH). In some embodiments, the hash is a one-way hash. In one non-limiting example, the individualized biometric data of the first class is a fingerprint scan data or an iris scan data. The plurality of partial individualized identification hashes may be formed from each DNA profile component contributing to the DNA profile as acquired for the individual. For example, a plurality of individualized identification hashes may be formed using each DNA STR locus separately, or every combination of subsets, or any selection of such grouping of DNA STR loci. One non-limiting example is the use of the subset of SNA STR loci as follows: CS1PO, D7820, D13S317, D16S539, D18S51, D21S11, FGA, D2S1338, and amelogenin. A partial individualized identification hash used in the comparison with partial interrogation database DNA biometric data may be formed from a subset of two or more, three or more, four or more, five or more, six or more, seven or more, or eight or more STR loci. Optionally, the identification card may include descriptors of the loci used to form the partial individualized identification hashes for comparison against equivalent interrogation database biometric data.

Each of the plurality of partial individualized identification hashes ($PIIH_1$ to $PIIH_k$) may be compared (406) to a potentially partial interrogation database identification hash ($IDIH_1$) formed from the individualized biometric data of the first class ($IBD_1$) and a potentially incomplete or partial DNA STR data entry of the at least one interrogation database ($NDB_1$). In some embodiments, comparison (406) between the first individualized identification hash (IIH) and the interrogation database identification hash ($IDIH_1$) is also performed. In other embodiments of the method, comparison (406) of the plurality of partial individualized identification hashes ($PIIH_1$ to $PIIH_k$) to the interrogation database identification hash ($IDIH_1$) is performed without the first individualized identification hash (IIH) being compared to the interrogation database identification hash ($IDIH_1$).

A report (409) may be issued for any matches found between any of the plurality of individualized identification hashes (complete or partial, element nos. ($402_1$ to $402_{1+k}$) and the interrogation database identification hash. The report may include whether the complete set of STR loci (as contained in IIH) or which subset or subsets of STR loci (as contained in $PIIH_1$ to $PIIH_k$) provided a match, as the identity of the STR loci may be identifiable without revealing the individual's alleles, thus still providing privacy. A match may be reported when the partial individualized identification hash used in the comparison is formed from a subset of two or more STR loci. In other embodiments, a match may be reported when the partial individualized identification hash used in the comparison is formed from a subset of three or more, four or more, five or more, six or more, seven or more, or eight or more STR loci. In other embodiments, a match may be reported when more than one partial individualized identification hash matches the partial interrogation database identification hash. One of skill may determine which subsets or combination of subsets of STR loci provides a significant match of identity to an interrogation database entry, and/or the computer program may instruct the processor to perform the determination and resultingly report a significant match. Alternatively, if no matches were found, with any of the group of individualized hashes, screening of the interrogation database entry ($NDB_1$) is complete. The process of forming an interrogation database identification hash with the next entry in the interrogation database ($NDB_2$); comparing the resulting interrogation database identification hash $IDIH_2$ with the plurality of individualized identification hashes ($402_1$ to $402_{1+k}$); and reporting whether any matches were identified.

In another embodiment 400D as shown in FIG. 4D, another method to identify an individual is described. A plurality of partial interrogation identification hashes ($L_1IDIH_1$ to $L_jIDIH_1$, elements $405_1$-$405_j$) may be formed using the individualized biometric data of the first class ($IBD_1$) of the individual and each loci of the DNA data ($L_1NDB_1$ to $L_jNDB_1$, elements $404_1$-$404_j$) of the interrogation database entry ($NDB_1$), where the DNA data may not have all of the loci of a complete DNA profile, as acquired for the individual at the time of enrollment. A plurality of partial individualized identification hashes ($PIIH_1$ to $PIIH_h$) are retrieved, where the partial individualized identification hashes had been formed from the individualized biometric data of the first class ($IBD_1$) and each of the loci of the DNA profile data of the individual, having a total of h loci. Each of the plurality of partial individualized identification hashes ($PIIH_1$ to $PIIH_h$) may be compared with each of the plurality of partial interrogation database identification hashes ($L_1IDIH_1$ to $L_jIDIH_1$, elements $405_1$-$405_j$). Matches can be identified and reported and the report may include notation of which specific loci matched. A report may also include a conclusion of finding a significant match. If no matches are found, a report indicating that screening of the interrogation database entry ($NDB_1$) is complete. The steps of this method may be repeated for every interrogation database entry, $NDB_1$ to $NDB_r$ and similarly for every other database to be interrogated.

In another embodiment of the method of FIG. 4D, one or more specific partial interrogation identification hashes may be formed using the individualized biometric data of the first class ($IBD_1$) of the individual and selected loci of the DNA data of the interrogation database entry. For example, it may be determined if a particular subset of loci of DNA data is available in specific interrogation database entry ($NDB_1$). One non-limiting example is the use of the subset of loci as follows: CS1PO, D7820, D13S317, D16S539, D18S51, D21S11, FGA, D2S1338, and amelogenin. Such a specifically selected partial interrogation database identification hash may be formed from the individualized biometric data of the first class ($IBD_1$) of the individual and the specifically selected subset of loci of the interrogation database entry ($NDB_1$), and compared to a partial individualized identification hash (for example a $g^{th}$ partial individualized identification hash, $PIIH_g$) of the total of k partial individualized identification hashes of FIG. 4C which had been formed from a respective selected subset of DNA loci and the individualized biometric data of the first class ($IBD_1$) of the individual. Matches may be reported as described above. One of skill may determine specific combinations of selected subsets of STR loci of DNA data that provide useful matches for reporting. Selected combinations of selected subsets may not require every loci of a complete STR DNA panel to be present in the interrogation database entry, while still providing a statistically significant match.

In various embodiments, comparison of the individualized identification hash (IIH) with each of the plurality of partial interrogation database identification hashes ($L_1IDIH_1$ to $L_jIDIH_1$) may or may not be performed when partial individualized identification hashes are compared to partial interrogation database identification hashes ($L_1IDIH_1$ to $L_jIDIH_1$).

In any embodiment when the database entry may not have a complete DNA profile, a report may issue including percentage of alleles matched data, and number of loci compared. One of skill may customize the requirements for threshold matching criteria in order to determine whether the results constitute identification of a significant match.

Alternatively, the processor may assign probabilities that the comparisons between the partial individualized identification hashes and the partial interrogation data hashes represent a significant likelihood of a match. A match may be reported when these conditions are met.

In other embodiments, a report may be issued indicating that a less stringently defined association has been found between the interrogation database entry and the individual presenting the identification card. The report may indicate a potential familial connection, i.e., son, brother, or father, but not an identification permitting confirmation that the individual presenting the card is the same individual whose DNA data is that of the interrogation database entry.

In any of the embodiments of the methods of identification, each of the instances of the at least a first class of individualized biometric data, the at least a first individualized identification hash and/or one or more partial individualized identification hashes may be retrieved as a barcode, alphanumerical or a graphical representation. The barcode may be a two dimensional barcode, including but not limited to a matrix barcode. In some embodiments, each of these instances of individualized biometric data is retrieved from an identification card.

Figure 5A:
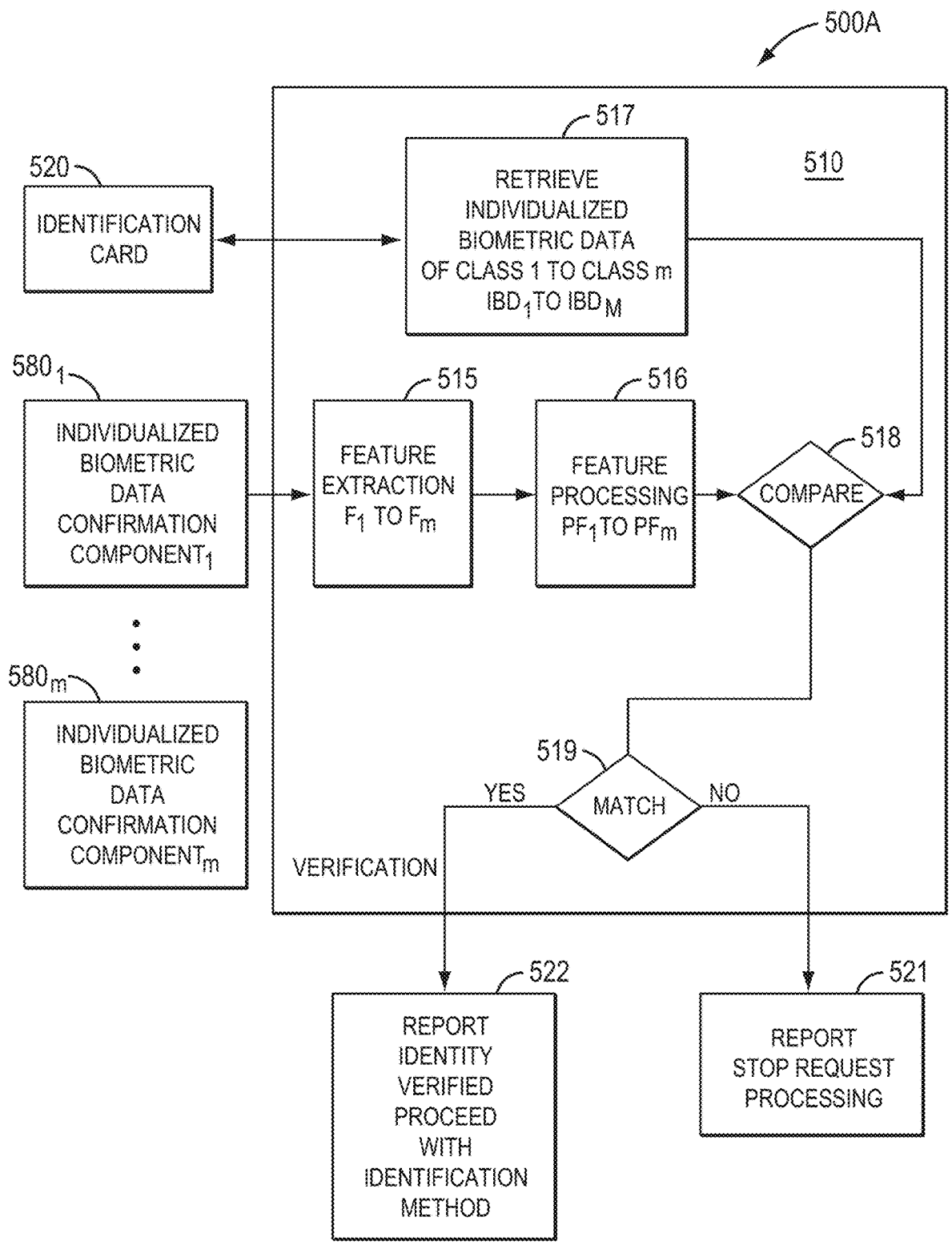
FIG. 5A is a schematic representation of an embodiment of the verification component of the present invention.

Verification. In other embodiments, steps including verification are performed at the same time or prior to the identification methods. The verification method steps are shown schematically in FIGS. 5A and 5B. A first class, or more, of individualized biometric data ($IBD_1$ to $IBD_M$) is retrieved from the identification card 520 presented by an individual at a point of contact. The processor determines what classe(s) of individualized biometric data are retrieved (517). The processor connects to individualized biometric data confirmation components 1-m ($580_1$-$580_m$), and acquires each of 1-m biometric data from the individual at the point of contact. The processor extracts each feature $F_1$ to $F_m$ (515) and processes each feature (516) to present each $F_1$ to $F_m$ in the same format, digitized or undigitized, hashed or not hashed, and with any further processing necessary to present the processed locally acquired biometric data $PF_1$ to $PF_m$ in the same format as the individualized biometric data of class I to class M. Each locally acquired biometric data is compared (518) to the individualized biometric data of the same type, as retrieved from the identification card 520.

If the one or more locally acquired biometric data is found to match (519) the one or more individualized biometric data stored on the identification card, a report (522) may be sent verifying the identity of the individual as the individual whose biometric data is stored on the identification card. The method of identification of the invention is then initiated, as shown any of the non-limiting examples described herein.

If a match (519) is not found in one or more classes of biometric data, the request processing is stopped, a report (521) is sent, and further investigation may be required before any further step of the identification system is taken.

Figure 5B:
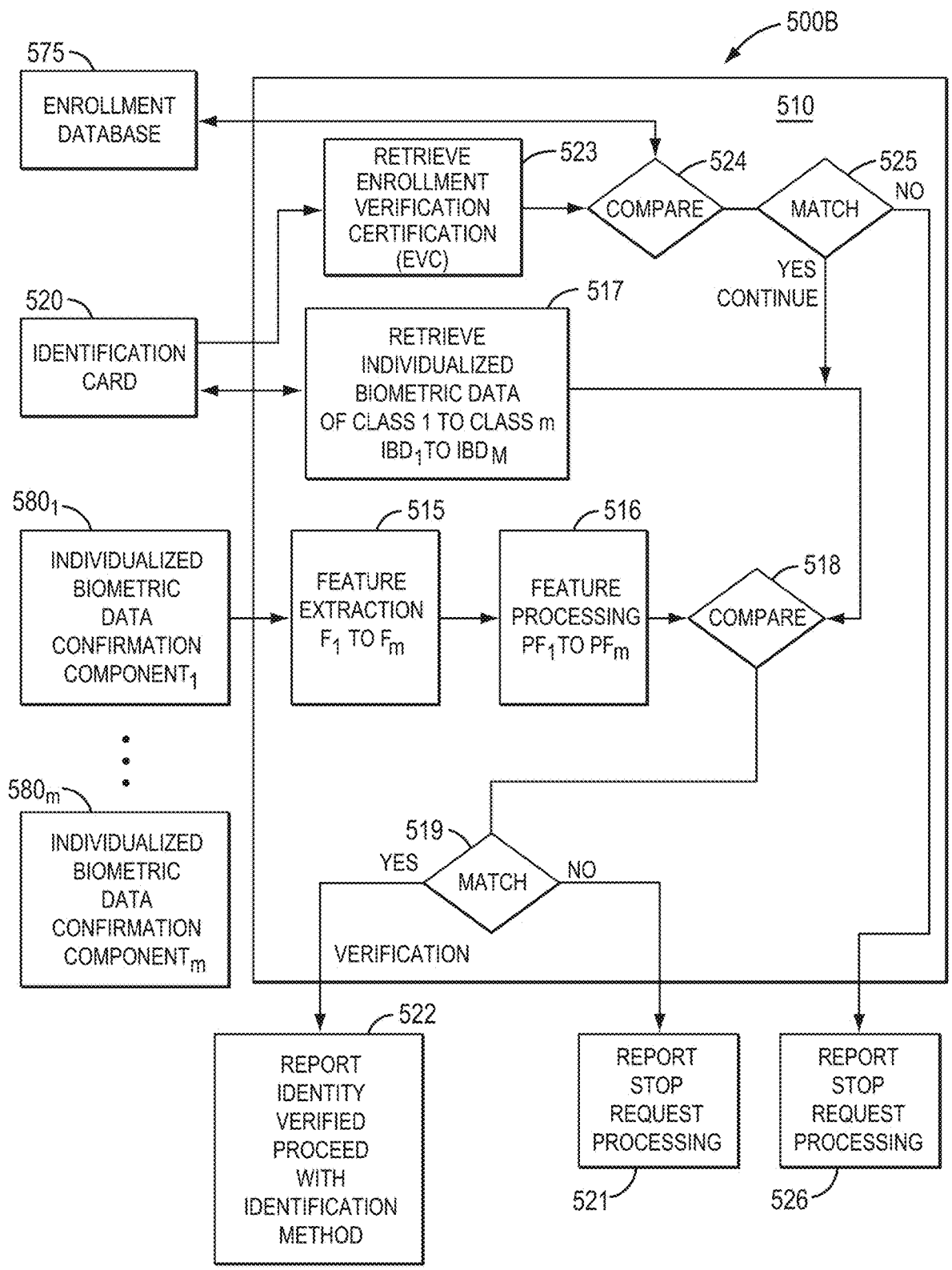
FIG. 5B is a schematic representation of an embodiment of the verification component of the present invention.

FIG. 5B shows another embodiment of verification methods, which, in addition to the steps discussed above for FIG. 5A, adds the steps of retrieving (523) an enrollment verification certification (EVC) from the identification card. The enrollment database 575 is interrogated. This can be performed in several ways, one of which is to search for a matching enrollment verification certification, whereupon the processor further determines whether the other information present on the identification card 520 accompanying the enrollment verification certification EVC matches (525) the record of what was recorded to the card 520 at the time of enrollment. Alternatively, the processor can search for the individual to whom the card 520 was issued and determine whether the enrollment verification certification EVC retrieved from the identification card 520 matches (525) the enrollment verification certification assigned to the card at the time of issuance to the individual. If a match is found, the method of verifying the identity of the individual at the point of contact continues, as described in the equivalent steps of the method of FIG. 5A. If no match is found, the processor reports (526) that no match has been found and the access request process is halted for further investigation. The report (526) may include notifying another system and/or authority. The processor may additionally initiate an alarm to prevent the individual from leaving the point of contact without further investigation by an authority.

Enrollment to Obtain an Identification Card by an Individual.

As part of enrollment, an individual is required to submit two or more types of biometric data. A schematic of several embodiments of enrollment are depicted in FIGS. 6A, 6B, 7A and 7B.

Figure 6A:
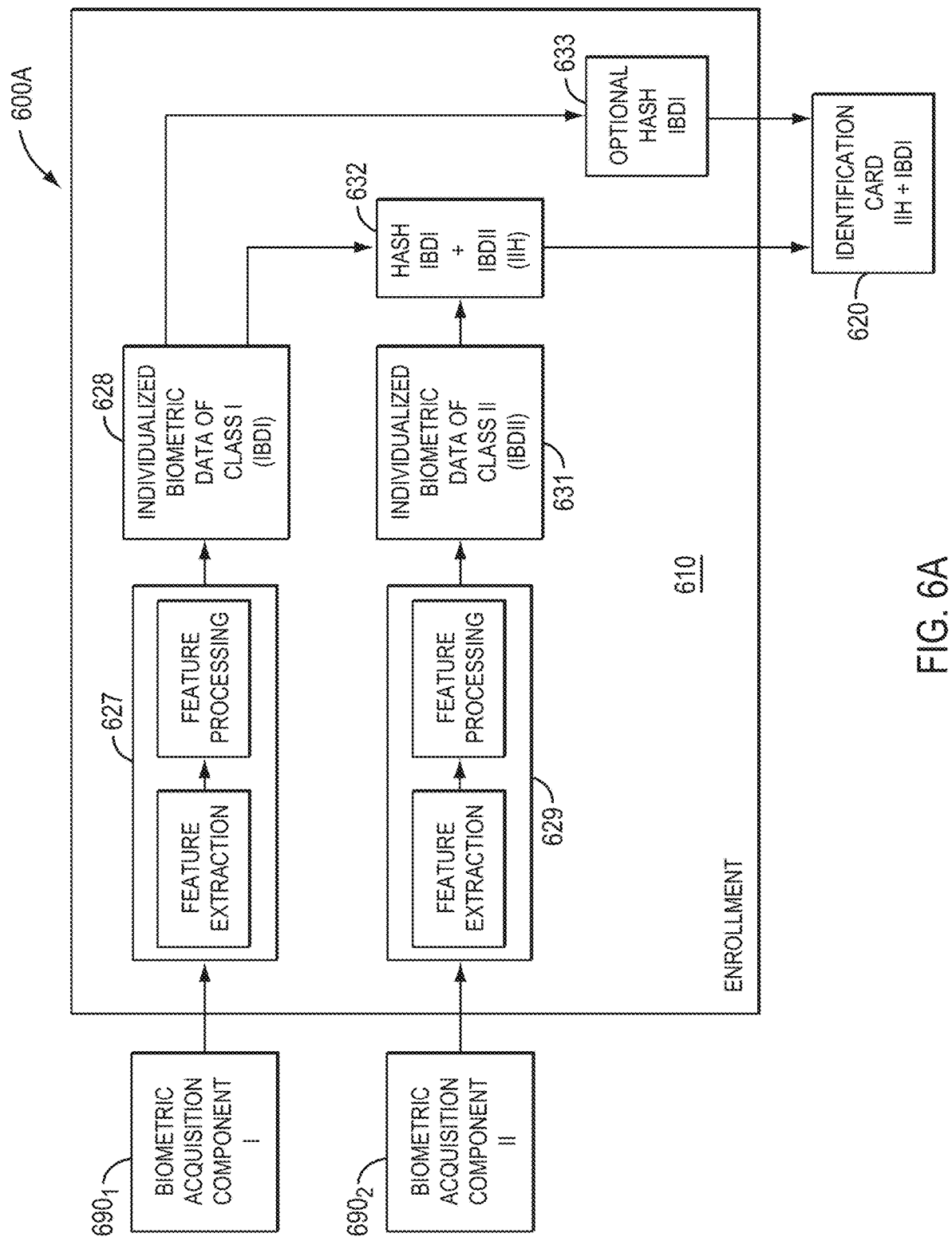
FIG. 6A is a schematic representation of an embodiment of an enrollment method according to the present invention.

In any embodiments, where the identification card itself does not carry individualized identification information including the individualized biometric data of the individual, a password or other electronic entry permission granting device is stored on the card. This permits the retrieval of the individualized identification information, upon presentation of the identification card at the point of contact, from another database, which may be the enrollment database. As shown in FIG. 6A, biometric data of the first class is collected by biometric data acquisition component I ($690_1$) and converted to a digital electronic format (627). Some examples of suitable biometric data of the first class include, but are not limited to fingerprints and palmprints; body geometry features, including but not limited to ear, hand, finger, and the like; facial features; face images; voice; voice prints; optical recognition, including but not limited to iris scans and retinal scans; infrared identification, including but not limited to face, hand, and handvein; and the like. In one embodiment, one instance of the biometric data of the first class (IBDI) is stored on the identification card, in the digitized electronic format (628). In some embodiments, the biometric data of the first class (IBDI) is hashed in an invertible form prior to storage on the card (633). In other embodiments, the biometric data of the first class (IBDI) is hashed in a non-invertible form prior to storage on the card (633). In some embodiments other post processing of the electronically digitized biometric data of the first class (IBDI) is performed. In other embodiments no post processing of the electronically digitized biometric data of the first class (IBDI) is performed. In yet other embodiments, the biometric data of the first class (IBDI) is stored with no further processing after the initial acquisition, i.e. as a raw image of a biometric data, including but not limited to a fingerprint scan data, a retinal scan data and an iris scan data. In other embodiments, a second instance of the biometric data of the first class is stored on the identification card, where the second instance is stored in a different format than the first instance. In one non-limiting example, a fingerprint scan data may be stored in both a graphical representation and additionally, in a digitized representation.

Many kinds of algorithms may be used to convert graphical scan data such as fingerprint, iris, retina, facial feature recognition, body geometry and others into digitized representations (templates), and the specific disclosure provided herein is not meant to be limiting.

The second class of biometric data is obtained by biometric data acquisition component II (690₂), and may be one of any class of biometric data. When the second class of biometric data is nucleic acid, i.e. either DNA or RNA, a sample of the individual's DNA is collected and analyzed (690₂). The results are converted to a digital electronic format (629). The digitized individualized biometric data of the second class (IBDII) is hashed with the electronically digitized first class of biometric data (IBDI) of the individual (631) to produce an individualized identification hash (IIH). In some embodiments the hashing process is invertible. In other embodiments, the hashing process is noninvertible. Only the individualized identification hash (IIH, 632) is stored on the identification card (620).

Figure 6B:
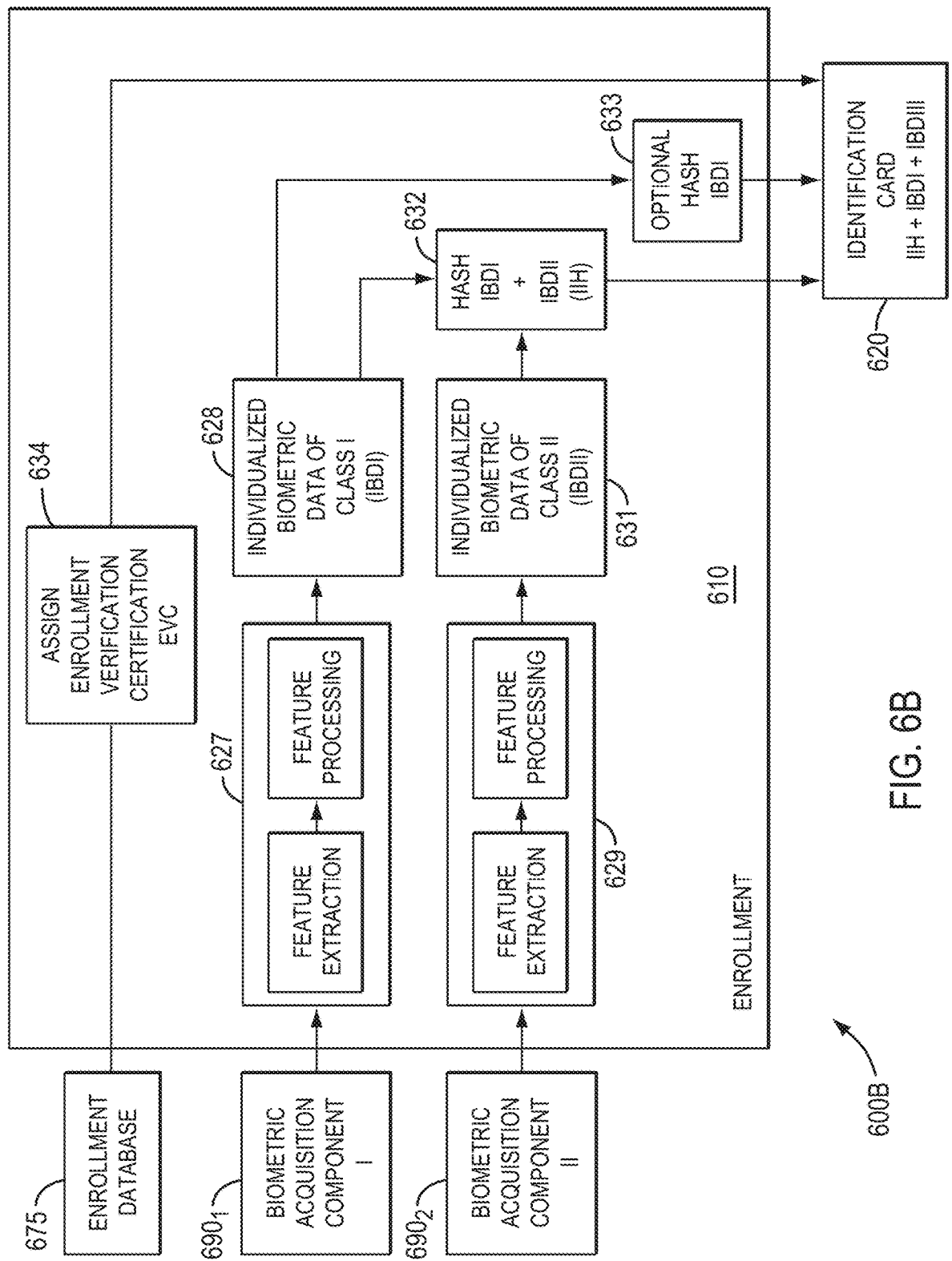
FIG. 6B is a schematic representation of an embodiment of an enrollment method according to the present invention.

In other embodiments, as shown in FIG. 6B, along with the steps described in the embodiments 600A, an additional process is added to the enrollment methods. The processor, at the time of enrollment, additionally assigns (634) and deposits a unique enrollment verification certification (EVC, 611) into the enrollment database and stores a copy of the unique enrollment verification certification (EVC) in the identification card 620. The enrollment verification certification can be retrieved at the point of contact when the individual requests access to an entity, transport, information, location, security organization, law enforcement organization, transaction, services, authorized status, or funds to assure that the card was issued from the enrollment database, as discussed above.

Additional classes of biometric data may also be obtained from the individual (FIGS. 7A and 7B), for example, fingerprints and palmprints; body geometry features, including but not limited to ear, hand, finger, and the like; facial features; face images; voice; voice prints; optical recognition, including but not limited to iris scans and retinal scans; infrared identification, including but not limited to face, hand, and handvein; and the like. In some embodiments the additional classes of biometric data include nucleic acids data. The biometric data of the first class is collected by biometric data acquisition component I (790₁) and converted to a digital electronic format (735), as discussed above for the embodiments of FIGS. 6A and 6B, and including the same classes of biometric data. One instance of the biometric data of the first class (IBDI) is stored on the identification card, in the digitized electronic format. The digitized electronic biometric data of the first class (IBDI) may have been further processed (744) as discussed for the embodiments of FIGS. 6A and 6B, prior to storage on the identification card 720. The second class of biometric data is obtained by biometric data acquisition component II (790₂), and may be one of any class of biometric data. When the second class of biometric data is nucleic acid, i.e. either DNA or RNA, a sample of the individual's DNA is collected and analyzed (790₂). The second class of biometric data is processed (737) as in the embodiments of FIGS. 6A and 6B.

The digitized individualized biometric data of the second class (IBDII) is hashed with electronically digitized first class of biometric data (IBDI) of the individual (739) to produce an individualized identification hash (IIH). In some embodiments the hashing process is invertible. In other embodiments, the hashing process is noninvertible. Only the individualized identification hash (IIH, 739) is stored on the identification card (720).

The third or more classes of biometric data are acquired by biometric acquisition component III (790₃), and so forth. The third or more classes of biometric data may be converted to a digital electronic format (IBDIII, 741). The third or more classes of biometric data may be hashed before storage on the identification card (743). In some embodiments the hash of the third or more classes of biometric data is invertible. In other embodiments the hash of the third or more classes of biometric data is non-invertible. In some embodiments other post processing of the electronically digitized biometric data of the third or more class is performed. In other embodiments no post processing of the electronically digitized biometric data of the third or more class is performed.

When a biometric data including a nucleic acids profile, either DNA or RNA, is used, for example as a biometric data of the third or more class, it may also be hashed with the electronically digitized biometric data of the first class, prior to storage on the identification card. In some embodiments, the hashing of the DNA or RNA containing third class of biometric data and the first class of biometric data is invertible. In other embodiments, the hashing of the DNA or RNA containing third class of biometric data and the first class of biometric data is non-invertible. The individualized biometric data of the first class (IBDI), individualized identification hash (IIH) and the individualized biometric data of the third class (IBDIII) are stored on the identification card 720, and so on for any additional classes of individualized biometric data. The individualized biometric data of the third class may be of the form of an individualized identification hash.

Figure 7A:
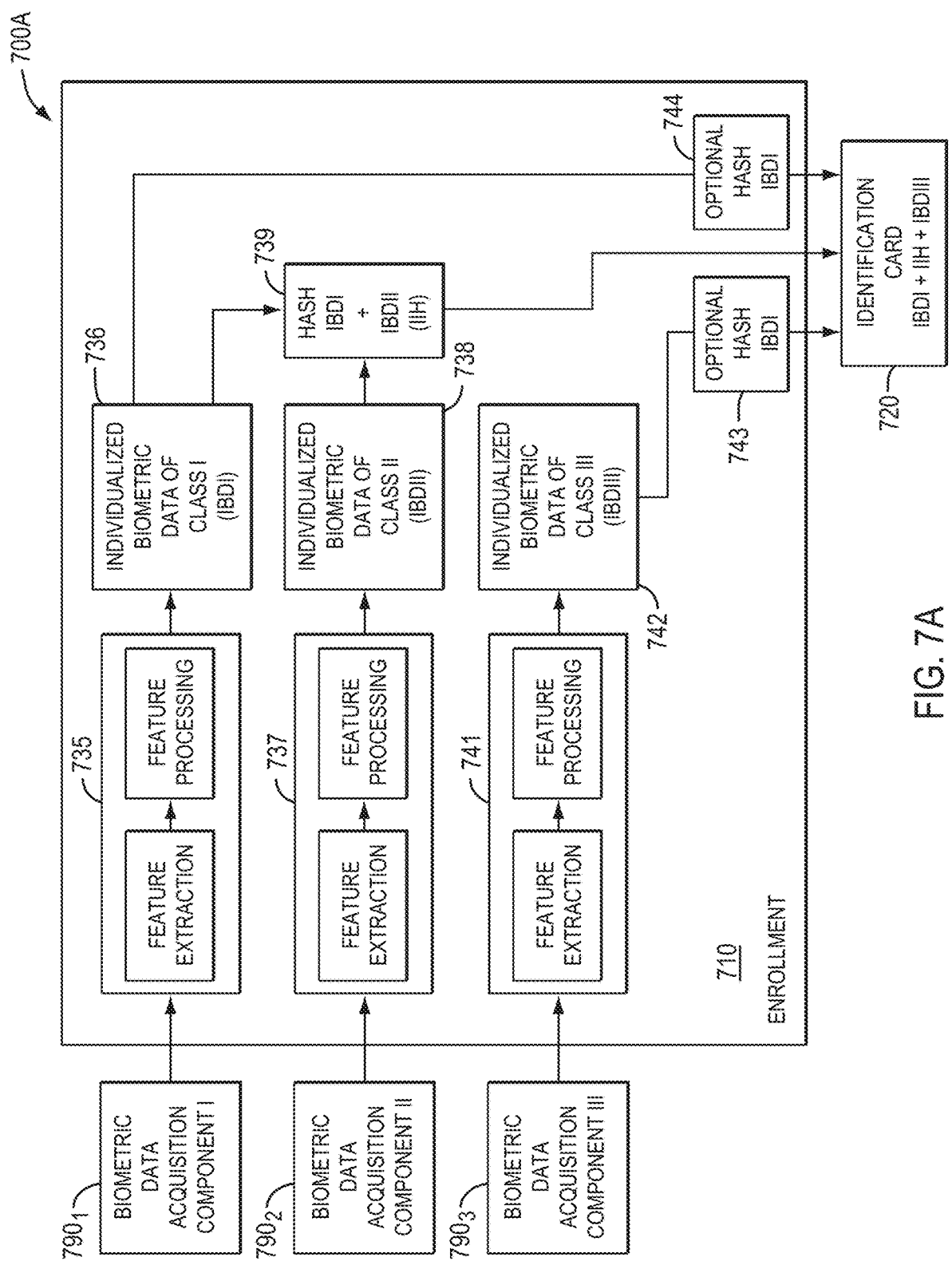
FIG. 7A is a schematic representation of an embodiment of another enrollment method according to the present invention.
Figure 7B:
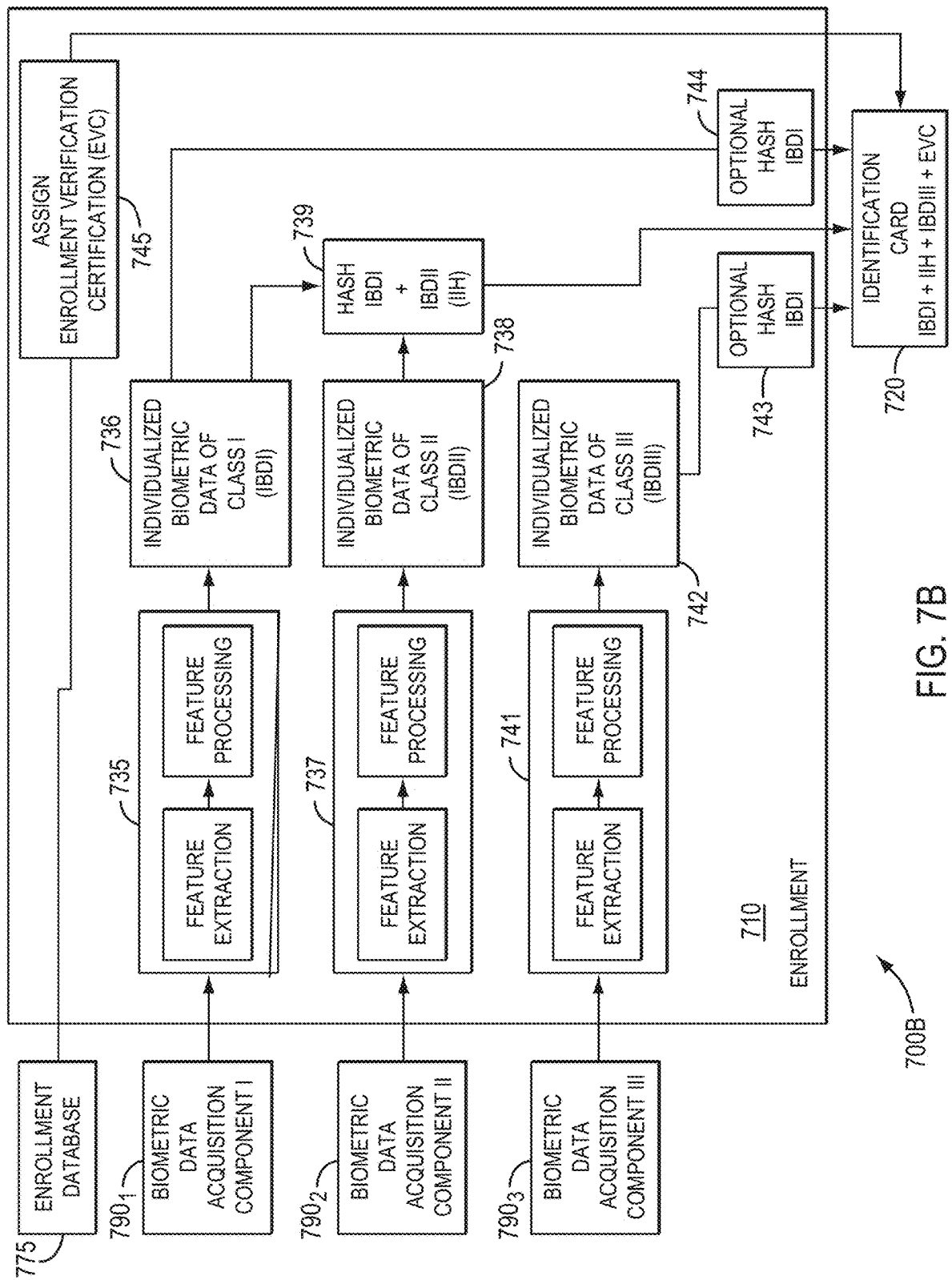
FIG. 7B is a schematic representation of an embodiment of another enrollment method according to the present invention.

In other embodiments of the method, as shown in FIG. 7B, along with the steps described in the embodiments FIG. 7A (700A), an additional process is added to the enrollment methods. The processor, at the time of enrollment, additionally assigns (745) and deposits a unique enrollment verification certification (EVC) into the enrollment database and stores a copy of the unique enrollment verification certification (EVC) in the identification card 720. The enrollment verification certification can be retrieved at the point of contact when the individual requests access to an entity, transport, information, location, security organization, law enforcement organization, transaction, services, authorized status, or funds to assure that the card was issued from the enrollment database, as discussed above.

In any of the embodiments of the enrollment methods, a plurality of partial individualized identification hashes may be formed from each of the individual DNA profile components contributing to a complete DNA profile, and stored on the identification card. For example, a plurality of individualized identification hashes may be formed using each DNA STR locus separately, or every combination of subsets, or any selection of such grouping of DNA STR loci. One non-limiting example is the use of the subset of SNA STR loci as follows: CS1PO, D7820, D13S317, D16S539, D18S51, D21S11, FGA, D2S1338, and amelogenin. A partial individualized identification hash used in the comparison with partial interrogation database DNA biometric data may be formed from a subset of two or more, three or more, four or more, five or more, six or more, seven or more, or eight or more STR loci. Optionally, descriptors of these partial individualized identification hashes may be stored on the identification card during enrollment, for comparison against equivalent interrogation database biometric data in any of the methods of identification.

In any of the embodiments of the methods of enrollment, each of the instances of the at least a first class of individualized biometric data, the at least a first individualized identification hash and/or one or more partial individualized identification hashes may be as a barcode, alphanumerical or a graphical representation. The barcode may be a two dimensional barcode, including but not limited to a matrix barcode.

Methods of Converting Biometric Data for Storage on the Identification Card and for Comparison Between Individualized Biometric Data and Interrogation Biometric Data.

Many modes of digitizing and processing biometric data can be incorporated into the systems and methods of the invention. For example, for fingerprint data, many approaches are available or in development to convert fingerprint scans to digitized forms and create searchable templates. Two major categories include minutia bases templates or pattern based templates. Pattern based templates are graphical images that are compressed for storage but are compared graphically. Minutiae based approaches, while also derived from a graphical image, can be used to create mathematical representations of such data for comparison. The M40 algorithm, utilized by the FBI, is one such mathematical representation. Another well known method of converting fingerprint images into an alphanumerical ordered series is the Vucetich Formula. Any reproducible method can be used to convert fingerprint scan data into suitable numerical or alphanumerical representations. In some embodiments, fingerprint scans are processed in similarly to those stored in the Integrated Automated Fingerprint Identification System (IAFIS) managed by the FBI.

DNA or RNA profiles can be converted into numerical representations by any suitable coding method. In one nonlimiting example, the profile from a nucleic acids analysis can be represented in terms of a gene identifier along with a locus identifier, which can be converted using ASCII encoding, in one nonlimiting example. Reordering nucleic acid profiles to present the same relative order of gene identifier and locus identifier may be necessary in order to obtain hashes that are comparable. In some embodiments, the order of presentation may be the same as the order of presentation as used in CODIS, managed by the FBI.

During the enrollment process, the first class of individualized biometric data obtained from an individual may be a fingerprint scan data. The digitized fingerprint scan of the individual may be converted to alphanumerical, numerical or matrixed values by any of the methods known in the art, as discussed above. In some embodiments, a first instance of the converted digitized fingerprint data is stored on the identification card. The second class of biometric data may be a DNA or RNA profile, which has been converted into an alphanumeric, numeric or matrixed value as discussed above. A second instance of the converted digitized fingerprint data is hashed together with the converted digitized DNA or RNA profile data of the individual, using, for example, a fuzzy hashing tool, to create a hashed value, which is stored on the identification card, as the individual information hash. In some embodiments, this hashed value is a barcode. In some embodiments, the barcode is a two dimensional barcode, including but not limited to a matrix code. In some embodiments, the hashing is a one-way hashing which provides a collision-free mechanism, and provides a product hash having a fixed length. Similar methods are used for any additional individualized identification hashes and/or one or more partial individualized identification hashes.

During the identification process, the processor retrieves the converted fingerprint data of the individual; accesses at least one interrogation database; and retrieves the plurality of interrogation biometric data of the second class, for example, DNA or RNA profiles of high risk individuals. The processor reorders each of the plurality of interrogation biometric data of the second class, if necessary; and converts each of the plurality of interrogation biometric data of the second class to an alphanumeric, numerical, or matrixed value of the same format as the individualized biometric data of the second class. The processor hashes the converted fingerprint data of the individual with each converted, digitized DNA or RNA data of the interrogation database, using the same hashing tools as used in the enrollment of the individual. In some embodiments, the hashing tool is a fuzzy hashing tool. Similar methods are used to form one or more partial interrogation database identification hashes. Each of the plurality of interrogation database identification hashes so formed is compared to the individualized identification hash retrieved from the identification card. The comparison may be made by a fuzzy hashing algorithm, seeking substantial identity but not requiring perfect identity. If substantial identity is found, a match is reported and further investigation of the individual as a high risk individual may follow.

In some embodiments, the processor performs comparison between the individualized biometric data of the first or third or more class and interrogation databases having biometric data of the respective classes. The method may include the steps of reordering or reorganizing the biometric data in the interrogation databases to be in the same order or presented in the same manner as that of the individualized biometric data. The method may also include the steps of processing the biometric data of the interrogation databases to be represented, encoded or mathematically manipulated in the same way as that of the individualized biometric data. Additionally, when the individualized biometric data of any of these classes includes a DNA data, and is present as a individualized identification hash formed from a combination of an individualized biometric data other than a DNA data with the DNA data, then the method includes steps for retrieving an instance of the individualized biometric data of the class other than the DNA data, and forming a plurality of interrogation database identification hashes and/or partial interrogation database identification hashes with DNA data of the interrogation database as described above; comparing the plurality of interrogation database identification hashes with the individualized identification hash; and reporting whether a match has been found.

In yet other embodiments, the processor performs a comparison between partial or degraded DNA profiles in an interrogation database and a plurality of individualized identification hashes containing partial DNA profile data stored on the identification card. The processor may perform a weighting analysis to determine if a threshold probability has been attained to permit reporting a match. In any embodiment when the database entry may not have a complete DNA profile, the processor may issue a report including percentage of alleles matched data, and number of loci compared. One of skill may customize the requirements for threshold matching criteria in order to program the processor to report whether the results constitute identification of a significant match.

Alternatively, the processor may assign probabilities that the comparisons between the partial individualized identification hashes and the partial interrogation data hashes represent a significant likelihood of a match. A match may be reported when these conditions are met.

Method of Producing the Identification Card.

An identification card is produced by acquiring individualized biometric data of at least a first and a second class from the individual. The individualized biometric data of the first class is converted into a digitized biometric data. At least a first instance of the digitized biometric data of the first class is stored on the identification card. In some embodiments, a second instance of the biometric data of the first class is stored on the card. The second instance of the biometric data may be stored on the identification card in a different format than the first instance of the biometric data of the first class. One non-limiting example the identification card may include a fingerprint data scan stored as a digitized data string and may also have a graphical representation of the fingerprint scan stored on the identification card. The individualized biometric data of the second class may be converted into a digitized biometric data and is hashed with another instance of the digitized individualized biometric data of the first class to form a first individualized identification hash. The first individualized identification hash is stored on the identification card. In some embodiments, the individualized identification hash is a one-way hash. In some embodiments, more than one individualized identification hash and/or a plurality of partial individualized identification hashes may be stored on the identification card. In some embodiments, the first instance of the individualized biometric data of the first class is hashed in an invertible form prior to storage on the card. In some embodiments, more than two classes of individualized biometric data are acquired, converted to digital electronic formats, and stored on the identification card. When any third or more class of individualized biometric data is a DNA data, it is hashed with a non-DNA individualized biometric data prior to storage on the identification card. When the third or more class of individualized DNA biometric data is hashed with non-DNA individualized biometric data, the hashing may be one-way. In some embodiments an enrollment verification certification is stored on the card. In any embodiments, where the identification card itself does not carry individualized identification information including the individualized biometric data of the individual, a password or other electronic entry permission granting device is stored on the card. This permits the retrieval of the individualized identification information, upon presentation of the identification card at the point of contact, from another database, which may be the enrollment database.

The storing of any of the biometric data on the identification may be accomplished by any suitable method, including but not limited to graphical, text, pictorial, barcode, alphanumeric or two dimensional marking. The marking may be magnetic, visually readable, or electronic. The identification card may further comprise parametic identification embedded or printed on it.

EXAMPLES

The specific algorithms described in these examples, used to convert graphical scan data such as fingerprint, iris, retina, facial feature recognition, body geometry and others into digitized representations (templates) are non-limiting examples of the types of algorithms that may be used. Many other mathematical manipulation types are envisioned to produce useful digitized representations and identification hashes for the methods of the invention.

Example 1. Enrollment of an Individual Using Fingerprint Scan Data and DNA Data

An individual produces a sample of personal biological material for DNA STR profiling and presents a single digit to be scanned by a Futronics RIPS201/PIV USB 2.0 fingerprint scanner.

The individual's biological sample is processed to extract the crude DNA, the DNA is amplified using primers and a DNA STR profile is determined by analysis using an Identifiler® STR kit (Life Technologies). The results are presented as a string of digits, representing the number of alleles found for each loci, ordering the loci as AMEL, CSF1PO, D13S317, D16S539, D18S51, D19S433, D21S11, D2S1338, D3S1358, D5S81, D7S820, D8S1179, FGA, TH01, TPDX, vWA, and can be written as data string 001:
XX101288111218201515.22931202315161112101211414 202679891719

The fingerprint scan obtained as above is output as a numerical template by VeriFinger SDK 6.4 (NeuroTechnology), represented here as data string 002:
00115901964198069806A-0021793194820116A-
0031326195319806B-0041458224320411-B-
0051808211120306A-0061956290321816A-
0072123347221811B-0082017234522406-A-
0091758237022111B-0102123254822406A-
0112123271022106A-0122403272022911-A-
01323272980003916A-0141773249703716A-
0152123249704306A-0162301271004006-A9.014:
009.015:169.016:AFIS/FBIA1NMV9.017:
UC31319.020:09.023:00115901935018-
06A00502009070040625515003022551525515002021
1100001-0021793195102116A25515-
005040091000102003022551525515255015010100000-
0031326194601806B0010200404-
2551525515255152555125551525551501000000-
0041458165602411B009010060625515-
2551525515003040010600506000000011-
0051808178802306A2551500803009060000406-
00102002042551525515000011100-
0061956099603816A2551500707255152555150000406-
01405011060130300001011-
0072123042703811B25515255152555152555152555150
0607-013112551500000000-
00820171554044066A015010110501400600090400504006032
551525515-2551510101000-
00917581529041111B0150201402255152555150000410
05062551500804-000000100-
0102123135104406A01600011030060801404008030
150225515255150-01011100-
0112123118904106A01302007130060625515014020
10032551501603-11000101-
0122403117904911A25515013050061001602010022
551525515-5515-01110000-
0132327091921916A0110201205255152555150255152
55150071100603-11000001-
0141773140221716A0040010090200806015015011020
060552551525515-11110000-
0152123140222306A00801255152555152555150016020
10020060901405-10001101-
0162301118922006A0100025551525515012002255150

13050060901103-10010011,
XX101288111218201515.22931202315161112101214
14202679891719

The individualized identification hash is obtained by encryption of the combined strings using MessageDigestClass from Java Encryption API, which includes a revised Secure Hash Algorithm (SHA-1, developed by NSA, and published by NIST) algorithm. The result can be written in a 160 bit data string as individualized identification hash 003:

MNSPDUdtQTr3DsqyJVmrCTeFB0M=

An identification card is produced for the individual, having the fingerprint template data string 002 and the individualized identification hash 003 present on the card. The identification card also includes descriptors for the biometric data string 002 and individualized identification hash data string 003 that identifies what type of data (i.e., fingerprint scan template and hashed fingerprint template/DNA profile) is represented by these data strings. Parametric information such as name, age, address, citizenship, residency status, and the like is also included.

Example 2. Method of Accessing Information and Interrogating Databases Containing DNA Data The individual presents the identification card of Example 1, and the processor reads the data string 002 and data string 003, along with the descriptors identifying the types of biometric data included in the data strings and also identifies the method of organizing/reordering biometric data used. The processor communicates to a database containing DNA STR data, including, for example, 158 individual STR profiles comprising the same loci as used in Example 1. For each DNA profile in the database, the processor first reorders the DNA loci of the STRs to be represented in same order and digitized manner as used in Example 1. The processor forms an interrogation database identification hash by extracting the data string 002 from the identification card of the individual, and encrypts the combined strings using MessageDigestClass from Java Encryption API, to provide an interrogation database identification hash for each of the DNA profiles in the database (interrogation database identification hash 005-1 to 005-158). Each interrogation database identification hash is compared by the processor with the individualized identification hash:

MNSPDUdtQTr3DsqyJVmrCTeFB0M=of Example 1, and the report is issued whether a match has been identified:

Match found at STR profile:
XX101288111218201515.22931202315161112101214
14202679891719
Generated by fingerprint: 0011590196419806A-0021793194820116A-0031326195319806-B-0041458224320411B-0051808211120306A-0061956290321816A-0072123347221811-B-0082017234522406A-0091758237022111B-0102123254822406A-0112123271022106-A-0122403272022911A-0132327298003916A-0141773249703716A-0152123249704306-A-0162301271004006A9.014:009.015:169.016:AFIS/FBIA1NMV9.017:UC31-319.020:09.023:
0011590193501806A0050200907004062551500302255152551500202-11100001-
0021793195102116A2551500504009100010200302255152551525515-01010000-
0031326194601806B00102004042551525515255152
55152551525515-01000000-
0041458165602411B00901006062551525515255150
03040010600506-00000011-
0051808178802306A25515008030090600406001020
02042551525515-00011100-
0061956099603816A25515007072551525515004060
14050110601303-00001011-
0072123042703811B25515255152551525515255150
06070131125515-00000000-
0082017155404406A01501011050140600904005032
55152551525515-10101000-
0091758152904111B01502014022551525515004010
05062551500804-00000100-
0102123135104406A01600011030060801404008030
15022551525515-01011100-
0112123118904106A01302007130060625515014020
10032551501603-11000101-
0122403117904911A25515013050061001602010022
55152551525515-01110000-
0132327091921916A01102012052551525515255152
55150071100603-11000001-
0141773140221716A00401009020080601505011020
06052551525515-11110000-
0152123140222306A00801255152551525515016020
10020060901405-10001101-
0162301118922006A01000255152551501202255150
13050060901103-10010011,
XX101288111218201515.22931202315161112101214
14202679891719

Creating UID: MNSPDUdtQTr3DsqyJVmrCTeFB0M=

As can be seen, a match is identified between the individual and one of the Database entries, which has the same DNA profile.

Example 3. Enrollment of an Individual Using Iris Scan Data and DNA Data

The individual's DNA STR profile is obtained as described in Example 1, and can be written as described above as data string 001:
XX101288111218201515.22931202315161112101214
4202679891719

An iris scan is output as a numerical template using a VeriEye Extended SDK Version 2.5 (Neurotechnology), represented here as data string 004:
78.69.82.16.24.9.16.128.2.224.1.0.223.1.5.2.64.0.32.0.2
50.7.160.13.95.234.7.224.95.193.
104.5.254.168.15.106.95.213.106.7.210.40.37.224.87.
127.0.181.122.10.21.253.108.41.12
5.183.202.130.95.160.125.246.138.21.247.210.160.15
1.224.160.127.160.181.120.37.232.
87.168.23.250.7.218.8.215.250.7.160.13.95.234.7.160.
95.197.120.5.254.168.15.42.95.21
3.122.2.210.168.1.250.87.253.53.165.122.10.85.253.
108.161.124.149.250.3.95.128.125.2
42.138.21.245.242.160.23.240.160.127.160.181.120.
37.248.23.168.23.250.7.250.33.87.2
24.5.160.149.95.234.130.160.95.213.248.23.248.168.
40.169.95.85.104.160.87.194.128.2
54.23.127.85.165.90.9.127.241.124.161.126.133.122.
1.254.129.253.234.10.85.247.194.1
60.31.212.168.31.160.149.250.1.248.5.170.23.250.7.
248.33.87.240.160.160.221.127.194.
130.160.95.213.252.151.160.40.10.169.95.85.232.40.
23.210.128.170.23.223.245.160.90.
9.125.232.124.161.126.129.122.1.255.3.245.42.10.87.
255.210.160.23.210.160.127.160.9
5.122.1.248.0.42.23.250.7.248.15.87.213.224.181.

245.250.7.130.128.95.213.245.226.
160 .95.128.168.95.127.168.40.23.214.128.138.23.87.
247.130.10.133.125.232.36.161.126.12
9.126.129.253.122.128.74.3.87.255.90.160.31.218.12
9.95.160.31.86.160.23.160.10.7.250
21.248.11.215.213.224.23.245.170.23.194.130.95.213.
245.224.160.95.128.168.31.215.2
32.40.23.215.160.128.23.87.215.138.130.149.253.1
22.0.168.23.160.94.129.245.250.1.12
2.129.95.248.10.136.7.218.1.87.232.10.23.160.7.252.
10.3.250.21.250.10.215.213.240.87.
224.42.87.250.130.31.215.245.168.1.94.129.232.23.
215.232.2.23.215.160.128.95.215.22
3.138.2.85.245.126.160.168.23.224.94.129.247.234.5.
254.129.223.232.10.10.5.90.1.85.2
48.10.23.232.7.254.10.128.170.23.254.10.7.213.253.
127.160.42.87.250.2.151.213.254.16
8.15.94.129.232.23.215.234.2.215.215.226.128.95.
215.95.13 8.2.87.245.95.160.42.23.
248 .94.129.87.232.5.254.129.223.160.10.2.161.126.
11.85.248.10.23.232.21.254.2.128.168.2
3.255.10.7.161.245.254.160.15.87.250.2.150.213.254.
40.23.250.129.168.23.215.234.3.21
5.215.250.128.95.245.95.138.10.87.213.95.160.42.7.
254.2.129.95.160.21.250.129.223.13
8.15.87.129.127.9.213.232.10.23.234.21.254.2.128.
168.23.245.250.130.160.85.250.0.23.
215.17.82.87.213.248.2.87.250.2.160.31.87.234.7.
224.181.254.128.87.250.10.130.10.95.
215.95.160.42.5.254.130.133.95.160.21.248.1.255.
170.7.215.161.122.21.245.168.10.215.
250.21.250.7.224.168.21.245.127.130.130.213.39.
192.87.212.46.58.87.245.248.3.215.25
0.2.160.31.87.234.23.224.37.126.160.21.250.2.23.
170.95.215.222.160.42.5.126.128.149.
254.128.245.232.5.254.42.31.214.133.248.53.248.
168.42.151.95.21.234.7.250.32.117.22
9.127.130.150.213.27.128.87.249.9.83.87.229.248.7.
213.234.2.160.53.95.168.23.224.37.
127.160.21.250.128.23.250.31.87.222.160.10.1.254.
160.21.250.129.245.232.5.248.40.95.
214.149.232.21.248.32.63.137.95.117.168.23.250.0.
117.161.127.130.215.165.11.129.245 .
245.9.251.87.224.42.7.213.234.130.160.181.95.160.
95.232.41.127.224.149.250.128.23.2
22.15.95.215.170.10.129.254.160.53.250.133.247.
160.5.248.40.95.210.149.232.117.248.
0.95.137.95.116.168.21.250.0.245.160.127.131.87.
225.75.129.245.255.170.163.87.224.4
2.151.213.224.129.160.165.94.160.95.234.1.87.224.
149.254.160.31.222.9.95.87.126.10.1
30.222.168.53.250.5.247.160.53.248.1.95.210.176.
169.125.232.1.95.136.95.116.168.23.2
48.0.245.160.63.95.215.225.113.1.245.245.104.107.
95.232.42.23.213.160.133.224.161.9
4.160.127.122.0.215.224.149.254.160.31.95.9.95.85.
126.2.130.130.168.55.250.133.215.1
68.53.232.1.127.215.160.173.125.232.3.95.136.95.94.
168.23.248.2.213.224.161.95.213.2
25.81.1.117.210.53.103.95.232.10.87.208.160.181.
240.169.95.160.125.122.128.245.248.
149.254.160.31.95.104.31.117.126.130.30.130.160.
125.254.149.223.168.53.232.1.127.21
5.160.181.127.168.3.223.10.31.94.168.23.224.15.245.
240.161.255.213.245.122.1.117.21
5.245.155.95.104.10.87.208.129.245.244.168.95.160.
125.94.129.245.104.53.120.168.95.

95.122.13.253.126.128.95.128.160.125.119.245.95.
168.55.232.5.127.87.160.181.127.168 .
14.136.95.13.124.168.23.224.47.165.240.161.127.
213.245.122.0.87.252.70.207.95.106.1
0.87.224.181.213.245.168.31.160.61.94.129.252.40.
53.120.40.31.253.122.5.253.126.160.
95.128.160.125.117.245.94.160.127.170.9.125.87.
160.181.127.40.34.168.95.41.127.40.2
3.224.53.165.240.160.127.95.213.126.160.95.160.62.
127.127.74.130.23.224.181.215.245 .
234.31.160.61.90.129.252.40.37.120.42.21.253.94.5.
253.126.160.95.160.7.253.117.245.
94.160.127.2.168.125.87.224.184.75.124.64.168.95.
161.127.168.23.224.53.161.252.160.
127.95.223.86.160.127.160.43.93.127.86.130.23.224.
245.215.215.234.31.160.125.90.1.2
45.232.5.120.10.133.253.95.5.125.118.160.95.232.31.
200.117.245.90.161.127.2.136.127.
87.245.224.146.5.193.138.159.129.127.160.23.224.63.
161.252.160.127.23.219.86.161.12
6.160.23.221.250.23.130.23.245.245.87.215.234.31.
160.125.90.129.245.234.1.125.10.12
9.255.95.129.127.128.168.23.232.30.0.85.245.90.160.
127.2.128.95.3.215.57.208.72.164.
183.238.129.126.128.21.241.126.161.126.41.127.23.
218.23.161.254.160.23.245.168.23.1
30.23.245.252.23.215.234.30.160.125.94.129.245.
234.1.125.94.131.95.95.129.95.129.23
2.5.253.126.0.93.252.82.160.127.74.128.95.121.87.
168.219.70.81.16.234.129.126.128.18
1.229.126.40.90.236.250.23.250.23.161.254.160.181.
245.168.23.168.7.213.254.7.215.23
4.31.160.63.222.129.213.234.5.120.30.10.95.86.131.
95.129.232.5.253.120.40.93.244.210 .
160.127.74.128.95.252.87.69.34.16.230.40.207.213.
126.128.244.133.127.40.90.186.186.
23.250.23.161.254.160.21.245.160.23.232.15.213.
250.7.244.170.87.160.31.214.131.213.
232.29.104.31.74.95.2.131.95.193.232.5.245.124.40.
31.246.210.160.127.10.129.95.248.5 .
29.238.191.219.201.167.87.250.128.248.133.127.40.
26.195.184.23.242.151.129.253.168 .
21.254.160.87.232.15.213.250.15.88.163.74.232.31.
215.215.214.160.125.40.31.250.10.2 .
215.87.213.168.15.245.253.40.31.215.210.128.122.
10.133.213.251.188.121.74.219.35.1
62.3.87.250.128.232.5.127.104.10.118.232.23.242.
135.129.253.168.21.254.0.85.232.1.21
5.240.52.16.161.247.48.15.215.215.130.161.125.40.
31.218.8.10.95.87.213.232.15.213.25
3.104.15.151.218.129.250.31.213.236.136.12.119.
141.202.2.85.132.243.238.36.232.41.9
5.122.2.160.168.23.242.151.161.245.168.23.250.3.
215.232.3.215.232.207.123.21.102.13
1.50.23.215.130.165.124.40.95.218.168.47.95.94.
133.234.2.133.245.232.14.135.218.128.
67.95.251.64.193.72.126.133.234.237.193.93.155.0.
60.56.40.95.94.128.160.42.151.242.1
35.160.245.232.23.250.11.87.226.12.34.78.149.206.
156.34.112.235.123.210.130.181.252 .
40.95.94.168.63.95.94.133.250.2.129.245.232.14.
129.90.131.180.180.179.114.214.121.5
0.254.64.69.206.174.97.71.5.196.40.31.94.128.248.
10.197.250.135.224.247.232.23.232.1
1.87.224.137.232.44.20.84.162.210.137.152.101.242.
128.245.248.168.127.94.160.63.93.
126.133.254.130.129.117.232.15.168.90.140.99.183.

192.61.232.122.146.37.171.39.173.2
00.40.186.63.249.168.15.95.160.248.23.225.126.5.
240.247.232.87.232.11.87.224.44.68.1
82.15.121.205.24.49.22.167.218.133.245.232.160.127.
94.160.126.21.122.5.255.130.161.
117.232.21.232.10.131.23.108.240.238.117.111.253.
119.174.61.186.186.162.116.31.202.
40.11.95.160.168.87.225.126.129.245.127.202.87.232.
9.95.224.71.192.77.230.40.127.4.8
1.42.5.218.133.247.170.160.127.31.168.62.21.122.5.
255.128.161.117.224.149.248.10.14
6.245.101.40.29.6.48.113.51.21.123.92.162.51.242.
191.42.40.11.95.224.168.87.224.126.
129.245.255.74.87.168.9.95.224.191.109.80.246.69.
140.227.224.206.50.154.213.215.130 .
129.126.30.40.58.21.120.5.255.160.161.125.224.181.
248.10.14.91.5.248.90.162.29.71.1
1.36.212.121.126.199.41.21.223.40.10.95.240.161.87.
16.0.16.0.145.228.217.196.249.134 .
245.143.143.140.225.227.140.230.198.99.147.192.
249.128.240.226.253.142.153.156.19
5.227.140.230.70.103.231.152.252.48.240.240.252.
30.12.142.35.129.140.113.134.99.252 .
56.252.96.112.240.252.63.6.204.99.1.142.17.192.113.
56.118.248.224.121.184.228.63.7.
28.231.28.220.57.128.124.62.241.249.224.241.28.227.
191.7.24.198.61.184.95.24.220.21
2.252.225.224.115.140.99.223.130.57.198.57.56.206.
24.207.246.225.227.198.115.142.99 .
207.128.57.198.124.112.206.56.227.248.244.227.159.
51.140.99.231.204.63.204.124.112 .
55.49.99.248.193.227.191.19.156.97.247.204.127.
140.62.230.179.27.99.108.199.49.255.
147.142.112.243.6.143.140.59.203.87.31.46.100.207.
49.231.51.206.100.227.7.142.140.5
6.152.126.39.34.228.198.49.254.35.240.206.15.199.
199.137.228.169.181.103.142.228.19
8.113.238.47.161.206.31.97.229.132.223.69.48.131.
200.100.206.48.121.230.23.143.62.1
13.228.15.137.8.11.105.195.39.204.50.148.119.135.
15.38.113.238.23.179.178.88.128.22 7.

The individualized identification hash is obtained by encryption of the combined strings using MessageDigest-Class from Java Encryption API, which includes a revised Secure Hash Algorithm (SHA-1, developed by NSA, and published by NIST) algorithm. The result can be written in a 160 bit data string as individualized identification hash 005:

jLGs0bKsVyf1Sao9/N+mMMo598=

An identification card is produced for the individual, having the iris template data string 004 and the individualized identification hash 005 present on the card. The identification card also includes descriptors for the biometric data string 004 and individualized identification hash data string 005 that identifies what type of data (i.e., iris can template and hashed iris template/DNA profile) is represented by these data strings. Parametric information such as name, age, address, citizenship, residency status, and the like is also included.

Example 4. Method of Accessing Information and Interrogating Databases Containing DNA Data The individual presents the identification card of Example 3, and the processor reads the data string 004 and individualized identification hash data string 005, along with the descriptors identifying the types of biometric data included in the data strings and also identifies the method of organizing/reordering biometric data used. The processor communicates to a database containing DNA STR data, including, for example, 158 individual STR profiles comprising the same loci as used in Example 1. Interrogation of each interrogation database identification hash is performed in the same manner as in Example 2, in this case using the data string 004 to form an interrogation database identification hash for each entry of the interrogation database. Each of the resulting interrogation database identification hashes is compared with the individualized identification hash (jLGs0bKsVyf1Sao9/N+mMMo598=) of Example 3, and the report is issued whether a match has been identified.

While the principles of the present teachings have been described in connection with specific embodiments of nucleic acid sample preparation and sequencing platforms, it should be understood clearly that these descriptions are made only by way of example and are not intended to limit the scope of the present teachings or claims. What has been disclosed herein has been provided for the purposes of illustration and description. It is not intended to be exhaustive or to limit what is disclosed to the precise forms described. Many modifications and variations will be apparent to the practitioner skilled in the art. What is disclosed was chosen and described in order to best explain the principles and practical application of the disclosed embodiments of the art described, thereby enabling others skilled in the art to understand the various embodiments and various modifications that are suited to the particular use contemplated. It is intended that the scope of what is disclosed be defined by the following claims and their equivalents.

The invention claimed is:

1. An identification card comprising:

individualized identification information of an individual, the individualized identification information comprising:

individualized biometric data of at least a first class, wherein the individualized biometric data of the first class comprises one or more of fingerprint scan data, palm print scan data, retinal scan data, iris scan data, hand vein scan data, facial recognition scan data, or body geometry scan data, and a first individualized identification hash, the first individualized identification hash comprising the individualized biometric data of the first class hashed with individualized biometric data of a second class, wherein the individualized biometric data of the second class comprises DNA data, wherein the DNA data is securely stored on the identification card by way of being hashed with the individualized biometric data of the first class such that the individualized biometric data of the first class of the identification card is combined with DNA data of one or more interrogation databases to form one or more interrogation database identification hashes and compared with the first individualized identification hash without directly exposing the DNA data of the individual.

2. The identification card of claim 1, wherein the individualized biometric data of the second class is selected from the group consisting of a STR profile, a SNP profile, an INDEL profile, and an Alu element.

3. The identification card of claim 1, wherein the individualized biometric data of the second class comprises a STR profile.

4. The identification card of claim 1, wherein the individualized biometric data further comprises a third or more class of biometric data selected from the group consisting of a fingerprint scan data, iris scan data, retinal scan data, facial recognition scan data, and body geometry scan data and a DNA data, wherein the DNA data is selected from the group consisting of a STR profile, a SNP profile, an INDEL profile, and an Alu element.

5. The identification card of claim 1, further comprising a plurality of partial individualized identification hashes, wherein each partial individualized identification hash comprises the individualized biometric data of the first class and a partial individualized biometric data of the second class.

6. The identification card of claim 1, further comprising at least one descriptor of a type and/or subtype of the individualized biometric data.

7. The identification card of claim 1, further comprising a first instance of the individualized biometric data of the first class presented on the identification card as graphical data.

8. The identification card of claim 7, wherein the individualized biometric data of the first class is a fingerprint data, wherein the fingerprint data is presented on the identification card as graphical data.

9. The identification card of claim 1, wherein the individualized biometric data of the first class comprises one or more of fingerprint scan data, palm print scan data, retinal scan data, iris scan data, hand vein scan data, facial recognition scan data, or body geometry scan data, and wherein the individualized biometric data of the second class comprises one or more of an STR profile, a SNP profile, an INDEL profile, or an Alu element.

10. The identification card of claim 9, further comprising a plurality of partial individualized identification hashes, wherein each partial individualized identification hash comprises the individualized biometric data of the first class and a partial individualized biometric data of the second class, wherein each partial individualized biometric data of the second class comprises a different subset of loci of a DNA profile.

11. The identification card of claim 5, wherein each partial individualized biometric data of the second class comprises a different subset of loci of a DNA profile.

12. An identification card comprising individualized identification information of an individual, the individualized identification information comprising:
   individualized biometric data of at least a first class, the individualized biometric data of the first class comprising one or more of fingerprint scan data, palm print scan data, retinal scan data, iris scan data, hand vein scan data, facial recognition scan data, or body geometry scan data; and
   a first individualized identification hash, the first individualized identification hash comprising the individualized biometric data of the first class hashed with individualized biometric data of a second class, wherein the individualized biometric data of the second class is DNA data comprising one or more of an STR profile, a SNP profile, an INDEL profile, or an Alu element,
   wherein the DNA data is securely stored on the identification card by way of being hashed with the individualized biometric data of the first class such that the individualized biometric data of the first class of the identification card is combined with DNA data of one or more interrogation databases to form one or more interrogation database identification hashes and compared with the first individualized identification hash without directly exposing the DNA data of the individual.

13. The identification card of claim 12, further comprising a plurality of partial individualized identification hashes, wherein each partial individualized identification hash comprises the individualized biometric data of the first class and a partial individualized biometric data of the second class.

14. The identification card of claim 13, wherein each partial individualized biometric data of the second class comprises a different subset of loci of a DNA profile.

15. An identification card comprising individualized identification information of an individual, the individualized identification information comprising:
   individualized biometric data of at least a first class comprising one or more of fingerprint scan data, palm print scan data, retinal scan data, iris scan data, hand vein scan data, facial recognition scan data, or body geometry scan data; and
   a plurality of partial individualized identification hashes, wherein each partial individualized identification hash comprises the individualized biometric data of the first class and a partial individualized biometric data of a second class,
   wherein each partial individualized biometric data of the second class comprises DNA data corresponding to a different subset of loci of a DNA profile,
   wherein the DNA data is securely stored on the identification card by way of being hashed with the individualized biometric data of the first class such that the individualized biometric data of the first class of the identification card is combined with DNA data of one or more interrogation databases to form one or more interrogation database identification hashes and compared with the first individualized identification hash without directly exposing the DNA data of the individual.

16. The identification card of claim 15, wherein the individualized biometric data of the second class is DNA data comprising one or more of an STR profile, a SNP profile, an INDEL profile, or an Alu element.

* * * * *

UNITED STATES PATENT AND TRADEMARK OFFICE
CERTIFICATE OF CORRECTION

| | | |
|---|---|---|
| PATENT NO. | : 11,636,190 B2 | Page 1 of 1 |
| APPLICATION NO. | : 16/915667 | |
| DATED | : April 25, 2023 | |
| INVENTOR(S) | : Leonard Klevan et al. | |

It is certified that error appears in the above-identified patent and that said Letters Patent is hereby corrected as shown below:

On the Title Page

Please add --(73) Assignee: LIFE TECHNOLOGIES CORPORATION, Carlsbad, CA--

Signed and Sealed this
Fourteenth Day of January, 2025

Derrick Brent
*Acting Director of the United States Patent and Trademark Office*